United States Patent
Paydar et al.

(10) Patent No.: US 11,426,269 B2
(45) Date of Patent: Aug. 30, 2022

(54) SYSTEMS AND METHODS FOR ACELLULAR DERMAL MATRIX FENESTRATIONS IN PREPECTORAL BREAST RECONSTRUCTION

(71) Applicant: The Regents of the University of California, Oakland, CA (US)

(72) Inventors: Keyianoosh Z. Paydar, Orange, CA (US); Garrett A. Wirth, Orange, CA (US); Patrick Guidotti, Irvine, CA (US); Donald S. Mowlds, Orange, CA (US)

(73) Assignee: The Regents of the University of California, Oakland, CA (US)

( * ) Notice: Subject to any disclaimer, the term of this patent is extended or adjusted under 35 U.S.C. 154(b) by 49 days.

(21) Appl. No.: 16/605,470

(22) PCT Filed: Apr. 20, 2018

(86) PCT No.: PCT/US2018/028644
§ 371 (c)(1),
(2) Date: Oct. 15, 2019

(87) PCT Pub. No.: WO2018/195476
PCT Pub. Date: Oct. 25, 2018

(65) Prior Publication Data
US 2020/0222177 A1 Jul. 16, 2020

Related U.S. Application Data

(60) Provisional application No. 62/487,988, filed on Apr. 20, 2017.

(51) Int. Cl.
*A61F 2/12* (2006.01)

(52) U.S. Cl.
CPC ........ *A61F 2/12* (2013.01); *A61F 2210/0057* (2013.01); *A61F 2250/0023* (2013.01)

(58) Field of Classification Search
CPC .. A61F 2/12; A61F 2/0036; A61F 2210/0057; A61F 2250/0023
(Continued)

(56) References Cited

U.S. PATENT DOCUMENTS

| 8,049,059 B2 | 11/2011 | Bleyer et al. |
| 2004/0260315 A1 | 12/2004 | Dell et al. |

(Continued)

FOREIGN PATENT DOCUMENTS

WO   WO-2013/106556 A2   7/2013

OTHER PUBLICATIONS

Final Office Action dated Jul. 20, 2020, from U.S. Appl. No. 15/032,567.
(Continued)

*Primary Examiner* — Suzette J Gherbi
(74) *Attorney, Agent, or Firm* — Foley & Lardner LLP

(57) ABSTRACT

A reconstruction support includes an upper half, a lower half joined to the upper half, a plurality of alignment perforations disposed on at least one of the upper half and the lower half, and a plurality of fenestrations disposed on at least one of the upper half and the lower half, the plurality of fenestrations configured to facilitate selective expansion of at least one of the upper half or the lower half, where the reconstruction support is inserted above muscle to facilitate breast reconstruction.

23 Claims, 37 Drawing Sheets

(58) Field of Classification Search
USPC .......................................................... 623/7–8
See application file for complete search history.

(56) References Cited

U.S. PATENT DOCUMENTS

| | | | |
|---|---|---|---|
| 2006/0141012 A1 | 6/2006 | Gingras | |
| 2007/0055371 A1* | 3/2007 | Laghi .................... | A61F 2/5046 623/7 |
| 2008/0097601 A1 | 4/2008 | Codori-Hurff et al. | |
| 2009/0125107 A1 | 5/2009 | Maxwell | |
| 2011/0022171 A1 | 1/2011 | Richter et al. | |
| 2011/0262515 A1 | 10/2011 | Lauritzen et al. | |
| 2011/0288568 A1* | 11/2011 | Capuzziello .......... | A61F 2/0063 606/151 |
| 2012/0143329 A1 | 6/2012 | Kim | |
| 2013/0085579 A1 | 4/2013 | Markman | |
| 2014/0276993 A1* | 9/2014 | Reilly .................... | A61F 2/0063 606/151 |
| 2015/0157451 A1 | 6/2015 | Bowley et al. | |
| 2015/0250582 A1 | 9/2015 | Greenhalgh et al. | |
| 2015/0272723 A1* | 10/2015 | Hristov .................... | A61F 2/12 623/8 |
| 2016/0082235 A1* | 3/2016 | Mosharrafa ............ | A61M 29/02 606/192 |
| 2016/0256259 A1* | 9/2016 | Wirth ........................ | A61F 2/12 |
| 2016/0331504 A1 | 11/2016 | Wang et al. | |
| 2017/0340437 A1 | 11/2017 | Bowley et al. | |
| 2017/0367807 A1 | 12/2017 | Chen et al. | |
| 2018/0055624 A1 | 3/2018 | Barere et al. | |
| 2019/0247175 A1* | 8/2019 | Wang ........................ | A61F 2/12 |
| 2019/0350697 A1* | 11/2019 | Algawi .................... | G16H 40/67 |
| 2020/0268503 A1* | 8/2020 | Rehnke .................... | A61L 27/20 |
| 2021/0052367 A1* | 2/2021 | Yang ......................... | A61F 2/00 |

OTHER PUBLICATIONS

Notice of Allowance dated Oct. 9, 2020, from U.S. Appl. No. 15/032,567.
European Office Action dated Mar. 31, 2021, from application No. 14858603.5.
Non-Final Office Action dated Dec. 4, 2019, from U.S. Appl. No. 15/032,567.
Artz, et al., "Breast reconstruction with a subcutaneous tissue expander followed with a polyurethanecovered silicone breast implant," Annals of Plastic Surgery, vol. 20, issue 6, pp. 517-521 (Jun. 1988).
Becker, et al., "Immediate implant-based prepectoral breast reconstruction using a vertical incision," PRS Global Open, vol. 3(6), e412, 9 pages (Jun. 2015).
Bernini, et al., "Subcutaneous direct-toimplant breast reconstruction: surgical, functional, and aesthetic results after long-term follow-up," PRS Global Open, vol. 3(12), e574, 9 pages (Dec. 2015).
Caputo, et al., "Skin-reduction breast reconstructions with prepectoral implant," Plastic and Reconstructive Surgery, vol. 137, issue 6, pp. 1702-1705 (Jun. 2016).
Casella, et al., "TiLoop(R) Bra mesh used for immediate breast reconstruction: comparison of retropectoral and subcutaneous implant placement in a prospective single-institution series," European Journal of Plastic Surgery, vol. 37, issue 11, pp. 599-604 (Nov. 2014).
Cheng, et al., "Treatment of Capsular Contracture Using Complete Implant Coverage by Acellular Dermal Matrix: A Novel Technique," Plastic and Reconstructive Surgery, vol. 132, issue 3, pp. 519-529 (Sep. 2013).
Downs & Hedges, "An alternative technique for immediate direct-to-implant breast reconstruction—a case series," PRS Global Open, vol. 4(7), e821, 8 pages (Jul. 2016).
Engel, et al., "Subcutaneous tissue expansion and subsequent subpectoral implantation for breast reconstruction in Asian patients: safety and outcome," Annals of Plastic Surgery, vol. 70, issue 2, pp. 135-143 (Feb. 2013).

Extended European Search Report dated Jul. 3, 2017, from application No. 14858603.5.
Final Office Action dated Mar. 8, 2018, from U.S. Appl. No. 15/032,567.
Gruber, et al., "Breast reconstruction following mastectomy: a comparison of submuscular and subcutaneous techniques," Plastic and Reconstructive Surgery, vol. 67, issue 3, pp. 312-317 (Mar. 1981).
Guthrie, "Breast reconstruction after radical mastectomy," Plastic and Reconstructive Surgery, vol. 57, issue 1, pp. 14-22 (Jan. 1976).
International Preliminary Report on Patentability dated Mar. 12, 2016, from application No. PCT/US2014/062466.
International Search Report and Written Opinion dated Jul. 10, 2018, for application No. PCT/US2018/028644.
International Search Report and Written Opinion dated Mar. 24, 2015, for application No. PCT/US2014/062466.
Iqbal, et al., "Host integration of an acellular dermal matrix: Braxon mesh in breast reconstruction," Clinical Breast Cancer, vol. 16, issue 6, pp. e209-e211 (Dec. 2016).
Kim, et al., "A meta-analysis of human acellular dermis and submuscular tissue expander breast reconstruction," Plastic and Reconstructive Surgery, vol. 129, issue 1, pp. 28-41, (Jan. 2012).
Krishnan, et al., "Is Single-Stage Prosthetic Reconstruction Cost Effective? A Cost-Utility Analysis for the Use of Direct-to-Implant Breast Reconstruction Relative to Expander-Implant Reconstruction in Postmastectomy Patients," Plastic and Reconstructive Surgery, vol. 138, issue 3, pp. 537-547 (Sep. 2016).
Martin, et al., "Use of Fenestrations in Acellular Dermal Allograft in Two-Stage Tissue Expander/Implant Breast Reconstruction," Plastic and Reconstructive Surgery, vol. 134, issue 5, pp. 901-904 (Nov. 2014).
Mowlds, et al., "Capsular contracture in implant-based breast reconstruction: examining the role of acellular dermal matrix fenestrations," Plastic and Reconstructive Surgery, vol. 136, issue 4, pp. 629-635 (Oct. 2015).
Non-final Office Action dated Jun. 8, 2017, from U.S. Appl. No. 15/032,567.
Palaia, et al., "Incidence of seromas and infections using fenestrated versus nonfenestrated acellular dermal matrix in breast reconstructions," PRS Global Open, vol. 3(11), e569, 7 pages (Nov. 2015).
Radovan, "Breast reconstruction after mastectomy using the temporary expander," Plastic and Reconstructive Surgery, vol. 69, issue 2, pp. 195-208 (Feb. 1982).
Reitsamer & Peintinger, "Prepectoral implant placement and complete coverage with porcine acellular dermal matrix: a new technique for direct-to-implant breast reconstruction after nipple-sparing mastectomy," Journal of Reconstructive and Aesthetic Surgery, vol. 68, issue 2, pp. 162-167 (Feb. 2015).
Salibian, et al., "Staged suprapectoral expander/implant reconstruction without acellular dermal matrix following nipple-sparing mastectomy," Plastic and Reconstructive Surgery, vol. 139, issue 1, pp. 30-39 (Jan. 2017).
Salibian, et al., "Subcutaneous implant-based breast reconstruction with acellular dermal matrix/mesh: a systematic review," PRS Global Open, vol. 4(11), e1139, 8 pages (Nov. 2016).
Schnarrs, et al., "Complication Rates With Human Acellular Dermal Matrices: Retrospective Review of 211 Consecutive Breast Reconstructions," PRS Global Open, vol. 4(11), e1118, 9 pages (Nov. 2016).
Sigalove, et al., "Prepectoral implantbased breast reconstruction: rationale, indications, and preliminary results," Plastic and Reconstructive Surgery, vol. 139, issue 2, pp. 287-294 (Feb. 2017).
Wirth, et al., "Acellular dermal matrix fenestrations and their effect on breast shape," European Journal of Plastic Surgery, vol. 38, issue 4, pp. 267-272 (Aug. 2015).
Zhu, et al., "Comparison of subcutaneous versus submuscular expander placement in the first stage of immediate breast reconstruction," Journal of Reconstructive and Aesthetic Surgery, vol. 69, issue 4, pp. e77-e86 (Apr. 2016).

* cited by examiner

SYSTEMS AND METHODS FOR ACELLULAR DERMAL MATRIX FENESTRATIONS IN PREPECTORAL BREAST RECONSTRUCTION

CROSS-REFERENCE TO RELATED PATENT APPLICATION

The present application is a national stage application under 35 U.S.C. § 371 of International Application No. PCT/US2018/028644, filed Apr. 20, 2018, which claims the benefit of, and priority to, U.S. Provisional Patent Application No. 62/487,988, filed Apr. 20, 2017, the contents of each of which are incorporated herein by reference in their entirety.

TECHNICAL FIELD

The present application relates generally to the field of prepectoral or subcutaneous breast reconstruction.

BACKGROUND

The use of acellular dermal matrices (ADMs) or acellular tissue matrices (ATMs) has become more prevalent in immediate one stage (i.e., direct to implant) and staged breast reconstruction (i.e., tissue expander followed by implant). These ADMs and ATMs are derived from cadaveric dermis and are composed primarily of extracellular matrix (ECM) components. The ADMs and ATMs function to provide a scaffold upon which resident (i.e., host) cells migrate following implantation, facilitating matrix integration and incorporation.

SUMMARY

In an embodiment, a reconstruction support is provided for insertion above muscle for the facilitation of breast reconstruction. The reconstruction support includes an upper half, a lower half joined to the upper half, a plurality of alignment perforations disposed on at least one of the upper half and the lower half, and a plurality of fenestrations disposed on at least one of the upper half and the lower half. The plurality of fenestrations is configured to facilitate selective expansion of at least one of the upper half or the lower half.

In another embodiment, a reconstruction support is provided for insertion above muscle for facilitation of breast reconstruction. The reconstruction support includes an upper half, a lower half, and a plurality of fenestrations. The lower half is integrated with the upper half. The plurality of fenestrations is disposed on at least one of the upper half and the lower half. The plurality of fenestrations is configured to facilitate selective expansion of at least one of the upper half or the lower half. The plurality of fenestrations is arranged in a plurality of substantially parallel rows. The plurality of substantially parallel rows includes a first row containing a first subset of the plurality of fenestrations, a second row positioned adjacent the first row containing a second subset of the plurality of fenestrations, a third row positioned adjacent the second row such that the second row is positioned between the first row and the third row and containing a third subset of the plurality of fenestrations, and a plurality of substantially concentric arcs. The plurality of substantially concentric arcs includes a first arc containing a fourth subset of the plurality of fenestrations and a second arc positioned adjacent the first arc and containing a fifth subset of the plurality of fenestrations.

In another embodiment, a reconstruction support is provided for insertion above muscle for facilitation of breast reconstruction. The reconstruction support includes an upper half, a lower half, and a plurality of fenestrations. The lower half is integrated with the upper half. The plurality of fenestrations is disposed on at least one of the upper half and the lower half. The plurality of fenestrations is configured to facilitate selective expansion of at least one of the upper half or the lower half. The plurality of fenestrations is arranged in a first row containing a first subset of the plurality of fenestrations and a first arc containing a fourth subset of the plurality of fenestrations. The reconstruction support is bisected by a horizontal plane. The first arc is bisected by the horizontal plane. The horizontal plane separates the upper half from the lower half. The first row is contained within one of the upper half and the lower half.

BRIEF DESCRIPTION OF THE DRAWINGS

The details of one or more implementations are set forth in the accompanying drawings and the description below. Other features, aspects, and advantages of the disclosure will become apparent from the description, the drawings, and the claims, in which:

Figure 1:
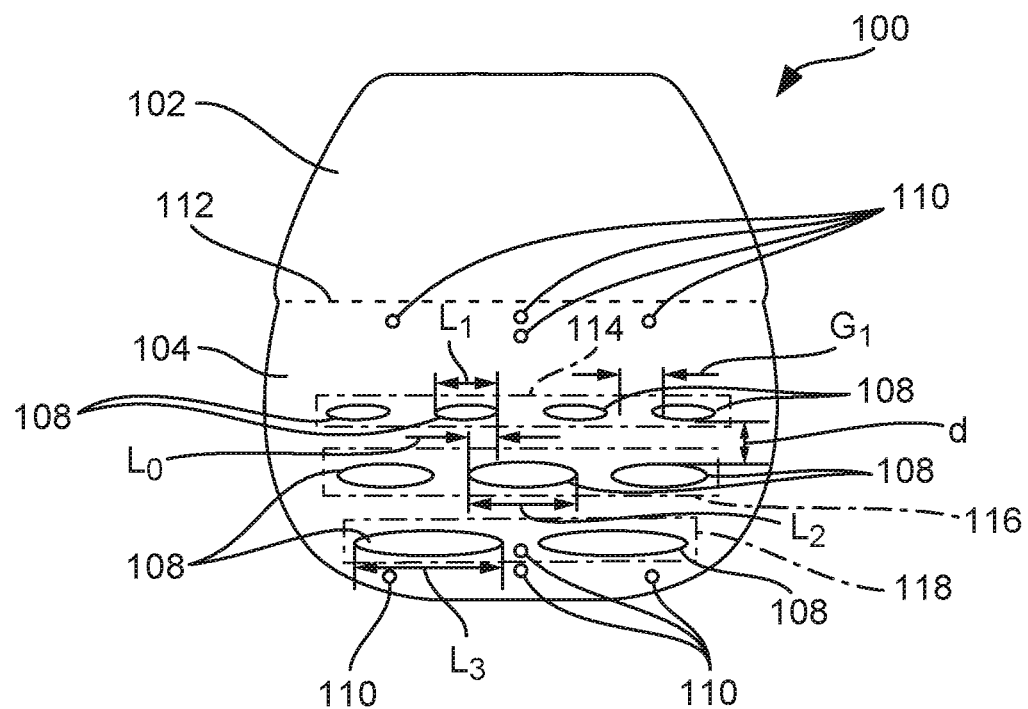
FIG. 1 is a top view of an example reconstruction support shown in a flat state.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

Following below are more detailed descriptions of various concepts related to, and implementations of, methods, apparatuses, and systems for using ADM fenestrations in prepectoral or subcutaneous breast reconstruction. The various concepts introduced above and discussed in greater detail below may be implemented in any of numerous ways, as the described concepts are not limited to any particular manner of implementation. Examples of specific implementations and applications are provided primarily for illustrative purposes.

I. Overview

ADMs and ATMs serve several important functions when utilized in breast reconstruction. For example, ADMs and ATMs provide relatively large soft tissue coverage over an implant by creating a precise implant pocket. The ADMs and ATMs also function to suspend the implant. These functions allow the ADMs and ATMs to provide improvements when used with several methods of breast reconstruction. For example, ADMs and ATMs may facilitate a decrease in completion time of a breast reconstruction. By decreasing the completion time, lower overall resource utilization may be achieved because patients may undergo fewer postoperative expansions and therefore require fewer office visits. In direct-to-implant reconstructions, the use of ADMs and ATMs may eliminate the need for any post-operative expansions.

The use of ADMs and ATMs may provide institutional savings by facilitating shorter operative times and more efficient use of office space during follow-up appointments. ADMs and ATMs may also lower an opportunity cost that is inherent to tissue-expander based breast reconstruction, thereby providing direct benefits to physicians. Patients typically experience less inconvenience during their recovery period when ADMs and ATMs are used and obtain an increased quality of life and satisfaction with the reconstruction and associated recovery. The use of ADMs and ATMs may, for example, require fewer office visits, decrease the time required to complete a reconstruction compared to conventional methods, require fewer drains that are placed and managed by a patient and physician, require drains to be placed for a shorter amount of time compared to conventional methods, provide increased control of the patient's anatomy (e.g., the inframammary fold, etc.), and other similar benefits.

When sutured to the chest wall, ADMs and ATMs can improve the symmetry and aesthetics of breast reconstruction, which are often important to patient satisfaction with the reconstruction. ADMs and ATMs have inherent stretch properties that confer elasticity and function similarly to normal intact human skin (e.g., in an unmodified form, etc.). Due to these properties, ADMs and ATMs may function as an expandable support (e.g., sling, etc.) at the medial, lateral, and inferior aspects of the reconstructed breast to support the weight of the implant. By decreasing tension on the implant, the ADMs and ATMs may permit full expansion of the lower pole, the medial extent, and the lateral extent of the implant pocket. Implant projection in each of those areas may be maximized resulting in a more aesthetically pleasing breast shape.

Recently, partial subpectoral (i.e., beneath the pectoralis major muscle) placement of tissue expanders and implants has been established as a common method of implant based breast reconstruction. ADMs and ATMs have been increasingly utilized to support, as well as cover, the implant at the inferolateral portion of the reconstruction pocket. Placement of the implant or tissue expander in the prepectoral plane (i.e., above the pectoralis major muscle) and coverage of the implant with the ADMs and/or ATMs (i.e., anteriorly and/or posteriorly) has been increasingly practiced. Some benefits of this method include less morbidity (i.e., the pectoralis major muscle is not elevated) which results in less postoperative patient discomfort, more rapid return to a patient's pre-surgical level of function, and minimizing of animation deformity.

This new approach requires a new ADM and/or ATM design which is not currently available. Previously proposed designs require multiple drains for facilitating fluid drainage and are undesirable. For example, previously proposed designs may require drains on a first pocket created between the native tissue and the ADMs and/or ATMs and on a second pocket created between the implant and/or implants and the ADMs and/or ATMs. Previously proposed designs also require the use of more ADMs and/or ATMs to achieve full coverage of the implants resulting in increased cost associated with the reconstruction.

ADMs and ATMs may be modified with fenestrations and egress perforations. For example, ADMs and ATMs may be modified with fenestrations and egress perforations for subpectoral, dual plane, or partial subpectoral designs. By modifying ADMs and ATMs with fenestrations, less of the ADMs and ATMs may be required to cover the surface of an implant and expander, thereby lowering the cost of breast reconstruction where ADMs and ATMs modified with fenestrations are employed. Modification of ADMs and ATMs with fenestrations also provides the ADMs and ATMs with the capability to attain a contoured form advantageous in the reconstruction of a breast. These modified designs may facilitate increased expansion of the lower pole, increased implant support, and improved aesthetics. Additionally, ADMs and ATMs modified with fenestrations and egress perforations may facilitate more precise coverage of an implant and more desirable medial, lateral, and inferior support of the implant. The fenestrations, with or without the egress perforations, facilitate an ability of the ADMs and ATMs to achieve a desirable shape (e.g., natural shape of a breast, teardrop shape, etc.), effacement (e.g., to an underlying tissue, against the breast flap and subcutaneous tissue, etc.), desirable expansion (e.g., expansion of the implant within the breast, etc.), desirable reconstruction (e.g., a faster reconstruction, a faster healing time, etc.), desirable fluid egress (e.g., from the tissue, etc.), decreased pain (e.g., due to less pull on native tissue during expansions, etc.), decreased discomfort (e.g., due to a single drain and not multiple drains, due to less need for an expansion process in the office, etc.), and increased drainage (e.g., through the use of less drains than are required when utilizing ADMs or ATMs without fenestrations or egress perforations, etc.).

In prepectoral reconstruction, ADMs and ATMs modified with fenestrations and egress perforations may be placed above chest muscle to substantially cover (e.g., fully cover, etc.) the implants. For example, the ADMs and ATMs modified with fenestrations and egress perforations may cover the implants anteriorly and posteriorly. ADMs and ATMs utilized in prepectoral reconstruction also decrease pain and animation deformity experienced by a patient after an operation has been completed. Modification of the ADMs and ATMs with fenestrations may further decrease pain experienced by a patient after an operation has been completed (e.g., due to less pull on native tissue, due to fastener expansion, etc.). Animation deformity may occur in non-prepectoral reconstruction. Animation deformity may manifest in a reconstructed breast that appears asymmetrical or not aesthetically pleasing.

Previously proposed designs fail to realize and utilize benefits associated with modifying ADMs and ATMs with fenestrations and egress perforations in the prepectoral plane. Further, previously proposed designs have not established or described a specific or universal design of ADMs and/or ATMs that is used to create the shape (e.g., tear drop shape, etc.) of a natural breast. ADMs and ATMs modified with fenestrations and egress perforations facilitate a more natural suspension of an implant or expander causing a reconstructed breast to be more symmetrical and aesthetically pleasing. Furthermore, when utilized in prepectoral breast reconstruction, there is an inherent decrease in potential animation deformity, which also lends to the improved aesthetics of a breast reconstructed using ADMs and/or ATMs. As a result, previously proposed designs are inferior and undesirable compared to designs that implement ADMs and/or ATMs modified with fenestrations and egress perforations.

II. Overview of Example Prepectoral Design

Figure 2:
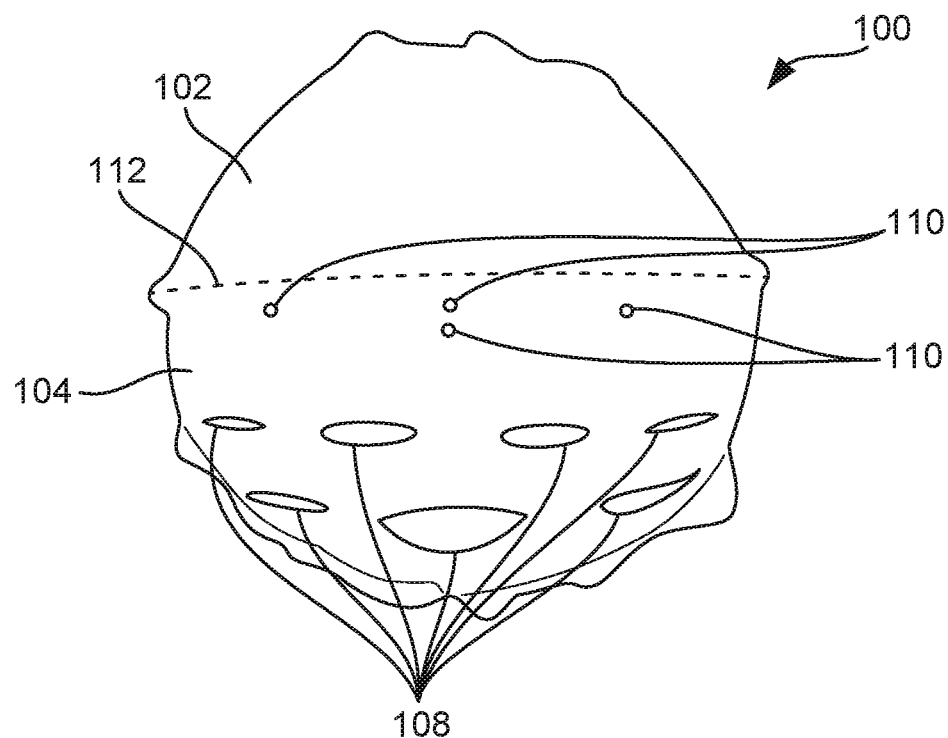
FIG. 2 is a top view of the reconstruction support of FIG. 1 in a rounded state.
Figure 3:
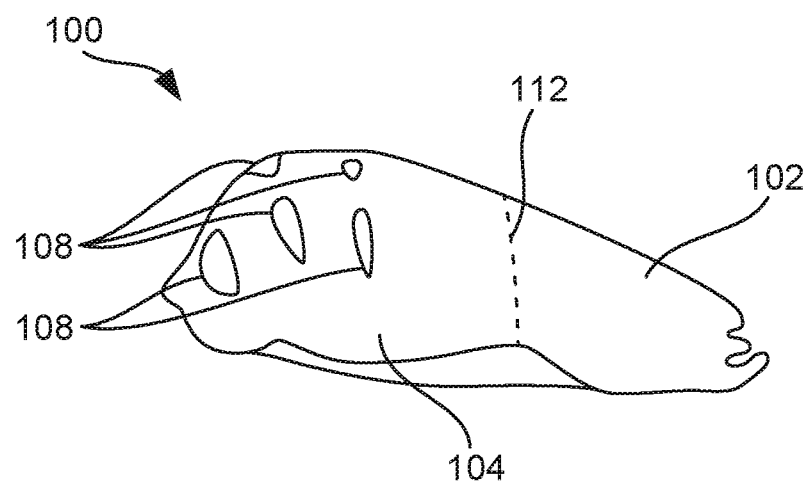
FIG. 3 is a side view of the reconstruction support of FIG. 1.

FIGS. 1-3 illustrate a reconstruction support 100. The reconstruction support 100 is placed in a prepectoral location and may be used to cover and support an implant (e.g., smooth implant, textured implant, round implant, shaped implant, expander type implant, saline implant, silicone implant, etc.) or tissue expander. In various embodiments, the reconstruction support 100 is utilized to support an implant or tissue expander having a volume of between 125 milliliters (mLs) and 800 mLs, inclusive. The reconstruction support 100 may be utilized in implant-based breast procedures such as breast reconstruction (e.g., two-stage breast reconstruction, etc.) and aesthetic implant-based augmentation. In some applications, the reconstruction support 100 may be sewn to the pectoral major fascia superiorly medially and laterally, then to serratus anterior laterally and the inframammary fold inferiorly. For example, the reconstruction support 100 may be located on a plane that is above all chest muscle, such that the muscle does not need to be lifted. In this way, the reconstruction support 100 facilitates above muscle breast reconstruction (AMBR).

The reconstruction support 100 includes an upper half 102 and a lower half 104. The upper half 102 and the lower half 104 are placed in a pre-pectoral pocket (e.g., a recently resurrected and used prepectoral pocket, etc.) during breast reconstruction. According to various embodiments, the upper half 102 and the lower half 104 are constructed from ADM and/or ATM. In some embodiments, the upper half 102 and the lower half 104 are separate panels which are joined (e.g., sewn, etc.) along a seam 112 to form the reconstruction support 100. In these embodiments, the upper half 102 is contiguous with the lower half 104 along the seam 112. These embodiments may be useful where a target size of the reconstruction support 100 is best attained through the combination of the upper half 102 have a first size and the lower half 104 having a second size. In other embodiments, the reconstruction support 100 is a single panel, and the upper half 102 is contiguous with, and integrated with, the lower half 104. In these embodiments, the reconstruction support 100 does not require any additional sewing.

The reconstruction support 100 maximizes the natural shape of an underlying breast and allows for full ADM and/or ATM coverage over the anterior surface of the implant without distorting the overall breast shape. As used herein, anterior includes borders of the implants superiorly, medially, laterally, and inferiorly. This reconstruction support 100 provides several advantages over previously proposed designs. For example, the reconstruction support 100 covers the full anterior surface (e.g., the tear drop shape, etc.) of the breast as opposed to only the inferior-lateral aspect, as is the case with the partial sub-muscular reconstruction. In this way, the reconstruction support 100 may optimize a reconstructed breast shape. Further, the reconstruction support 100 supports the implant, which decreases pressure on the skin envelope and results in less skin necrosis.

The reconstruction support 100 also eliminates dead space inherent in previously proposed designs and facilitates better effacement of ADM and/or ATM to a subcutaneous breast flap for faster neovascularization. The reconstruction support 100 also facilitates the use of a single drain (i.e., a single subcutaneous drain above the upper half 102 and/or the lower half 104) as opposed to the required use of multiple drains for previously proposed designs. The reconstruction support 100 may also provide universal coverage of all implant sizes and minimal, or virtually no, animation deformity. The reconstruction support 100 may also facilitate faster recovery for a patient, better aesthetics, and less patient discomfort.

As shown in FIG. 1, the lower half 104 includes a plurality of fenestrations 108 (e.g., windows, openings, apertures, etc.). The fenestrations 108 are strategically placed and facilitate more successful incorporation of the reconstruction support 100 into surrounding tissue. The fenestrations 108 may improve aesthetic results of breast reconstruction, decrease post-operative surgical pain, decrease animation deformity, and mitigate certain risks associated with implant based breast reconstruction. The fenestrations 108 may be, for example, aligned in successive rows and/or columns. The fenestrations 108 may also be organized in various symmetrical and asymmetrical patterns. As explained in more detail herein, the fenestrations 108 may be, for example, linear, radial, curvilinear, longitudinal, orthogonal, and oblique (e.g., having various degrees of obliquity, etc.).

Through the use of the fenestrations 108, the upper half 102 and/or the lower half 104 are capable of achieving additional expansion, via a decrease in the Young's modulus of the upper half 102 and/or the lower half. This additional expansion of the upper half 102 and/or the lower half 104 may be of particular importance over the portions of the implant subjected to gravity and native breast implant shape. In this way, the fenestrations 108 facilitate a more aesthetically pleasing and desirable reconstructed breast shape. The fenestrations 108 also facilitate a decrease in the amount of material needed in the upper half 102 and/or the lower half 104 to cover the entirety of the implant's anterior surface, thereby providing cost savings.

Furthermore, the fenestrations 108 facilitate faster expansion of tissue expanders in staged reconstructions or, alternatively, facilitate more direct to permanent implant (i.e., silicone or saline) reconstructions. Faster expansion of tissue expanders or direct to permanent implant reconstruction can preserve the natural beautiful lower pole and medial cleavage as well as the lateral shape of the breast. The fenestrations 108 facilitate additional fill in the expander, thereby minimizing dead space and leading to less complications (e.g., seroma, etc.).

The arrangement, shape, size, and number of the fenestrations 108 can be varied to provide various pliability (i.e., reduction in Young's Modulus) of the upper half 102 and/or the lower half 104. In this way, the reconstruction support 100 can be tailored to provide optimal effacement to native skin and subcutaneous fat for faster incorporation. Additionally, the fenestrations 108 facilitate fluid egress allowing for fewer drains and a lower seroma risk, improving patient comfort and lowering the overall complication risk associated with breast reconstruction.

The reconstruction support 100 facilitates more efficient surgeries (i.e., shorter operative times), decreasing risks to the patient from anesthesia, and other similar benefits. Ultimately, the reconstruction support 100 may provide institutional savings, a reduction in a surgeon's opportunity cost and office resource utilization, and increase patient comfort and satisfaction.

The reconstruction support 100 facilitates filling of a tissue expander at the time of immediate breast reconstruction for a two staged breast reconstruction, thereby leading to more direct to implant cases. This benefit of the reconstruction support 100 may be particularly advantageous in non-nipple sparing mastectomy cases.

The reconstruction support 100 may be utilized to cover an implant. The implant may be defined by an intra-operative fill volume. According to one embodiment, the reconstruction support 100 is capable of covering an implant with an intra-operative fill volume of approximately four hundred and fifty cubic centimeters (cm). In various embodiments, the reconstruction support 100 can be utilized with implants having a volume of between one hundred cubic centimeters and eight hundred cubic centimeters. The reconstruction support 100 may facilitate a fill of the implant equal to one-hundred percent of a total fill volume. The reconstruction support 100 may also facilitate the intra-operative fill volume of the implant equaling approximately ninety percent of a tissue expander size.

Through the use of the reconstruction support 100, approximately ninety-five percent of partial subpectoral reconstructions are either direct to implant or the tissue expander achieves nominal fill, in some applications. This decreases opportunity cost with less filling needed in the office, improves institutional savings, and improves the reconstruction experience for the patient as well. ADM fenestration, such as through the fenestrations 108, has been found to be beneficial in decreasing capsular contracture in a small study with over 13 months of follow up. With other data supporting decreased capsular contracture rates with ADM use in breast reconstruction, there has been a recent surge in implant based breast reconstruction in the prepectoral (i.e., subcutaneous) plane. This includes using titanium mesh, vicryl mesh, porcine and human ADM where they provide either anterior coverage or fully wrap the implant or expander.

A retrospective review of 10 patients (18 breasts) having undergone direct to implant and two-stage breast reconstruction utilizing fenestrated shaped ADM in the prepectoral or subcutaneous pocket was performed. The demographics of these patients are shown in Table 1. The review showed that sixteen breasts (89%) underwent direct to implant and two breasts (11%) received tissue expanders. All reconstructions were performed with FlexHD Pliable ADM with surgeon designed fenestrations (10 with FlexHD Pliable MAX 8×16 cm as part of the design and 8 with shaped fenestrated FlexHD Pliable 16×20 cm). Average intra-operative fill volume measured 450 cc, and intra-operative fill volume as a percent of tissue expander size averaged 90%. Intra-operative fill volume as a percentage of total fill volume at completion of expansion averaged 90%. The average time to final fill of expanders was 21 days.

TABLE 1

Demographics of patients in the retrospective review.

| | |
|---|---|
| Average age | 49 |
| Average body mass index (BMI) | 27.6 |
| Number of patients that are smokers | 0 |
| Number of patients with diabetes | 0 |
| Number of patients subject to neoadjuvant chemotherapy | 3 (30%) |
| Number of patients subject to adjuvant chemotherapy | 6 (60%) |
| Number of patients subject to radiation | 1 (10%) |

Two-stage reconstruction patients underwent one post-operative expansion on average and averaged 50 cc per in-office expansion. Days to full expansion averaged 21 days, while days to exchange averaged 87 days. The major complication rate requiring re-operation within 90 days post-operatively was 22.2% (four breasts). Three breasts (16.7%) were due to partial mastectomy flap necrosis resulting in 75% implant salvage in total. One breast (5.5%) underwent explantation due to infection. There was no seroma or capsular contracture in this study. Follow up was typically within 3.5-10 months.

TABLE 2

Details associated with reconstruction processes utilizing the reconstruction support 100 in the retrospective review.

| | |
|---|---|
| Number of patients | 10 |
| Total number of breasts reconstructed | 18 |
| Pre-operative ptosis (Regnalt classification) | 2.75 |
| Average pre-operative sternal notch to nipple distance | 22.8 cm |
| Average resection size | 318.6 grams |
| Number of direct to implant breasts | 16 |
| Number of breasts where a tissue expander was used | 2 |
| Average final implant size | 544.4 cc (±137.2 cc) |
| Average tissue expander size | 450 cc |
| Number of post-operative fills | 1 |
| Average post-operative fill volume | 50 cc |
| Average intraoperative fill volume | 450 cc |
| Ratio of intraoperative fill volume to tissue expander size | 90% |
| Number of days until full expansion | 21 |
| Average number of days until drain is removed | 9.3 |
| Average length of follow-up | 6.2 |

The review showed that the reconstruction support 100 improves breast shape, allows for faster expansion and more direct to implant reconstructions, requires less ADM to cover the same area resulting in reduced cost, faster operative procedures, improved fluid egress, use of one drain, and other similar benefits as outlined herein. This adds to the established advantages of prepectoral reconstruction, such as less functional deficits, no animation deformity, more natural breast shape, less pain, faster operations and shorter recovery, making it a very powerful tool in breast reconstruction.

Complications are fewer as there is less seroma risk due to a reduction in dead space from increased fill volume or an increased incidence of direct to implant reconstructions, not to mention there is only one dissected pocket instead of two. Also, there is improved blood supply to the breast flaps resulting from the preservation of the medial row of internal mammary perforators with this technique. There are some obvious challenges to a prepectoral implant based breast reconstruction. For example, there may be more rippling, an increased unexpected revisions, more tension on the breast flaps, and there may be the need for thick breast flaps and the need for an ideal breast size (small-medium). There also may be added expense, especially with full wraps.

TABLE 3

Complications experience in the retrospective review.

| | |
|---|---|
| Number of breasts that had major complications requiring re-operation | 4 (22.2%) |
| Number of breasts that suffered from an infection | 1 (5.6%) |
| Number of breasts that suffered from mastectomy flap necrosis | 3 (16.6%) |
| Number of breasts that suffered implant loss | 1 (5.6%) |
| Number of breasts that suffered from capsular contracture | 0 |
| Number of breasts that suffered from hematoma | 0 |
| Number of breasts that suffered from seroma | 0 |

TABLE 4

Secondary procedures utilized in the retrospective review.

| | |
|---|---|
| Number of breasts that underwent fat grafting | 3 |
| Average volume of grafted fat | 146.7 cc (±30.6 cc) |
| Number of breasts for which capsulorrhaphy for implant malposition was utilized | 2 |

As shown in FIG. 1, the lower half 104 also includes a plurality of alignment perforations 110. The alignment perforations 110 are utilized to facilitate placement and/or alignment of the reconstruction support 100 within the breast pocket. Through the use of the alignment perforations 110, the reconstruction support 100 may facilitate more precise placement and more consistent results than previously proposed devices. For example, the alignment perforations 110 may mitigate concerns of a surgeon as to the fenestrations 108 being potentially exposed in target locations associated with mastectomy incisions. Each of the alignment perforations 110 may be formed from a combination of shapes. For example, the alignment perforations 110 may be triangular. By changing the configuration of the alignment perforations 110, alignment of the reconstruction support 100 within the breast pocket may be easier for a target application. The alignment perforations 110 are positioned along (e.g., disposed upon, etc.) a perimeter (e.g., periphery, edge, etc.) of the reconstruction support 100. For example, the alignment perforations 110 may be positioned along a top edge of the upper half 102 and along a bottom edge of the lower half 104. In various embodiments, two alignment perforations 110 are aligned on a vertical plane symmetrically bisecting the reconstruction support 100 (e.g., from the upper half 102 to the lower half 104, etc.) and disposed on a top edge of the upper half 102 and/or two alignment perforations 110 are aligned on the vertical plane and disposed on a bottom edge of the lower half 104. Additional alignment perforations 110 may be positioned on either side (e.g., medial side, lateral side, etc.) of the two vertically aligned alignment perforations 110.

The alignment perforations 110 may be aligned in columns and/or rows, or may be organized in a symmetrical or asymmetrical pattern. The alignment perforations 110 may be arranged based on the locations of the fenestrations 108. As shown in FIG. 1, at least some of the alignment perforations 110 may be aligned (e.g., disposed, etc.) near (e.g., adjacent, etc.) the seam 112. In various embodiments, the alignment perforations 110 are circular and have a diameter of between 1-5 millimeters (mm), inclusive.

As shown in FIG. 1, the fenestrations 108 are arranged in a first row 114, a second row 116, and a third row 118. In this way, a first subset (e.g., group, collection, etc.) of the fenestrations 108 is contained (e.g., included, etc.) in the first row 114, a second subset of the fenestrations 108 is contained in the second row 116, and a third subset of the fenestrations 108 is contained in the third row 118. The first row 114, the second row 116, and the third row 118 are substantially parallel to the seam 112. Additionally, the first row 114 is substantially parallel to the second row 116 which is substantially parallel to the third row 118. The fenestrations 108 within the first row 114 may be staggered relative to the fenestrations 108 in the second row 116, and the fenestrations 108 in the second row 116 may be staggered relative to the fenestrations 108 in the third row 118. In this way, at least a portion of each of the fenestrations 108 in the second row 116 overlaps at least a portion of at least one of the fenestrations 108 in the first row 114 and at least a portion of at least one of the fenestrations 108 in the third row 118.

Each of the fenestrations 108 in the first row 114 has a first length $L_1$, each of the fenestrations 108 in the second row 116 has a second length $L_2$, and each of the fenestrations 108 in the third row 118 has a third length $L_3$. In an example embodiment, the first length $L_1$ is less than the second length $L_2$, and the second length $L_2$ is less than the third length $L_3$. In various embodiments, the first row 114, the second row 116, and the third row 118 are contained on the upper half 102 or the lower half 104. In various embodiments, the first length $L_1$, the second length $L_2$, and the third length $L_3$ are each between 12-31 millimeters (mm), inclusive.

The fenestrations 108 in adjacent rows define an overlap $L_O$. Depending on the lengths of the fenestrations 108 (e.g., the first length $L_1$, the second length $L_2$, the third length $L_3$, etc.) and the spacing between fenestrations 108 (e.g., the spacing between the fenestrations 108 in the first row 114, the spacing between the fenestrations 108 in the second row 116, the spacing between the fenestrations 108 in the third row 118, etc.), the overlap $L_O$ may be different. In various embodiments, the overlap $L_O$ is between 1-80% of the length of the fenestration 108 from which the overlap is measured. In other words, the reconstruction support 100 may be configured such that a fenestration 108 in the first row 114 overlaps a fenestration 108 in the second row 116 by between 1-80%, inclusive, of the length of the fenestration 108 in the first row 114.

The fenestrations 108 in a row (e.g., the first row 114, the second row 116, the third row 118, etc.) are separated by a first gap $G_1$ between adjacent fenestrations 108 in that row. In various embodiments, the first gap $G_1$ is between 6-28 mm, inclusive.

The fenestrations 108 in a row (e.g., the first row 114, the second row 116, the third row 118, etc.) are separated by a distance d from the fenestrations 108 of an adjacent row (e.g., the first row 114, the second row 116, the third row 118, etc.). In various embodiments, the distance d is between 8-24 mm, inclusive.

In some embodiments, the upper half 102 and/or the lower half 104 may be constructed from various allografts and ADMs and/or ATMs of various sizes. The fenestrations 108 facilitate virtually universal applicability of the reconstruction support 100 with various implants and tissue expanders used for breast reconstruction. For example, the upper half 102 and the lower half 104 may be constructed from FlexHD pliable ADM or FlexHD pliable MAX ADM. In other examples, the upper half 102 and/or the lower half 104 may be constructed from AlloDerm®, DermACELL (e.g., DermACELL AWM®, etc.), porcine ADM, synthetic mesh, and other similar materials.

The upper half 102 and the lower half 104 may be formed from ADMs and/or ATMs of various sizes. For example, the upper half 102 and the lower half 104 may be formed from eight centimeter by sixteen centimeter sheets of FlexHD pliable MAX ADM. In another example, the upper half 102 and the lower half 104 are formed from sixteen centimeter by twenty centimeter surgeon designed shaped fenestrated sheets of FlexHD pliable ADM. The upper half 102 and the lower half 104 may be formed by cutting ADM to shape and then cutting the fenestrations 108 to expand the medial, lateral, and inferior portion of the implant or expander.

In FIGS. 1-3, the upper half 102 is shown as formed from a six centimeter by sixteen centimeter FlexHD pliable MAX ADM and the lower half 104 is shown as formed from an eight centimeter by sixteen centimeter FlexHD pliable MAX ADM.

Figure 70:
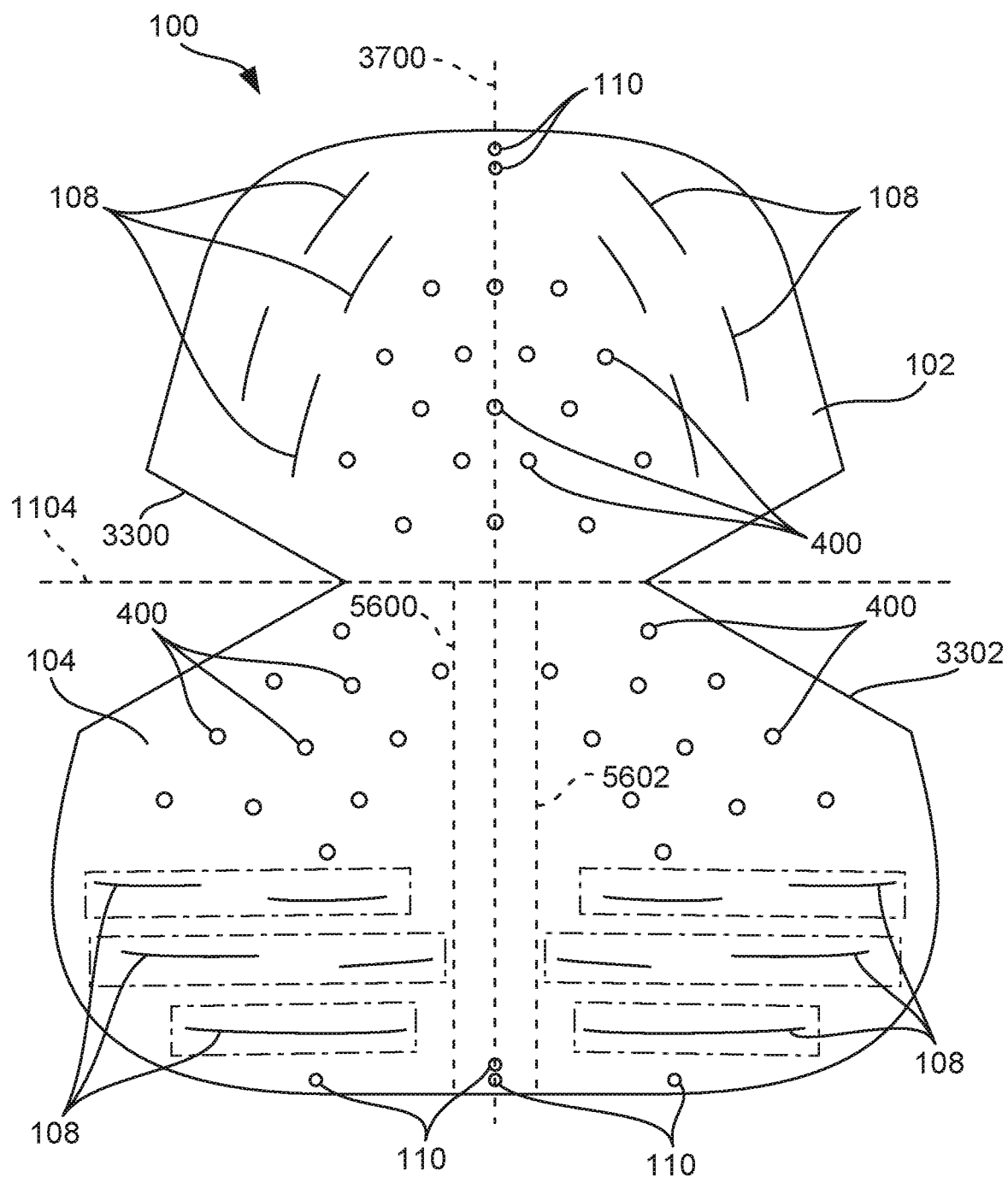
FIG. 70 is a top view of another example reconstruction support shown in a flat state and being constructed from a single piece of material.

FIGS. 1-70 illustrate the reconstruction support 100 is shown in various shapes, sizes, and configurations. The length of the fenestrations 108 may be varied depending on the application of the reconstruction support 100. For example, the length of the fenestrations 108 may be between 1-40 mm.

In FIGS. 4-14, both the upper half 102 and the lower half 104 include the fenestrations 108. In various embodiments, the lower half 104 includes a greater number of the fenestrations 108 than the upper half 102. In these embodiments, the lower half 104 is capable of expanding more than the upper half 102, due to the increased number of the fenestrations 108 in the lower half 104. Such embodiments may be advantageous where increased expansion of the reconstruction support 100 is required proximate the lower half 104. The upper half 102 is shown as formed from an eight centimeter by sixteen centimeter FlexHD pliable MAX ADM and the lower half 104 is shown as formed from an eight centimeter by sixteen centimeter FlexHD pliable MAX ADM.

Figure 4:
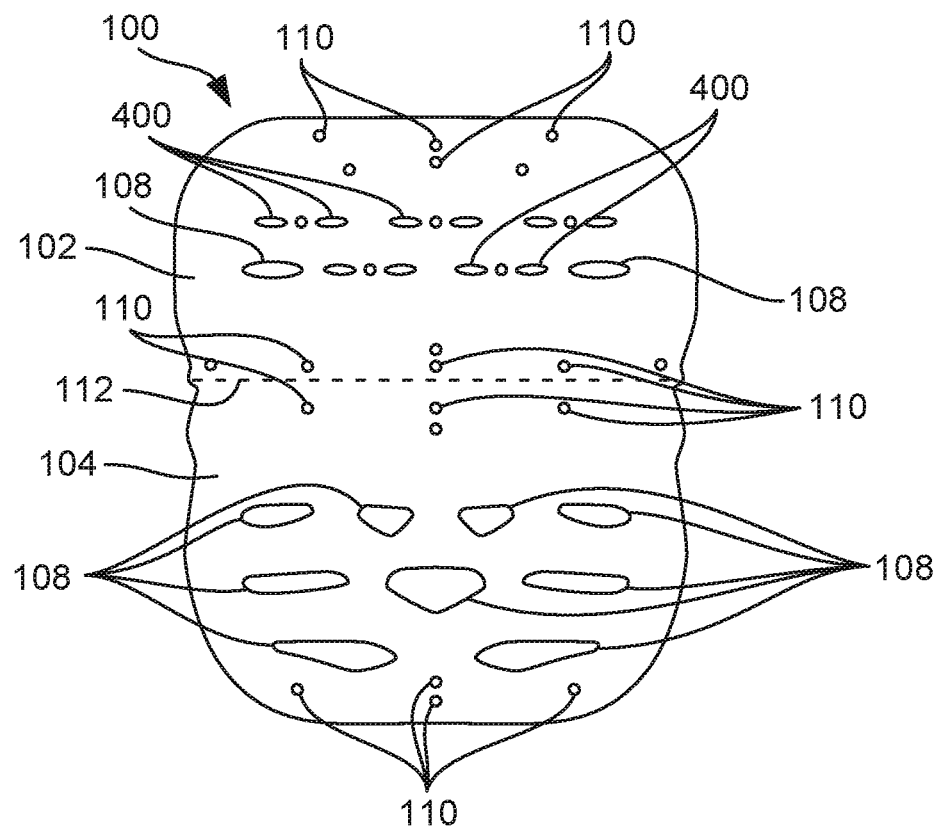
FIG. 4 is a top view of another example reconstruction support having fenestrations, the reconstruction support shown in a flat state.
Figure 5:
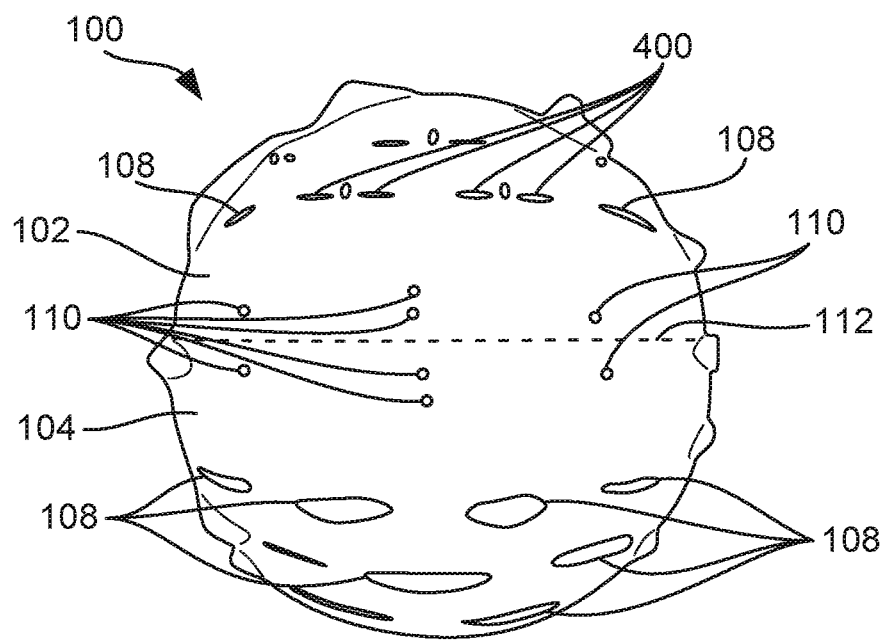
FIG. 5 is a top view of the reconstruction support of FIG. 4, the reconstruction support shown in a rounded state.
Figure 8:
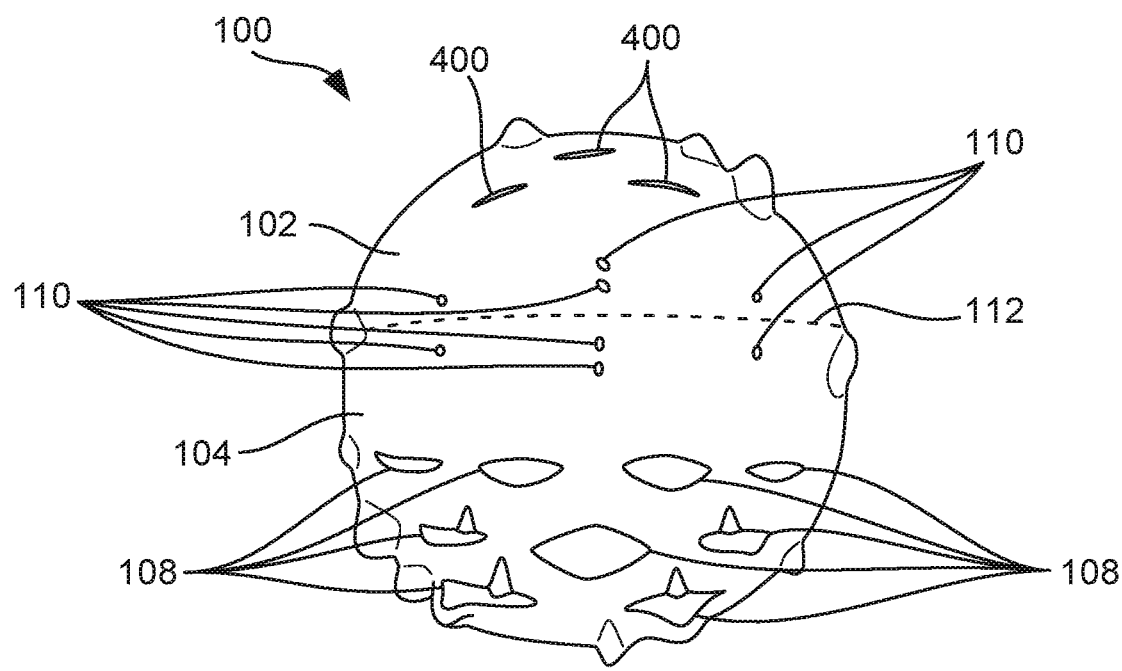
FIG. 8 is a top view of another example reconstruction support shown in a rounded state.

FIGS. 4, 5, and 8 illustrate embodiments where the reconstruction support 100 includes a plurality of egress perforations 400. The egress perforations 400 are independent of the alignment perforations 110. The egress perforations 400 may be included in the reconstruction support 100 in place of, or in addition to, the plurality of fenestrations 108. The egress perforations 400 can function as the fenestrations 108 and can, for example, facilitate improved fluid egress and decrease serum risk. The egress perforations 400 may improve aesthetic results of breast reconstruction, decrease post-operative surgical pain, decrease animation deformity, and mitigate certain risks associated with implant based breast reconstruction. Additionally, the egress perforations 400 may be utilized in the reconstruction support 100 for applications where use of the fenestrations 108 may be undesirable. For example, a surgeon may be more comfortable using the reconstruction support 100 if it includes the egress perforations 400, but not the fenestrations 108, in a target area (e.g., along the upper half 102, along the lower half 104, etc.). Like the fenestrations 108, the egress perforations 400 may be arranged in a plurality of columns and rows. The egress perforations 400 facilitate fluid egress but do not substantially change the Young's modulus of the reconstruction support 100. In this sense, substantially encompasses de minimus variations of 1%. In this way, the egress perforations 400 can be included in the reconstruction support 100 where a change in the Young's modulus of the reconstruction support 100 is not desired but where fluid egress is desired. In various embodiments, the egress perforations 400 are each generally circular and defined by a diameter of between 1-5 mm, inclusive. In an example embodiment, each of the egress perforations 400 is at least 5 mm from any of the fenestrations 108.

Figure 6:
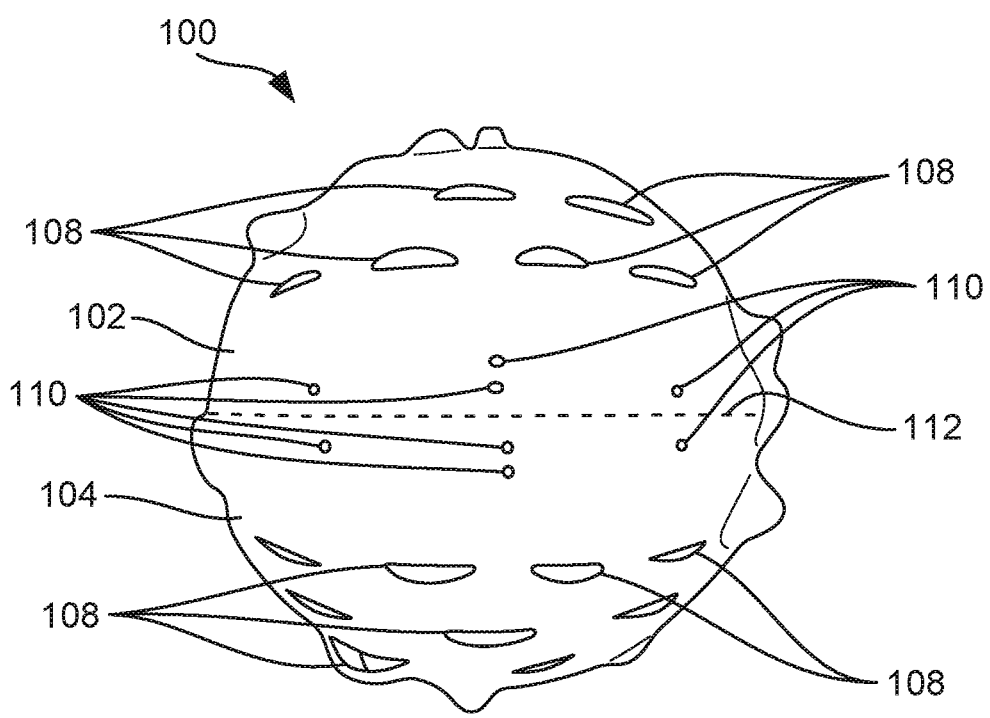
FIG. 6 is a top view of another example reconstruction support, the reconstruction support shown in a rounded state.
Figure 7:
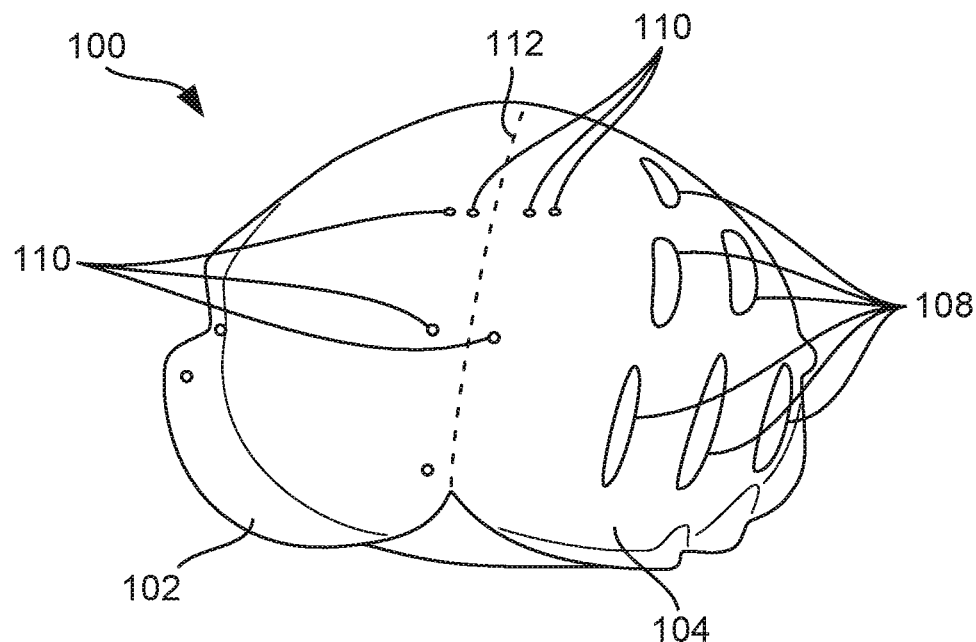
FIG. 7 is a side view of another example reconstruction support, the reconstruction support shown in a rounded state.

In some embodiments, an egress perforation 400 is formed by closing a fenestration 108. For example, a fenestration 108 may be sutured across the middle of the fenestration, thereby forming an egress perforation 400 on each side of the suture. In FIG. 5, the fenestrations 108 are shown closed to form a plurality of egress perforations 400. For example, the fenestrations 108 may be partially or completely sewn shut (e.g., with a stitch, etc.). In FIG. 6, the fenestrations 108 are shown open and are not sutured to create any of the egress perforations 400. It is understood that other similar variations are within the scope of the present disclosure.

Figure 9:
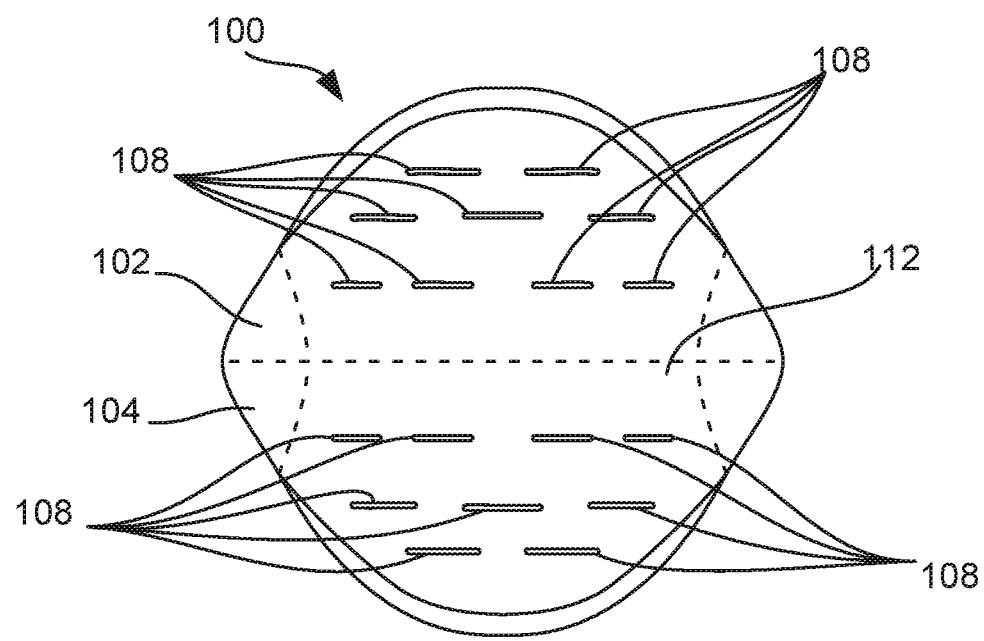
FIG. 9 is a top view of the reconstruction support of FIG. 9 in a flat state.
Figure 10:
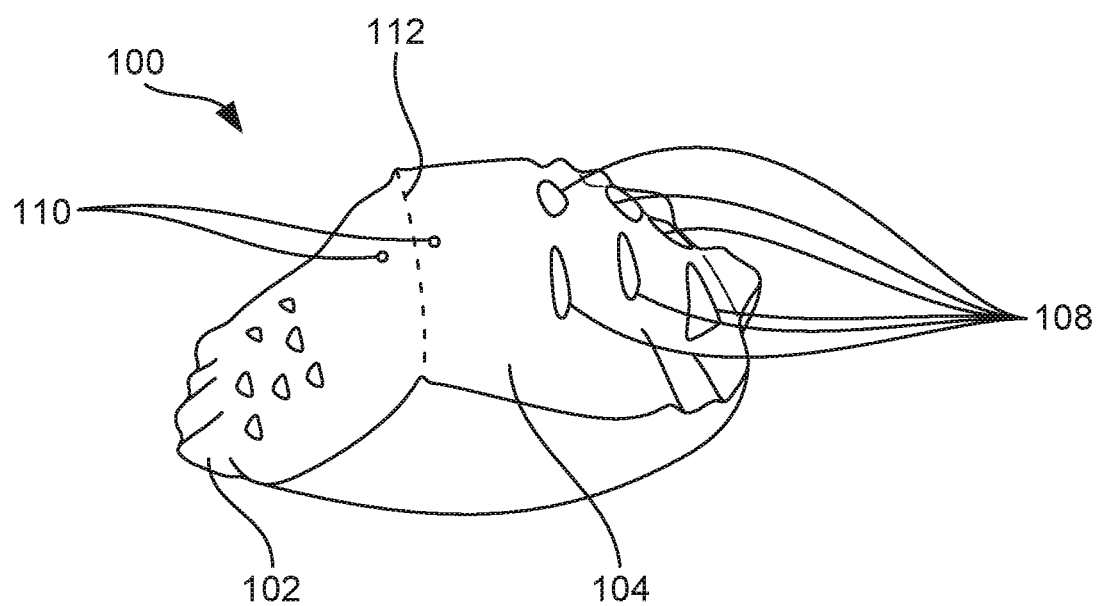
FIG. 10 is a side view of the reconstruction support of FIG. 9.

In FIGS. 8-10, the reconstruction support 100 is shown in a larger size, such as to accommodate implants that are four hundred and fifty cubic centimeters or larger. The upper half 102 and the lower half 104 are substantially hourglass shaped and include horizontal appliqués aligned on the seam 112 to accommodate the relatively larger implants. In FIGS. 9 and 10, both the upper half 102 and the lower half 104 are shown as integrated into a single panel that is shaped like a rounded pentagon (e.g., ovoid, tear drop shaped, oval shaped, egg shaped, etc.).

Figure 11:
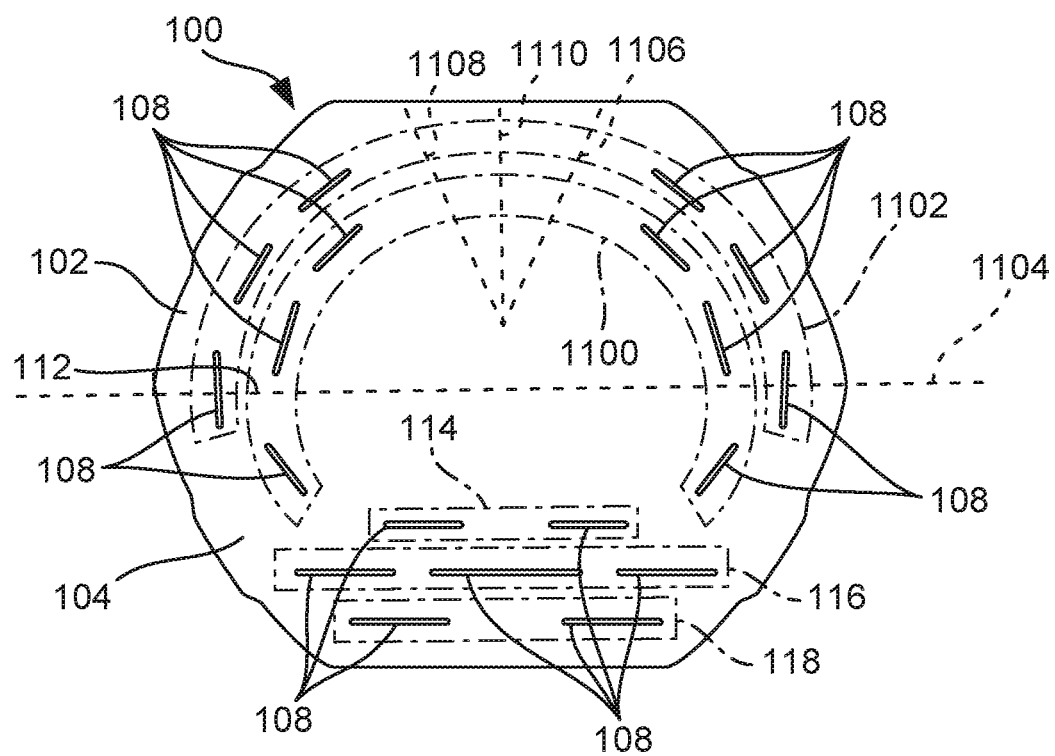
FIG. 11 is a top view of another example reconstruction support shown in a flat state, the reconstruction support having an adjustable slit and being constructed from a single piece of material.

In FIGS. 11-14, both the upper half 102 and the lower half 104 are shown as integrated into a single panel that is shaped like a rounded pentagon and formed from a sixteen centimeter by twenty centimeter FlexHD pliable ADM. As shown in FIG. 11, the fenestrations 108 are two centimeters or three centimeters long.

As shown in FIG. 11, the fenestrations 108 are arranged in the first row 114, the second row 116, and the third row 118, as well as a first arc 1100 and a second arc 1102. In this way, a fourth subset of the fenestrations 108 is contained in the first arc 1100 and a fifth subset of the fenestrations 108 is contained in the second arc 1102 in addition to the first subset of the fenestrations 108 contained in the first row 114, the second subset of the fenestrations 108 contained in the second row 116, and the third subset of the fenestrations 108 contained in the third row 118. The first arc 1100 and the second arc 1102 are substantially concentric (e.g., coaxial, have substantially the same central axis, are revolved about substantially the same point, etc.). The fenestrations 108 within the first arc 1100 may be staggered relative to the fenestrations 108 in the second arc 1102. In this way, at least a portion of each of the fenestrations 108 in the second arc 1102 overlaps at least a portion of at least one of the fenestrations 108 in the first arc 1100. Each of the fourth subset of the fenestrations 108 in the first arc 1100 and each of the fifth subset of the fenestrations 108 in the second arc 1102 may be straight or at least partially curved in shape.

Each of the fenestrations 108 in the first arc 1100 has a fourth length $L_4$ and each of the fenestrations in the second arc 1102 has a fifth length $L_5$. The fourth length $L_4$ is measured along the first arc 1100 and the fifth length $L_5$ is measured along the second arc 1102. In various embodiments, the fourth length $L_4$ is substantially equal to the fifth length $L_5$ and the first length $L_1$. In this way, the fourth length $L_4$ and the fifth length $L_5$ may be less than the second length $L_2$ and/or the third length $L_3$. The reconstruction support 100 is bisected by a horizontal plane 1104. In some embodiments, the reconstruction support 100 is substantially symmetrical about the horizontal plane 1104.

In various embodiments, at least a portion of at least one of the first arc 1100 and the second arc 1102 is bisected by the horizontal plane 1104 such that at least a portion of at least one of the first arc 1100 and the second arc 1102 is disposed on both the upper half 102 and the lower half 104 (e.g., extends from the upper half 102 onto the lower half 104, etc.). In some of these embodiments, the first row 114, the second row 116, and the third row 118 are contained on the upper half 102 or the lower half 104. In various embodiments, at least a portion of at least one of the first arc 1100 and the second arc 1102 is disposed on both the upper half 102 and the lower half 104 (e.g., extends from the upper half 102 onto the lower half 104, etc.). In some of these embodiments, the first row 114, the second row 116, and the third row 118 are contained on the upper half 102 or the lower half 104. In various embodiments, the first length $L_1$, the second length $L_2$, the fourth length $L_4$, and the fifth length $L_5$ are substantially equal to two centimeters. In some of these embodiments, the third length $L_3$ is substantially equal to three centimeters.

Figure 12:
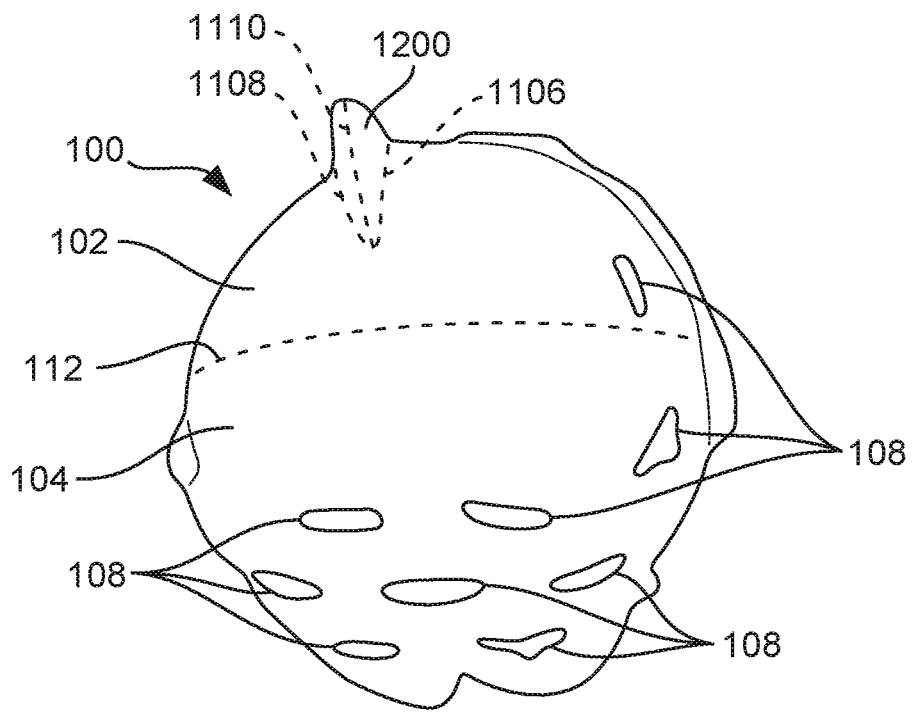
FIG. 12 is a top view of the reconstruction support of FIG. 11 in a rounded state, the adjustable slit utilized to tailor the reconstruction support.
Figure 13:
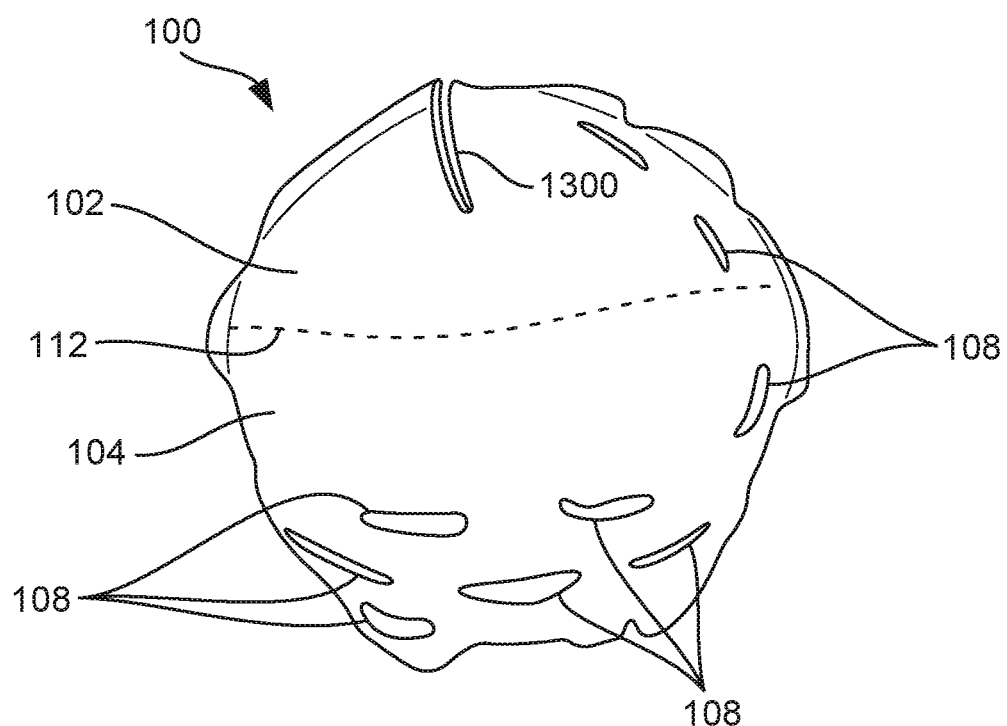
FIG. 13 is another top view of the reconstruction support of FIG. 11 in a rounded state, the adjustable slit not utilized to tailor the reconstruction support.
Figure 14:
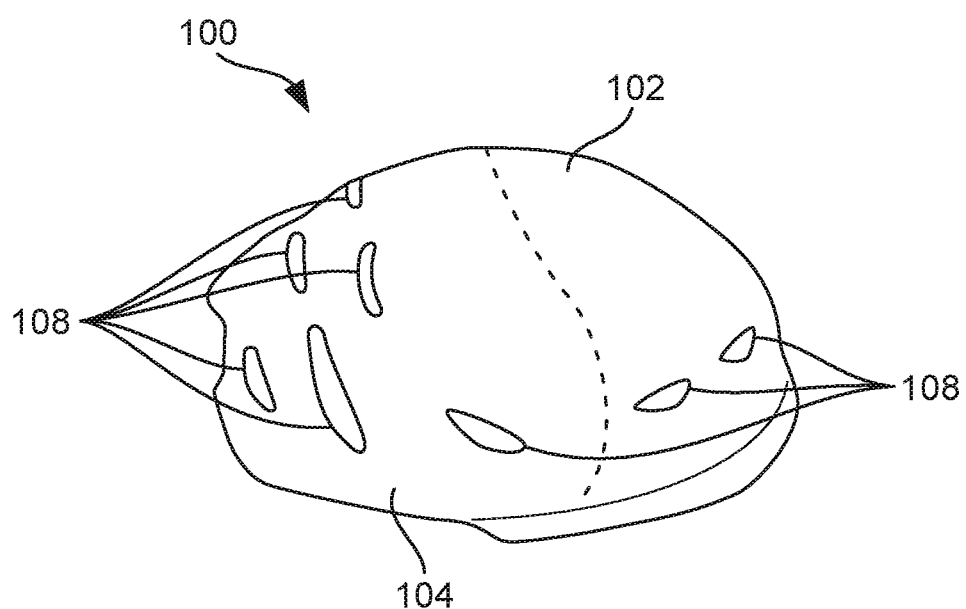
FIG. 14 is a side view of the reconstruction support of FIG. 11.
Figure 15:
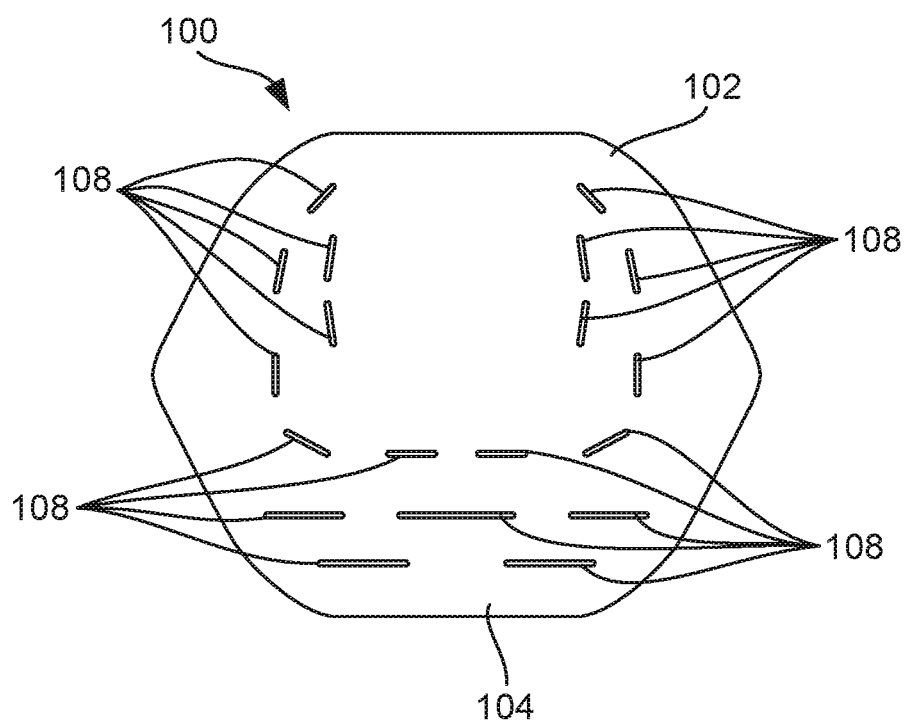
FIG. 15 is a top view of another example reconstruction support shown in a flat state and being constructed from a single piece of material.
Figure 16:
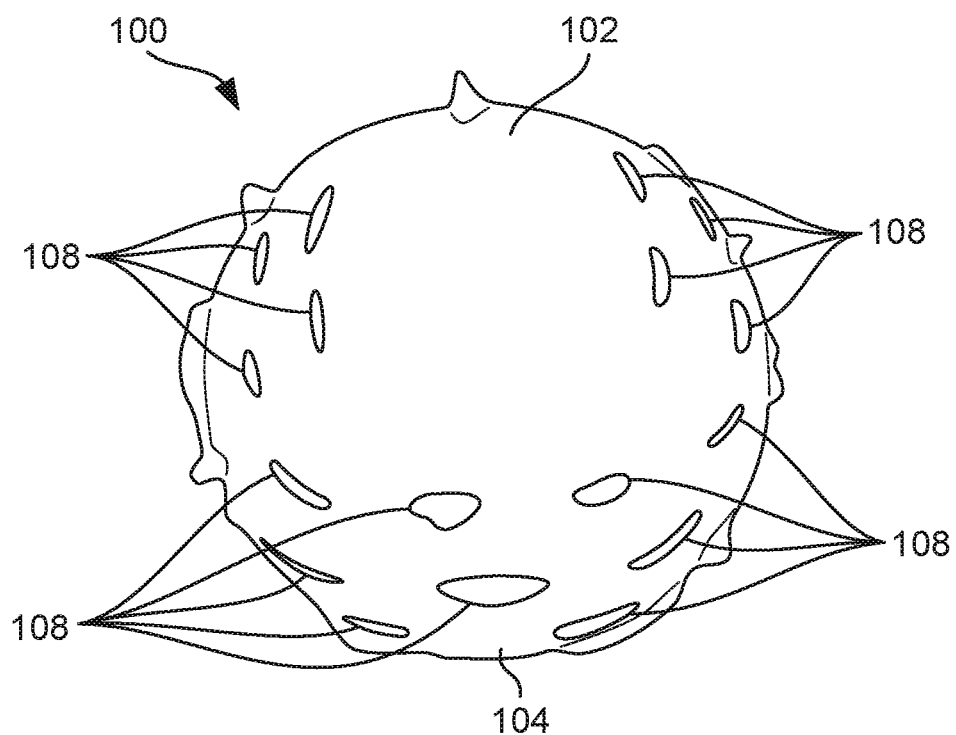
FIG. 16 is another top view of the reconstruction support of FIG. 15 in a rounded state.
Figure 17:
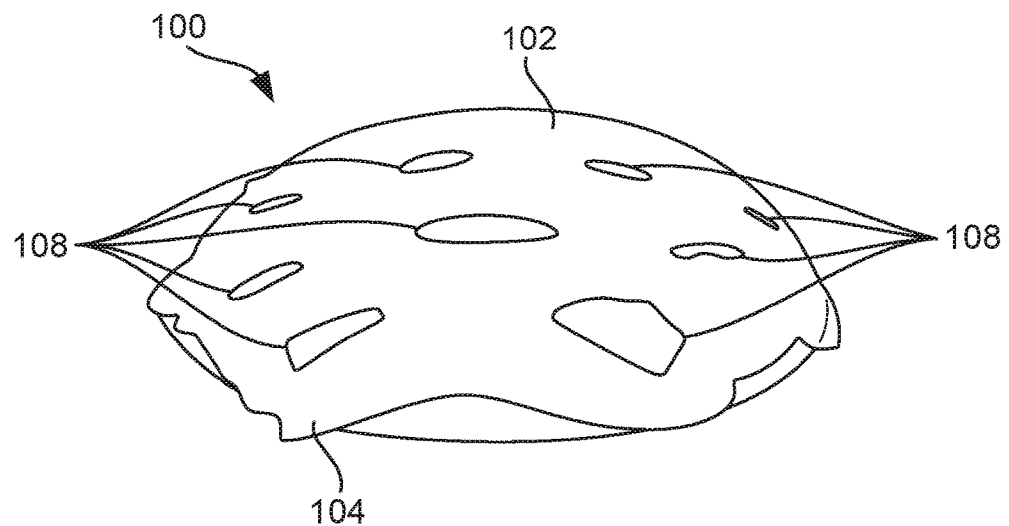
FIG. 17 is a front view of the reconstruction support of FIG. 15 in a rounded state.
Figure 18:
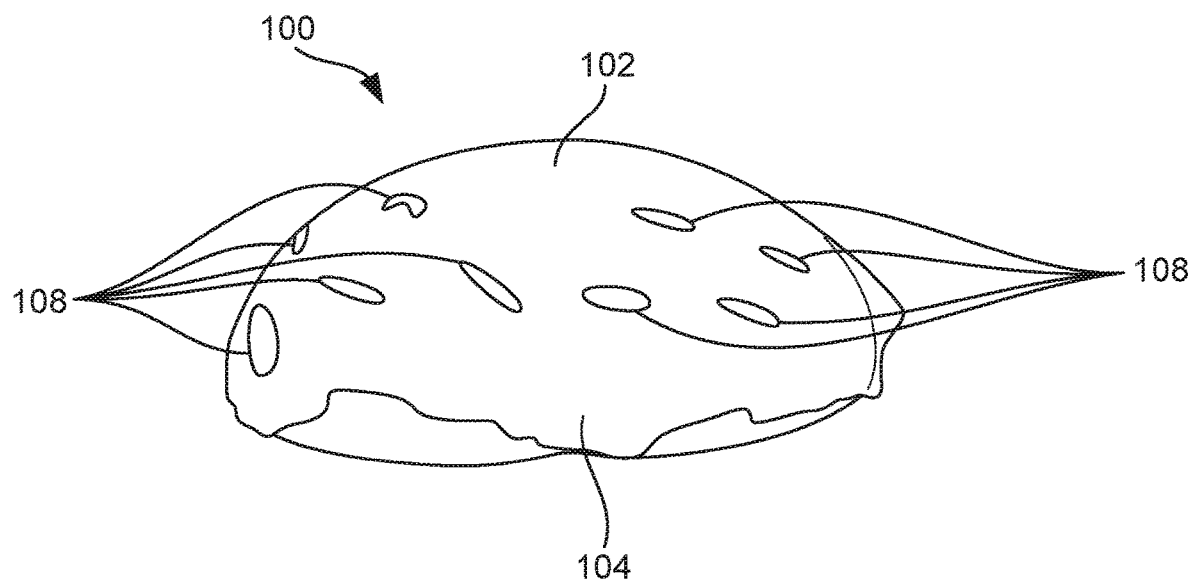
FIG. 18 is a side view of the reconstruction support of FIG. 15.
Figure 19:
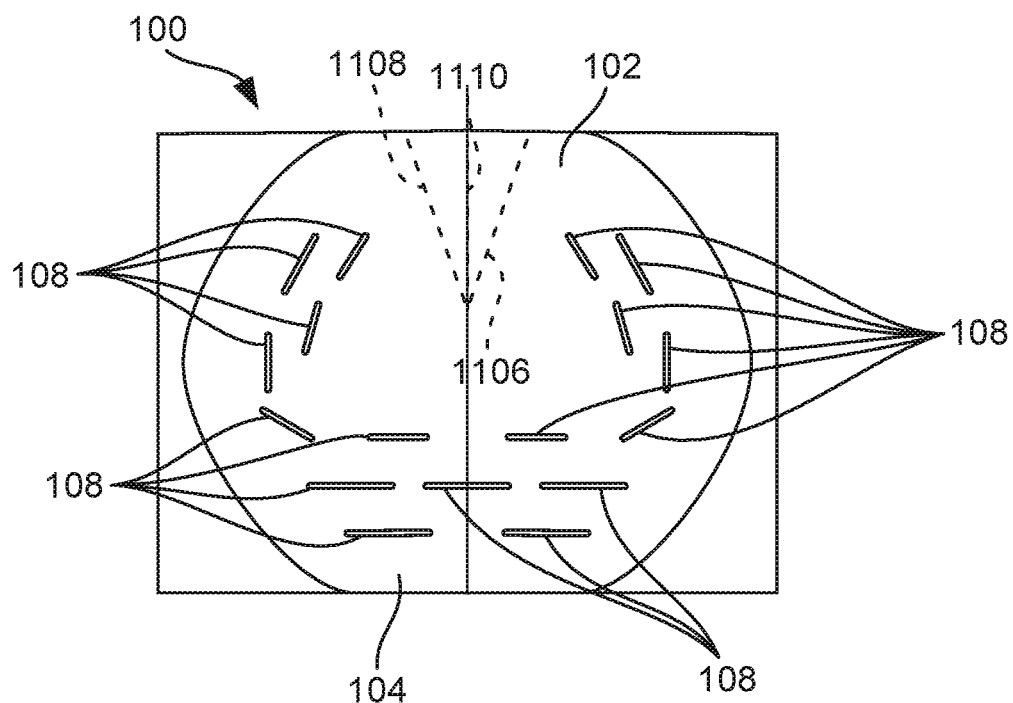
FIG. 19 is a top view of another example reconstruction support shown in a flat state and being constructed from a single piece of material.
Figure 20:
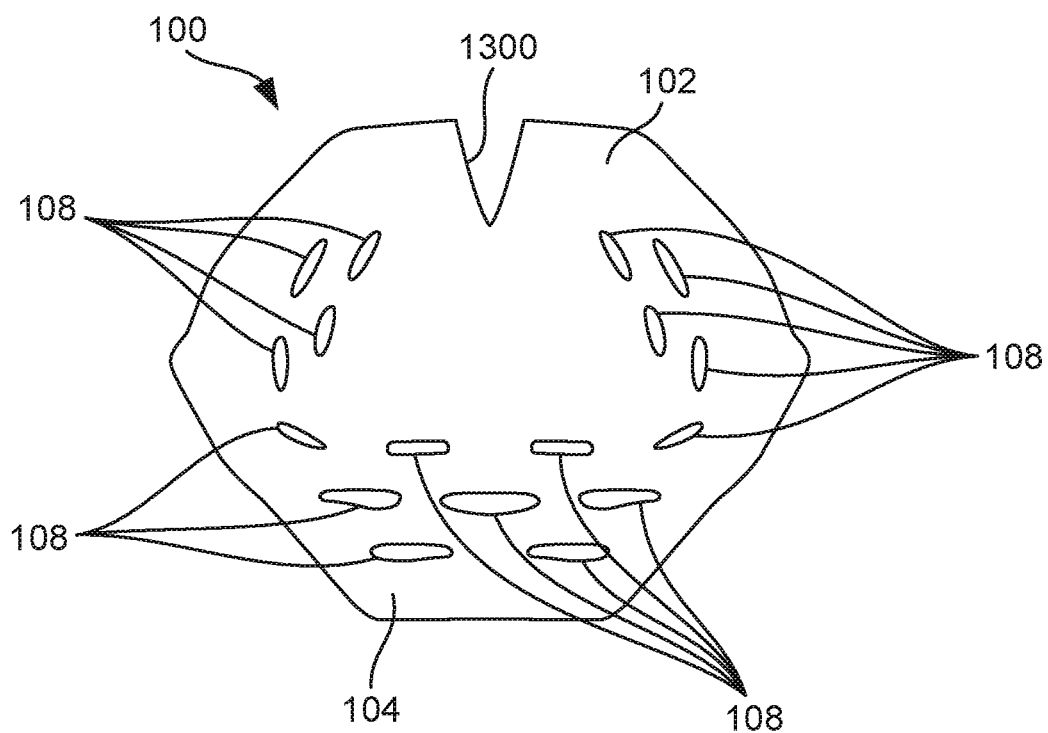
FIG. 20 is another top view of the reconstruction support of FIG. 19 in a flat state.
Figure 21:
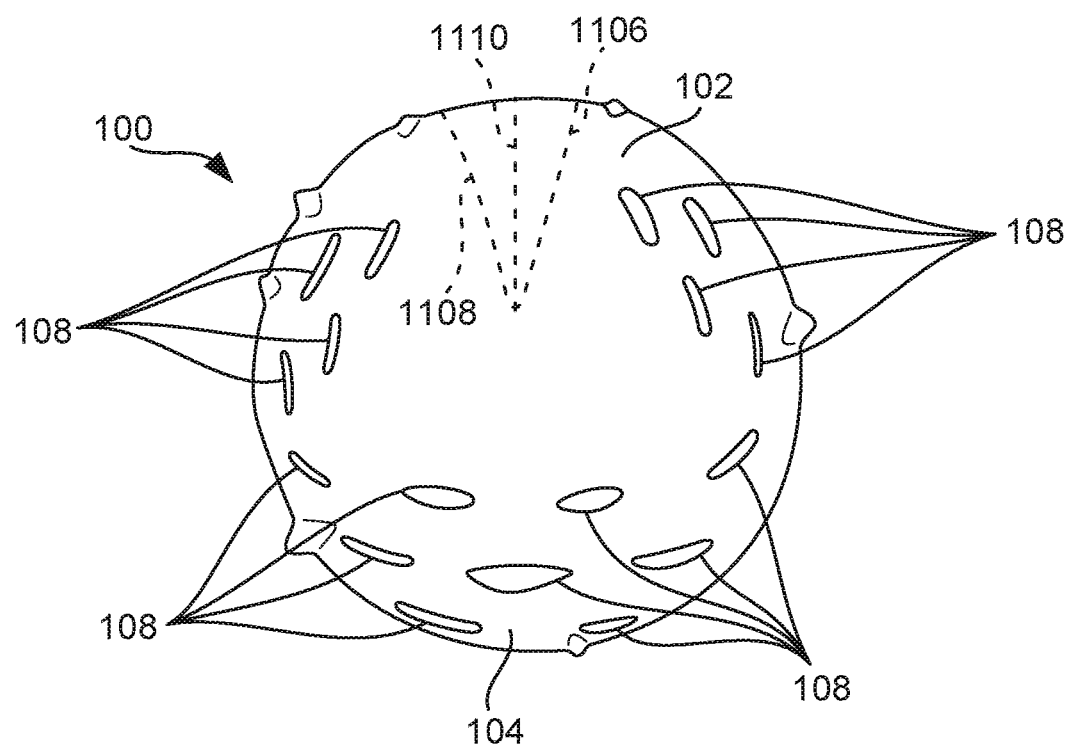
FIG. 21 is a top view of the reconstruction support of FIG. 19 in a rounded state.
Figure 22:
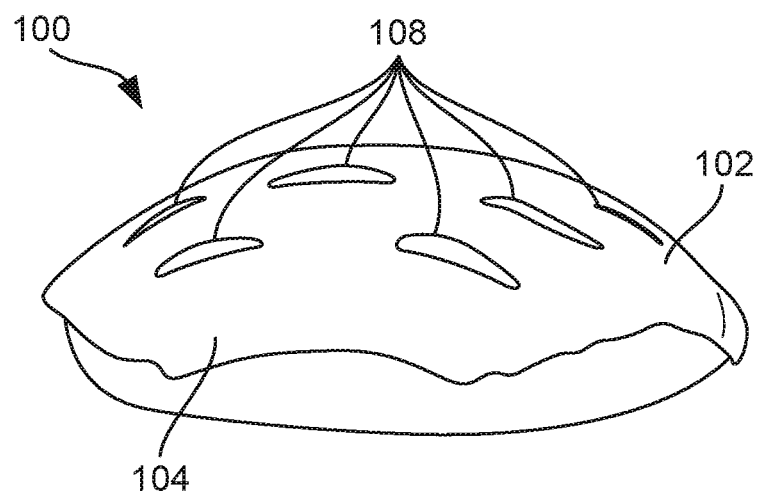
FIG. 22 is a front view of the reconstruction support of FIG. 19 in a rounded state.
Figure 23:
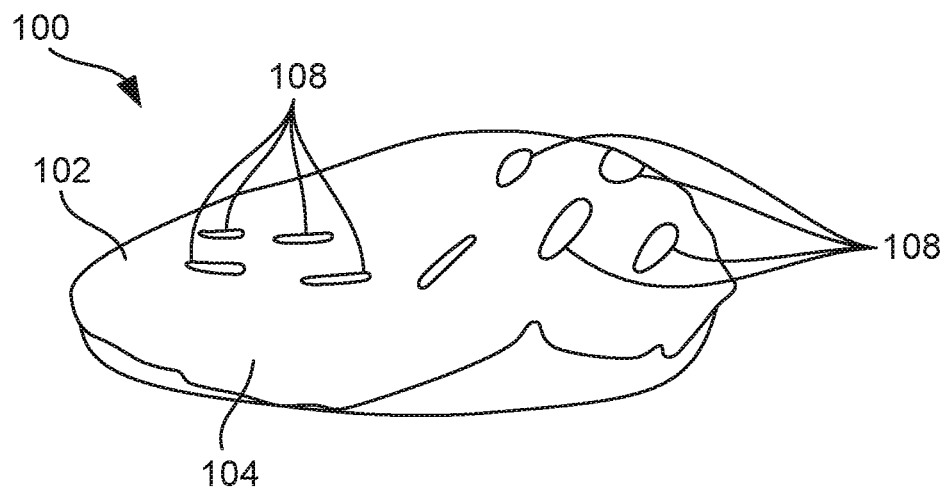
FIG. 23 is a side view of the reconstruction support of FIG. 19.
Figure 24:
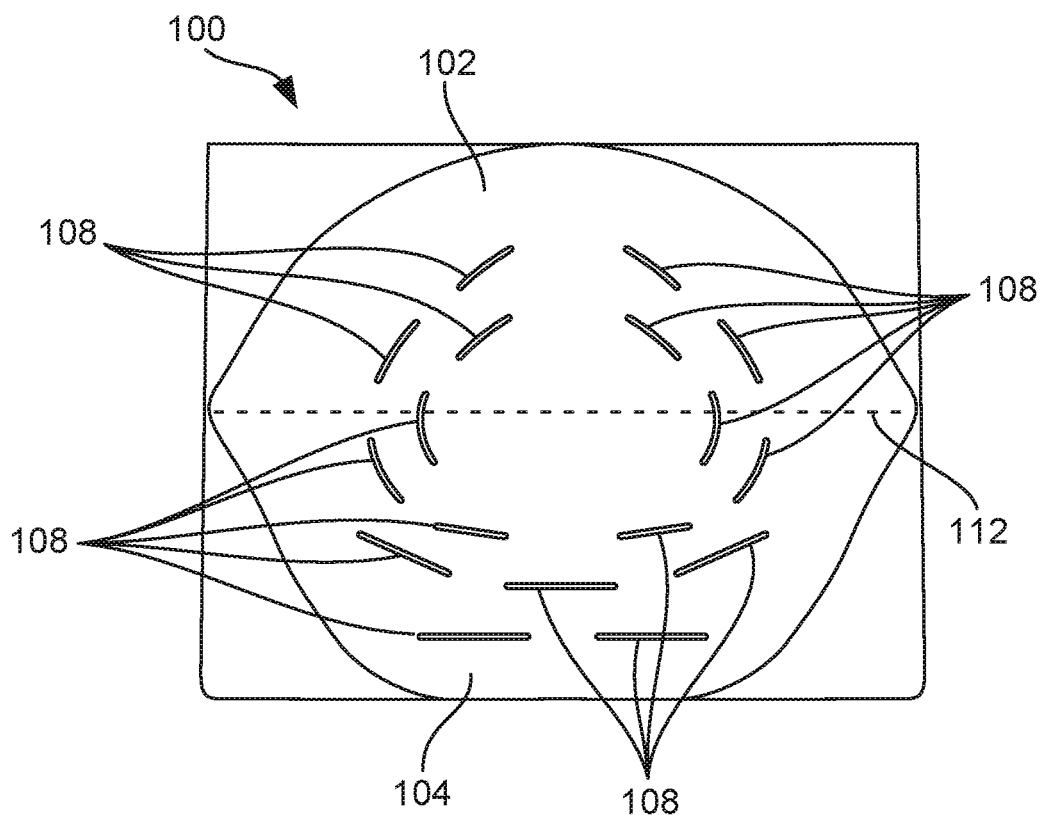
FIG. 24 is a top view of another example reconstruction support shown in a flat state and being constructed from a single piece of material.
Figure 25:
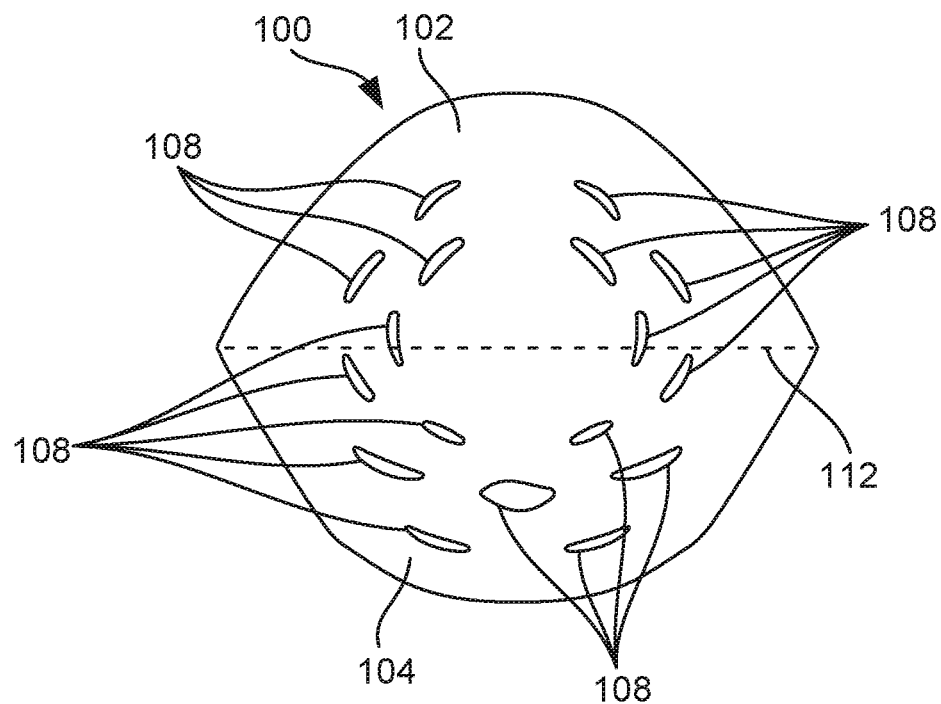
FIG. 25 is another top view of the reconstruction support of FIG. 24 in a flat state.
Figure 26:
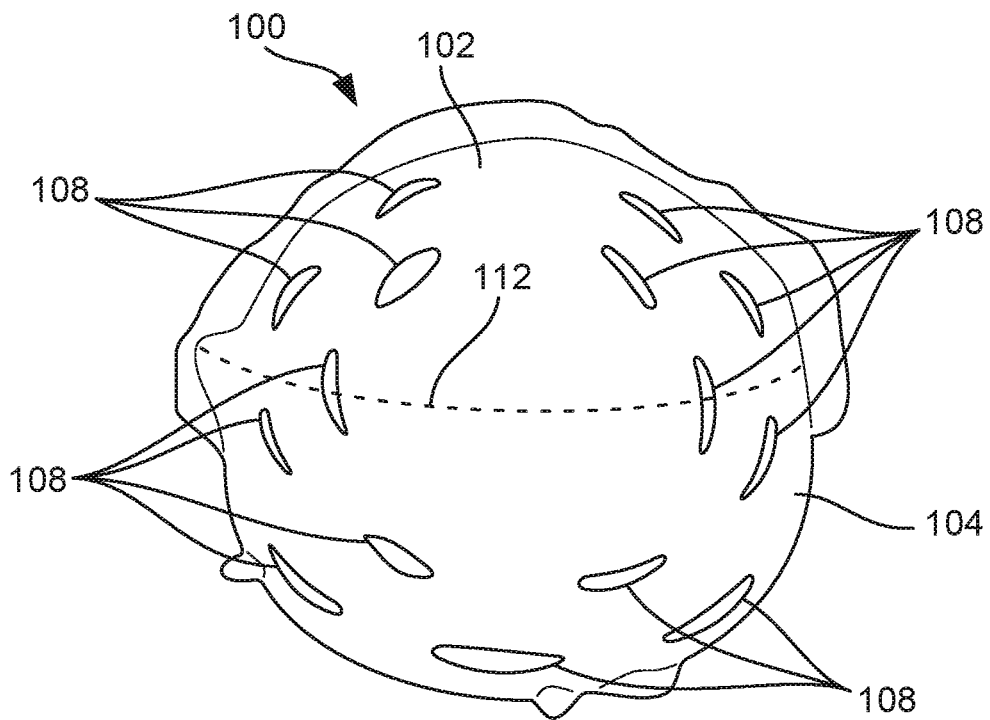
FIG. 26 is a top view of the reconstruction support of FIG. 24 in a rounded state.
Figure 27:
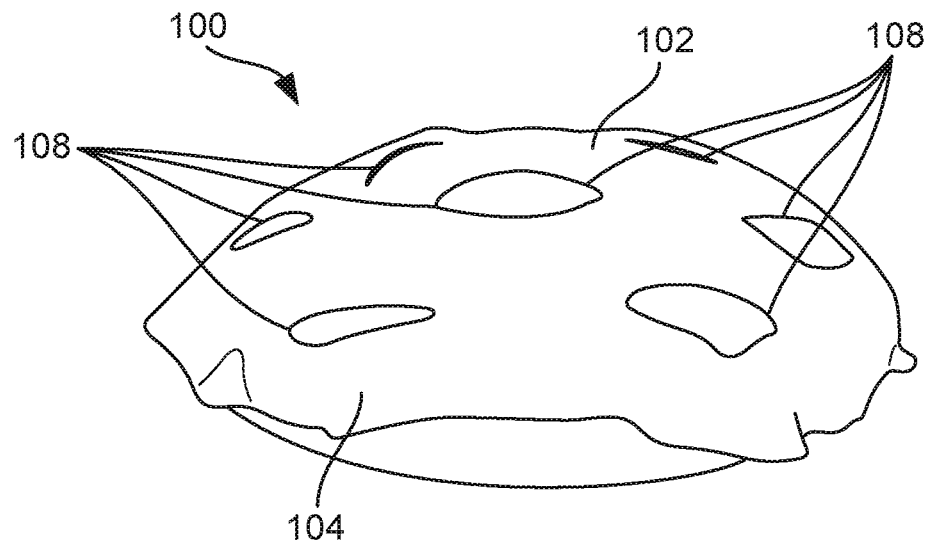
FIG. 27 is a front view of the reconstruction support of FIG. 24 in a rounded state.
Figure 28:
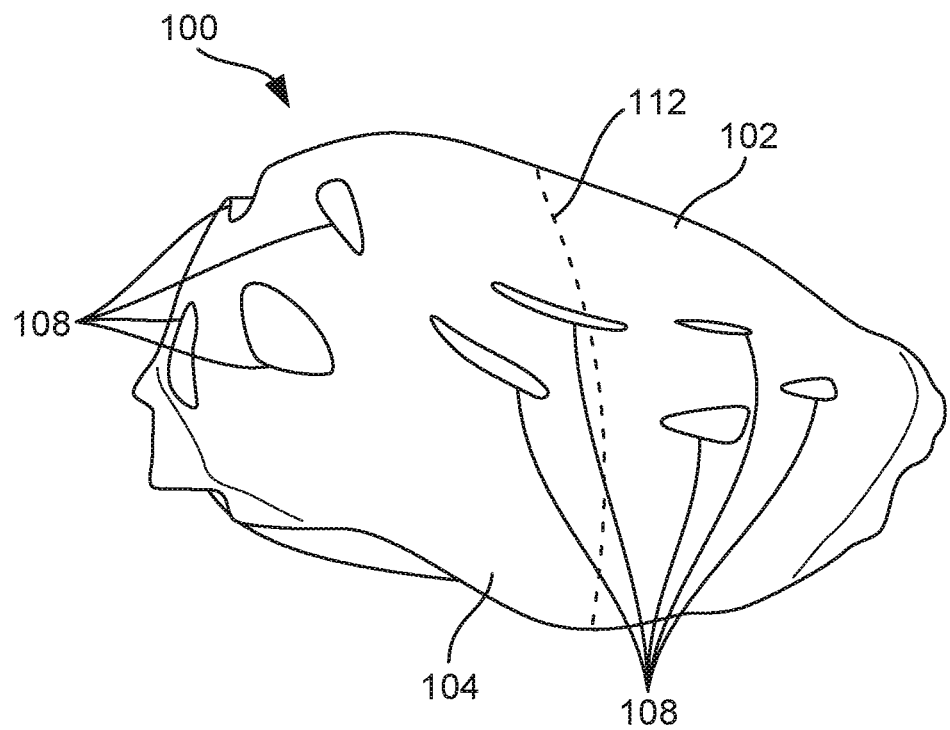
FIG. 28 is a side view of the reconstruction support of FIG. 24.
Figure 29:
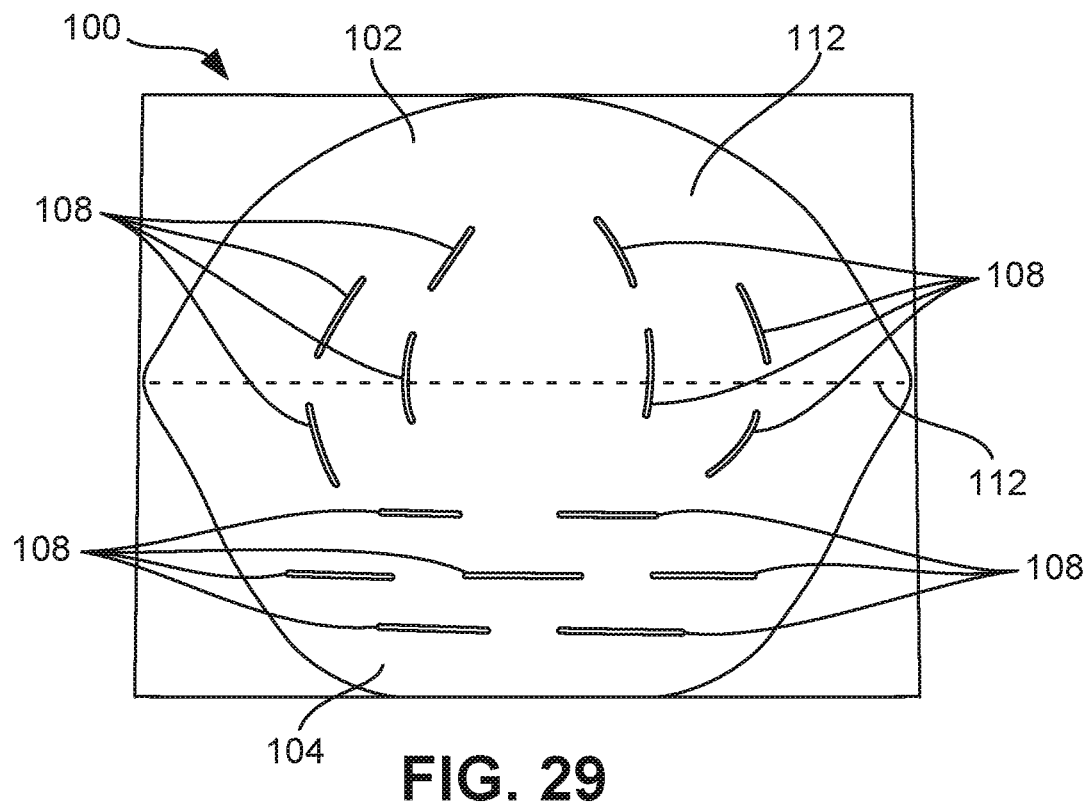
FIG. 29 is a top view of another example reconstruction support shown in a flat state and being constructed from a single piece of material.
Figure 30:
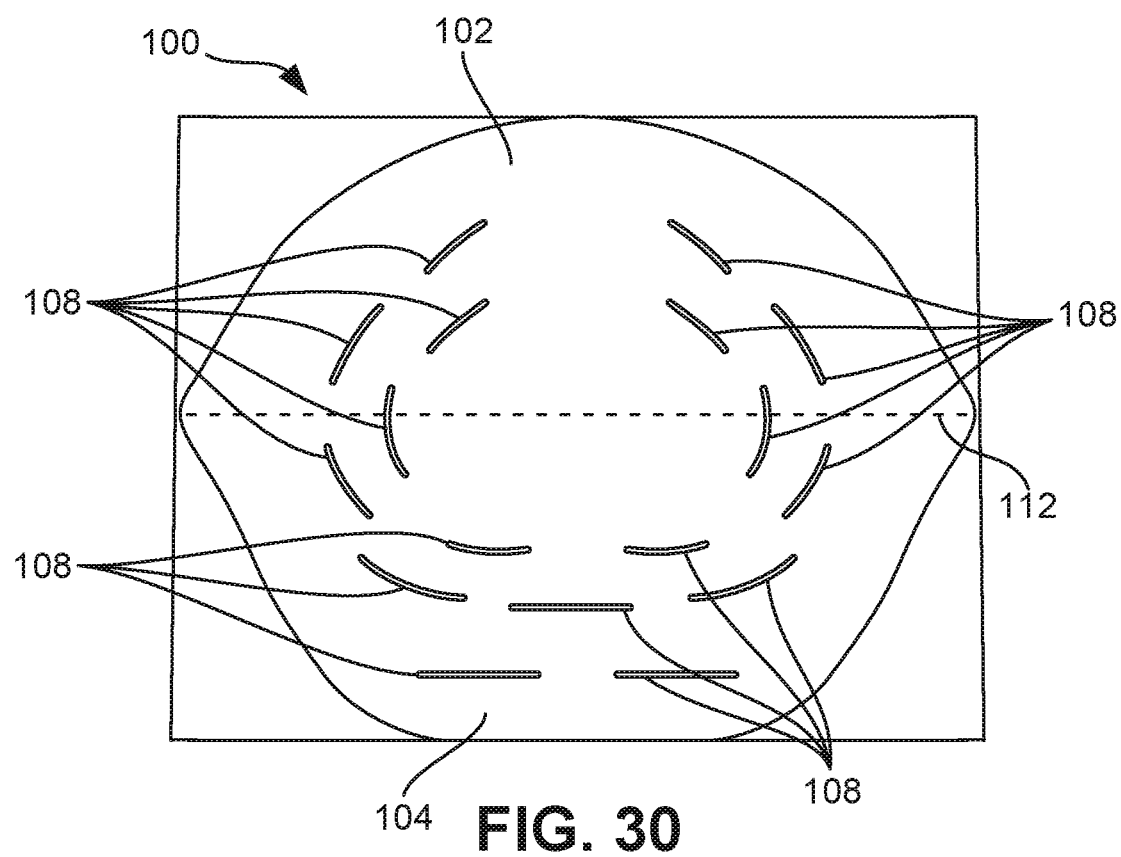
FIG. 30 is another top view of the reconstruction support of FIG. 29 in a flat state.
Figure 31:
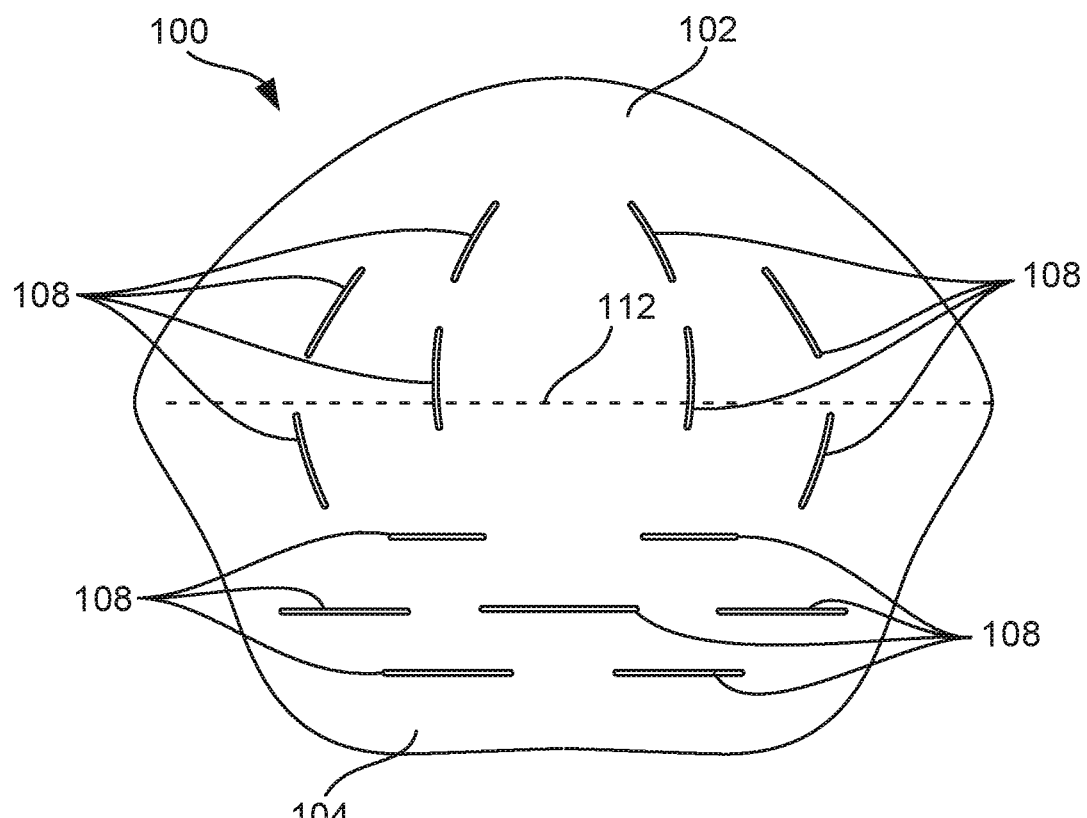
FIG. 31 is yet another top view of the reconstruction support of FIG. 29 in a flat state.
Figure 32:
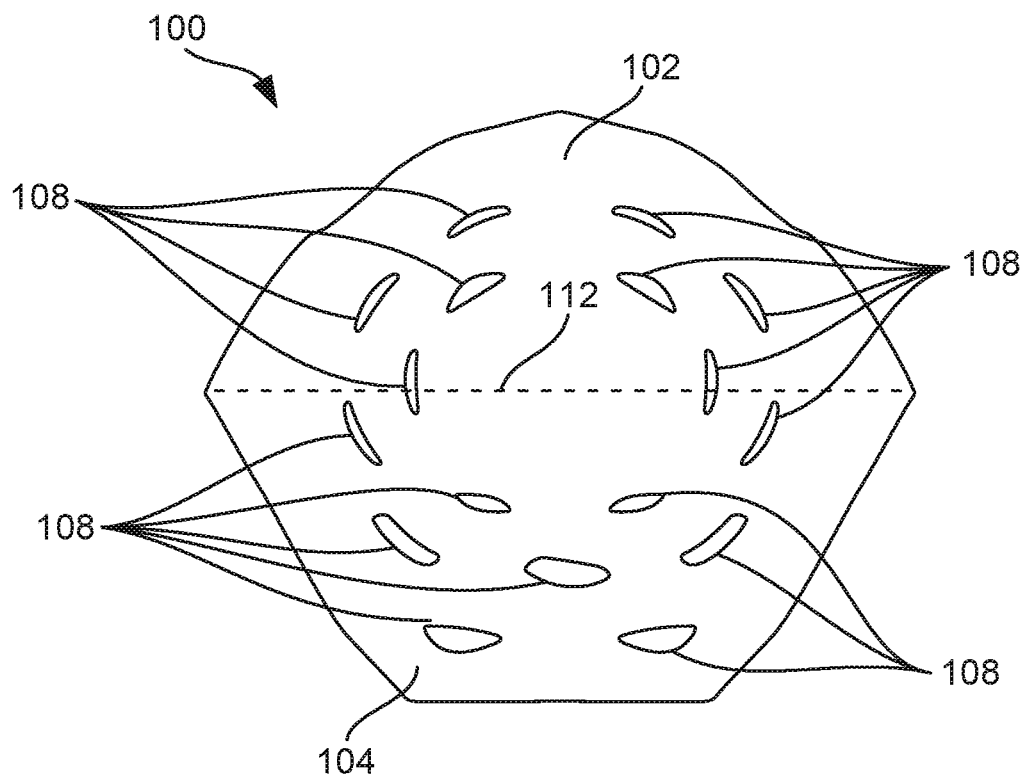
FIG. 32 is yet another top view of the reconstruction support of FIG. 29 in a flat state.

As shown in FIG. 11, the upper half 102 includes a first fold line 1106, a second fold line 1108, and a third fold line 1110. In some embodiments, the first fold line 1106 is brought together with the second fold line 1108 such that a triangular flap 1200 is formed, as shown in FIG. 12. This triangular flap 1200 is then cut out of the reconstruction support 100 by cutting the reconstruction support 100 along the first fold line 1106 and along the second fold line 1108, thereby forming a vertical appliqué 1300 in the upper half 102. The vertical appliqué 1300 is a V-shaped slit extending from a top edge of the upper half 102 towards the lower half 104. The vertical appliqué 1300 allows the reconstruction support 100 to be adjustable (e.g., configured to be tailored, etc.) for different implant sizes. For example, the vertical appliqué 1300 can be tightened to facilitate contraction of the reconstruction support 100 for smaller implants or loosened to facilitate expansion of the reconstruction support 100 for larger implants. The vertical appliqué 1300 may be centered on a vertical axis of the reconstruction support 100. Once the vertical appliqué 1300 has been formed, the reconstruction support 100 may be adjusted and then the vertical appliqué 1300 may be sewn closed.

In FIGS. 15-18, both the upper half 102 and the lower half 104 are integrated to form a single panel that is shaped like a rounded pentagon. FIGS. 15-18 illustrate an embodiment where the fenestrations 108 are located along each side and the bottom of the reconstruction support 100 but not along the top.

In FIGS. 19-23, both the upper half 102 and the lower half 104 are integrated to form a single panel that is shaped like a rounded pentagon. FIGS. 19-23 illustrate an embodiment where the reconstruction support 100 includes the vertical appliqué 1300. In FIG. 19-23, the fenestrations 108 are located along each side and the bottom of the reconstruction support 100 but not along the top near the vertical appliqué 1300.

In FIGS. 24-32, both the upper half 102 and the lower half 104 are integrated to form a single panel that is shaped like a rounded pentagon. FIGS. 24-32 illustrate an embodiment where some of the fenestrations 108 are curved and the fenestrations 108 are circumferentially disposed along most of the reconstruction support 100, except along a vertical line within a top portion of the reconstruction support 100. In some embodiments, the fenestrations 108 are approximately 2.3 centimeters long.

In FIGS. 24-32, the reconstruction support 100 includes three rows of asymmetrical fenestrations 108 inferiorly with 3.3 centimeter long at the lowest row 1.5 centimeters from the bottom of the reconstruction support 100 with one centimeter gap separating the two fenestrations 108, then a second row separated by 1.5 centimeter from the bottom row, measuring 3.2 centimeters in length with the outside curvilinear fenestrations 108, and an upper row again 1.5 centimeters from the middle row with 2.3 centimeter long fenestration 108 with lateral fenestrations 108 curving upward toward a vertical direction to become the outside most lateral and medial fenestrations 108 for the lateral and medial sides of the reconstruction support 100 respectively. This is four centimeters from the edge of the product with the next row more centrally about 1.5 centimeters apart from previous outside rows, again all 2.3 centimeters in length for the fenestrations 108 with one centimeter gaps, overlapping the lower row fenestrations 108.

Figure 33:
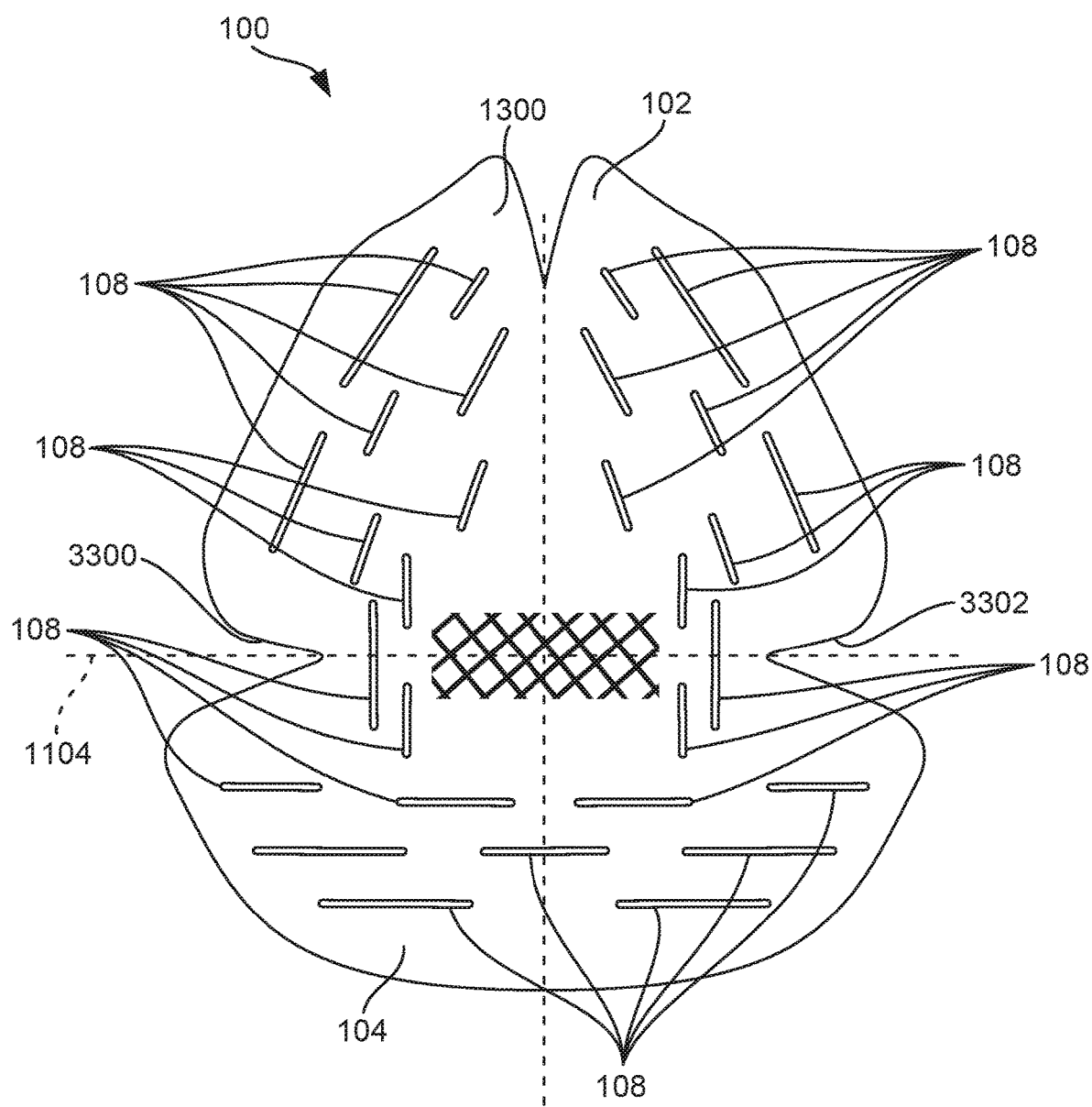
FIG. 33 is a top view of another example reconstruction support shown in a flat state and being constructed from a single piece of material.
Figure 34:
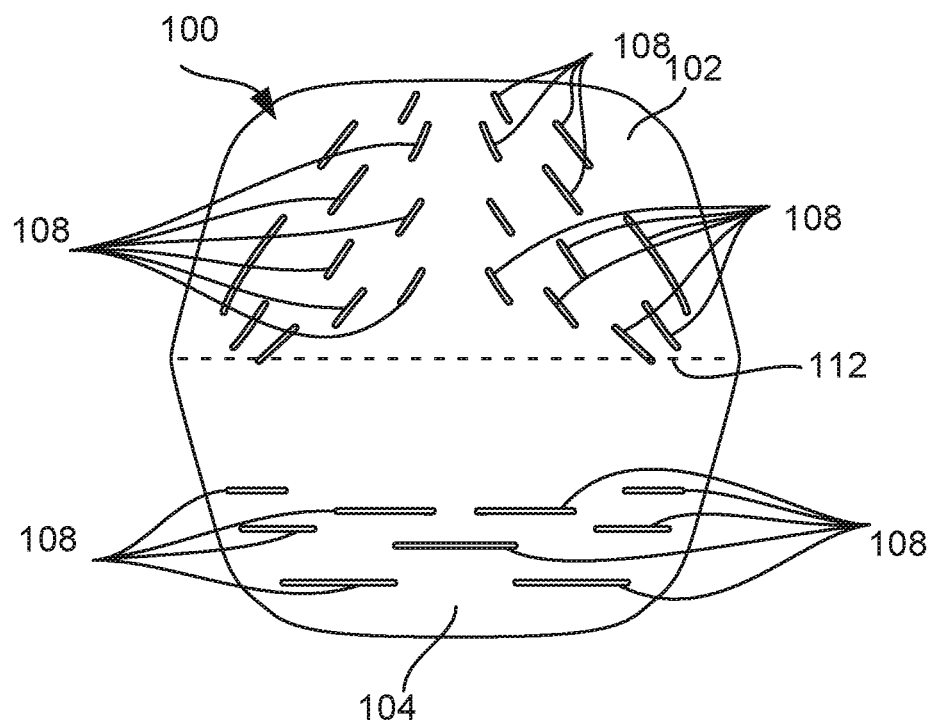
FIG. 34 is a top view of the reconstruction support of FIG. 33 in a rounded state.
Figure 35:
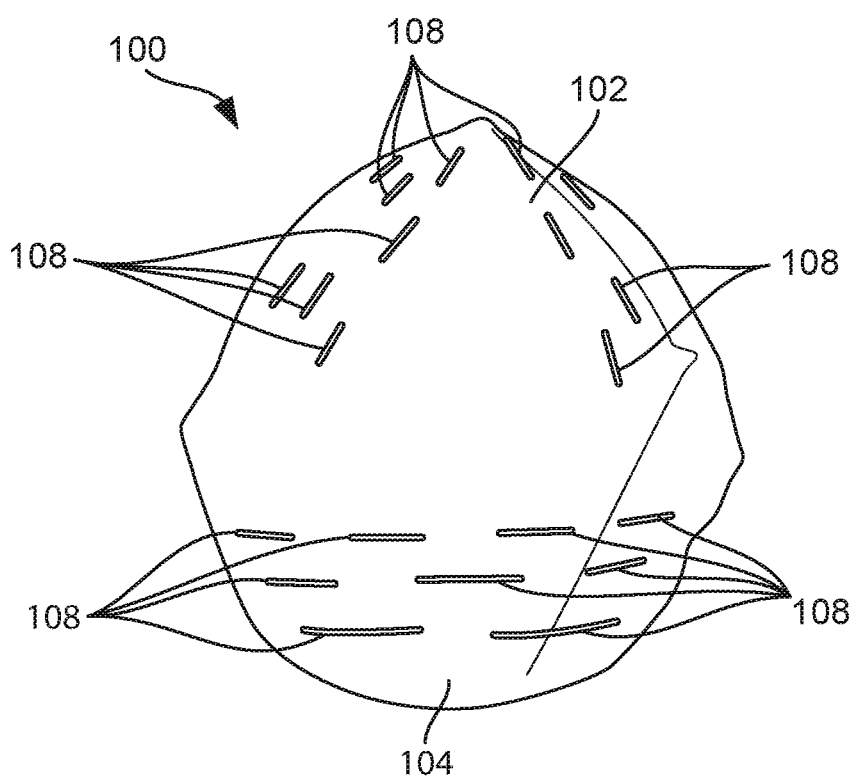
FIG. 35 is another top view of the reconstruction support of FIG. 33 in a rounded state.
Figure 36:
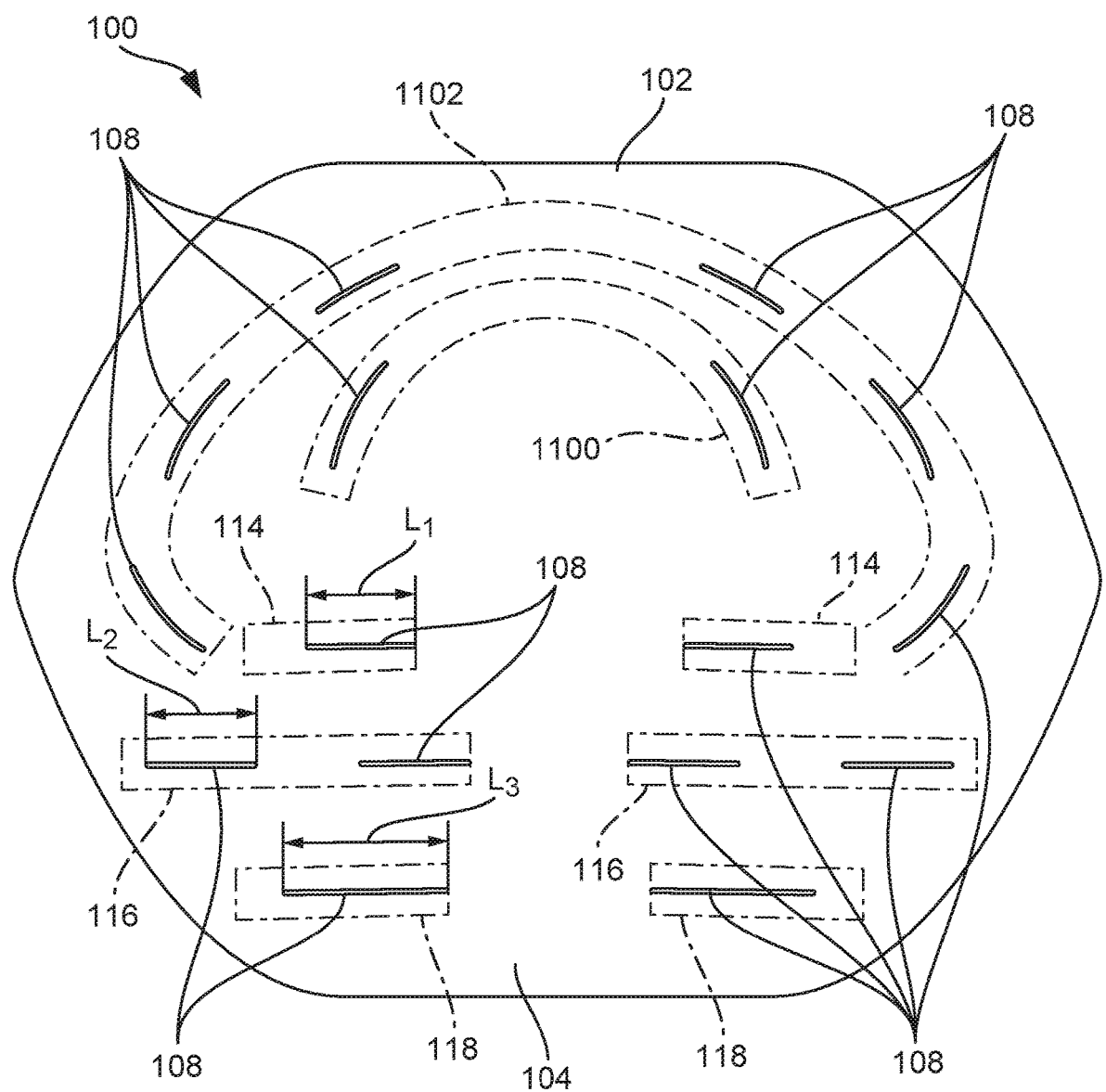
FIG. 36 is a top view of another example reconstruction support shown in a flat state and being constructed from a single piece of material.

In FIGS. 33-35, both the upper half 102 and the lower half 104 are integrated to form a single panel that is an ellipsoid. FIGS. 33-35 illustrate an embodiment where the fenestrations 108 are substantially straight and the fenestrations 108 are circumferentially disposed along most of the reconstruction support 100, except along a vertical line within a top portion of the reconstruction support 100. The reconstruction support 100 can also include three V-shaped slots, two of which are aligned along a horizontal plane, the third of which is along a vertical plane in the top portion of the reconstruction support 100. The reconstruction support 100 may include a portion that does not include fenestrations 108.

FIG. 33 illustrates an embodiment where the reconstruction support 100 includes a first horizontal appliqué 3300 and a second horizontal appliqué 3302. In various embodiments, the first horizontal appliqué 3300 and the second horizontal appliqué 3302 are centered on the horizontal plane 1104. The first horizontal appliqué 3300 and the second horizontal appliqué 3302 are each V-shaped slits extending from an outer edge of the reconstruction support 100 towards an interior of the reconstruction support 100. The first horizontal appliqué 3300 and the second horizontal appliqué 3302 allow the reconstruction support 100 to be adjustable for different implant sizes. For example, the first horizontal appliqué 3300 and the second horizontal appliqué 3302 can be tightened to facilitate contraction of the reconstruction support 100 for smaller implants or loosened to facilitate expansion of the reconstruction support 100 for larger implants.

In FIGS. 36-41, both the upper half 102 and the lower half 104 are integrated as a single panel that is shaped like a rounded pentagon. FIGS. 36-41 illustrate an embodiment where the fenestrations 108 are substantially straight and the fenestrations 108 are circumferentially disposed along most of the reconstruction support 100, except along a vertical line within a top portion of the reconstruction support 100. The reconstruction support 100 may include a portion that does not include fenestrations 108.

Figure 37:
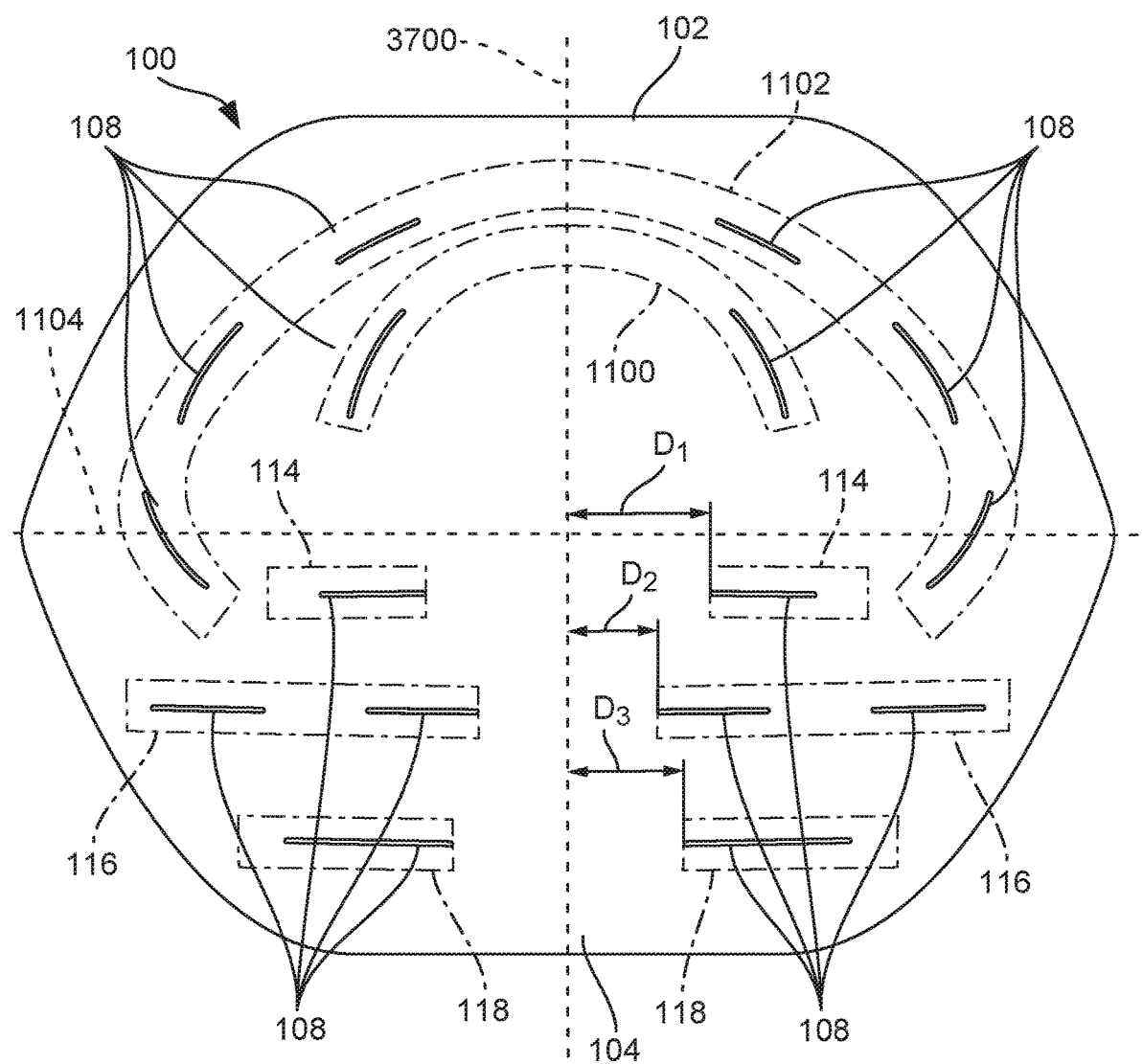
FIG. 37 is another top view of the reconstruction support of FIG. 36 in a flat state.
Figure 38:
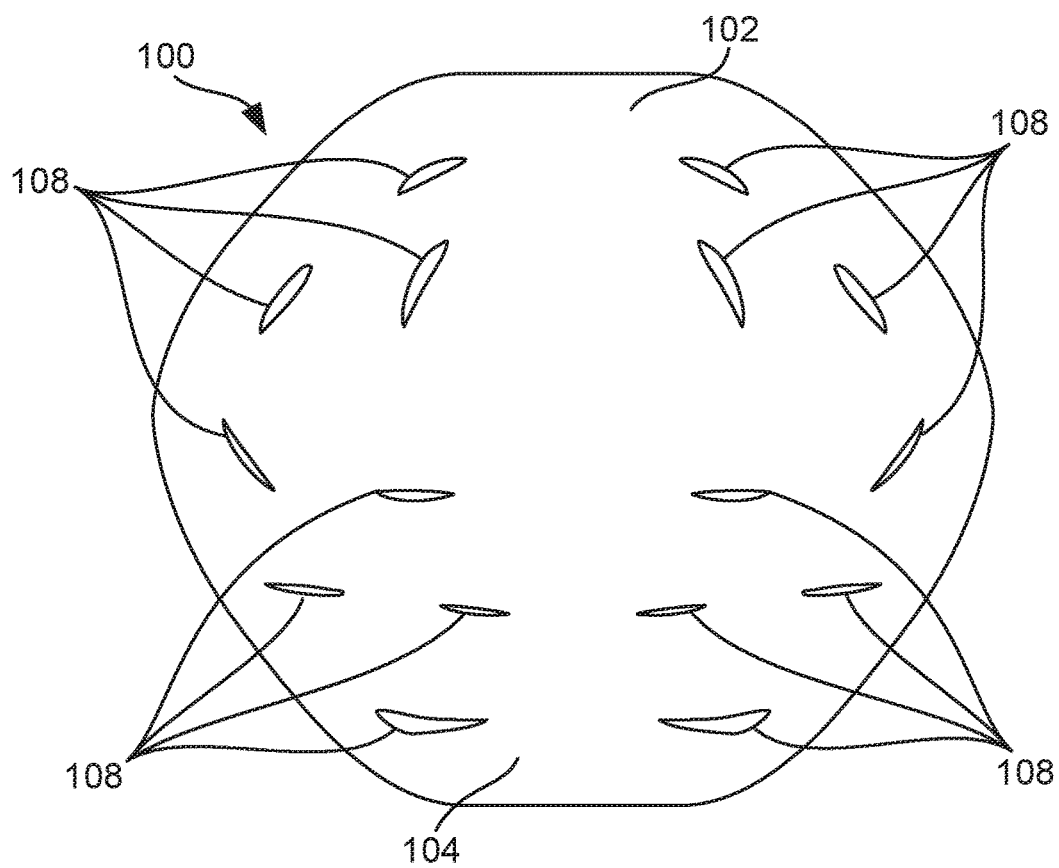
FIG. 38 is yet another top view of the reconstruction support of FIG. 36 in a flat state.
Figure 39:
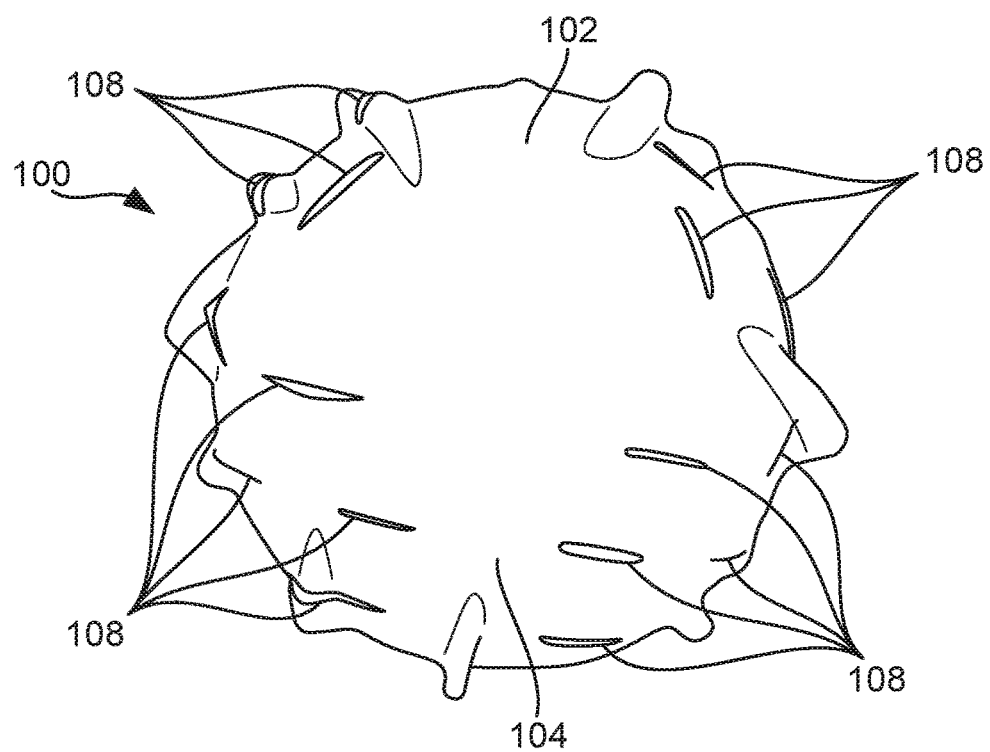
FIG. 39 is a top view of the reconstruction support of FIG. 36 in a rounded state.
Figure 40:
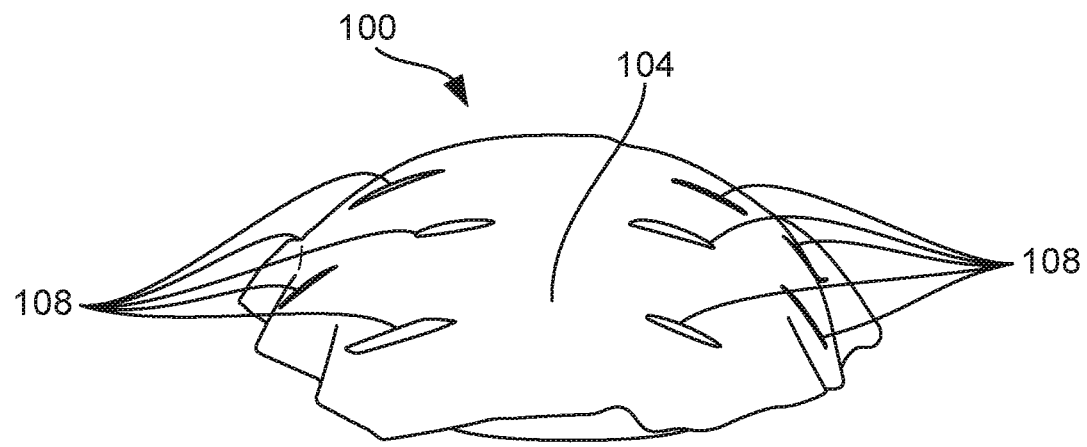
FIG. 40 is a front view of the reconstruction support of FIG. 36 in a rounded state.
Figure 41:
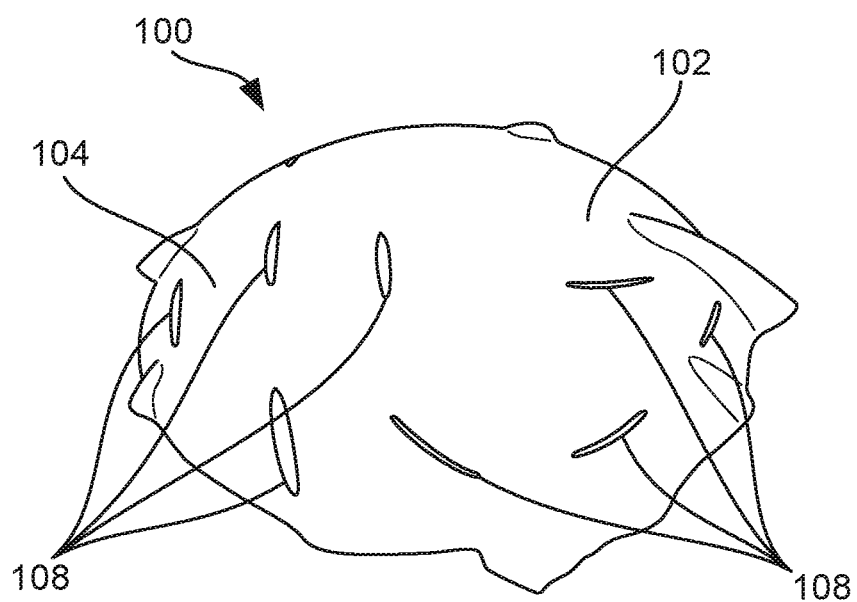
FIG. 41 is a top side view of the reconstruction support of FIG. 36 in a rounded state.

In various embodiments, the reconstruction support 100 is bisected by a vertical plane 3700. As shown in FIG. 37, the vertical plane 3700 bisects two sections of the first row 114, two sections of the second row 116, and two sections of the third row 118. Each of the two sections of the first row 114 contains at least one fenestration 108, each of the two sections of the second row 116 contains at least one fenestration 108, and each of the two sections of the third row 118 contains at least one fenestration 108. In various embodiments, the reconstruction support 100 is substantially symmetrical about the vertical plane 3700.

The reconstruction support 100 is configured such that a nearest of the fenestrations 108 of the first row 114 is separated from the vertical plane 3700 a first distance $D_1$, a nearest of the fenestrations 108 of the second row 116 is separated from the vertical plane 3700 a second distance $D_2$, and a nearest of the fenestrations 108 of the third row 118 is separated from the vertical plane 3700 a third distance $D_3$. In an example embodiment, the first distance $D_1$ is 2 cm, the second distance $D_2$ is 1 cm, and the third distance $D_3$ is 1.5 cm. In some of these embodiments, the first length $L_1$ of the fenestrations 108 in the first row 114 is 2 cm, the second length $L_2$ of the fenestrations 108 in the second row 116 is 2 cm, and the third length $L_3$ of the fenestrations 108 in the third row 118 is 3 cm. When the first row 114, the second row 116, and the third row 118 are centered on the vertical plane 3700, a gap between the fenestrations 108 exists along the vertical plane 3700. This gap is largest between adjacent fenestrations 108 in the first row 114 and smallest between adjacent fenestrations 108 in the second row 116. In various embodiments, this gap between adjacent fenestrations 108 in the second row 116 is 2 cm.

Figure 42:
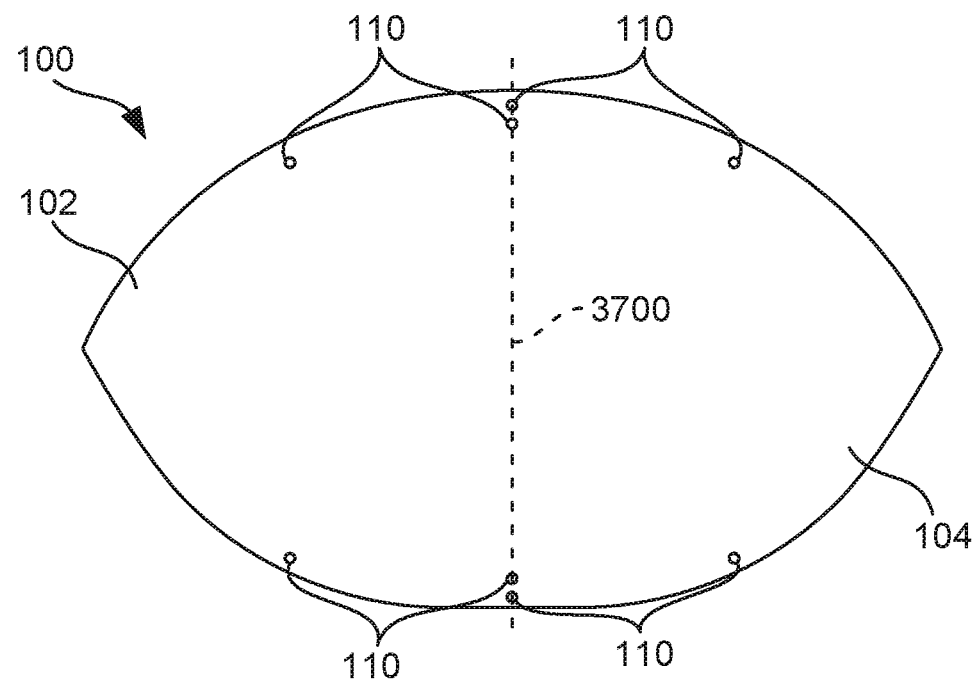
FIG. 42 is a top view of another example reconstruction support shown in a flat state and being constructed from a single piece of material.

In FIG. 42, both the upper half 102 and the lower half 104 are integrated as a single panel that is shaped like a rounded pentagon. FIG. 42 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104.

Figure 43:
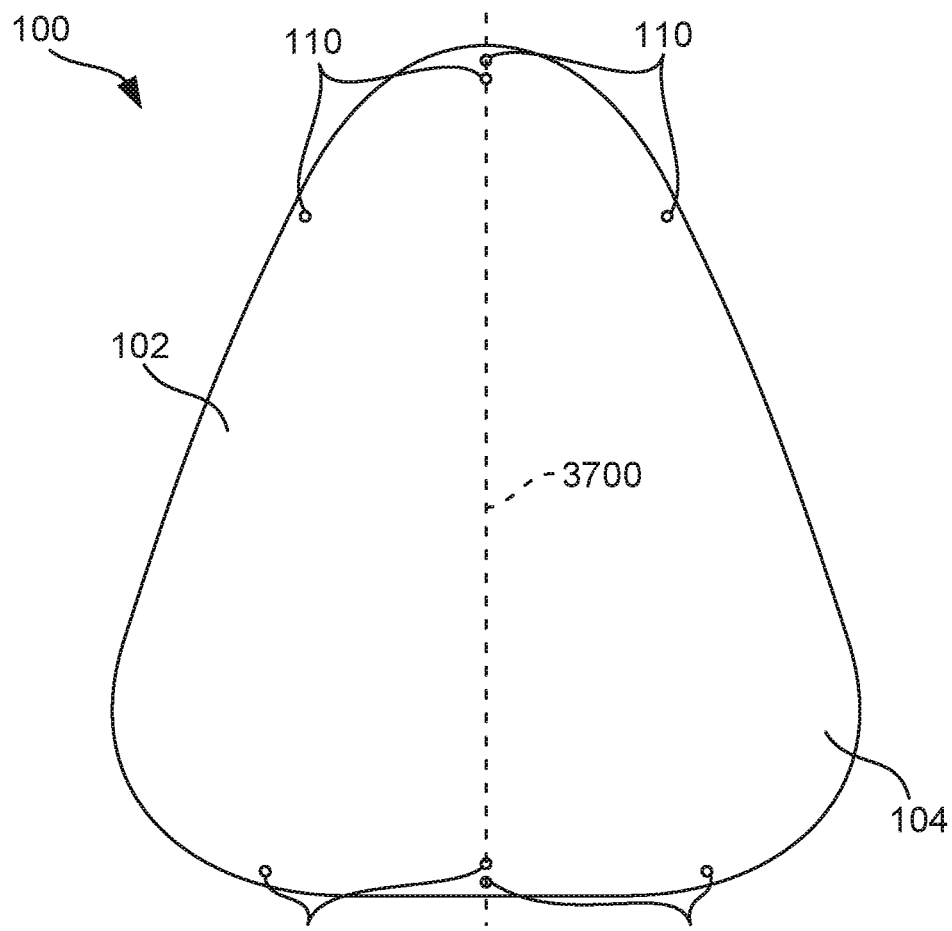
FIG. 43 is a top view of another example reconstruction support shown in a flat state and being constructed from a single piece of material.

In FIG. 43, both the upper half 102 and the lower half 104 are integrated as a single panel that is an ellipsoid. FIG. 43 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104.

Figure 44:
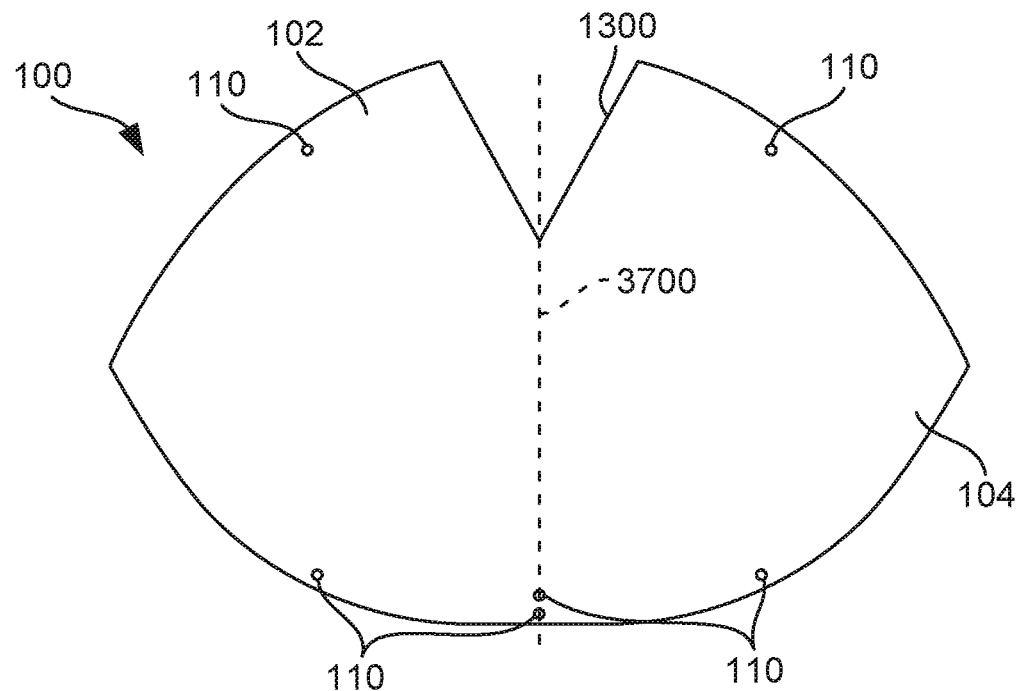
FIG. 44 is a top view of another example reconstruction support shown in a flat state and being constructed from a single piece of material.

In FIG. 44, both the upper half 102 and the lower half 104 are integrated as a single panel that is shaped like a rounded pentagon. FIG. 44 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the lower half 104. The reconstruction support 100 also includes the vertical appliqué 1300. The vertical appliqué 1300 is centered on the vertical plane 3700.

Figure 45:
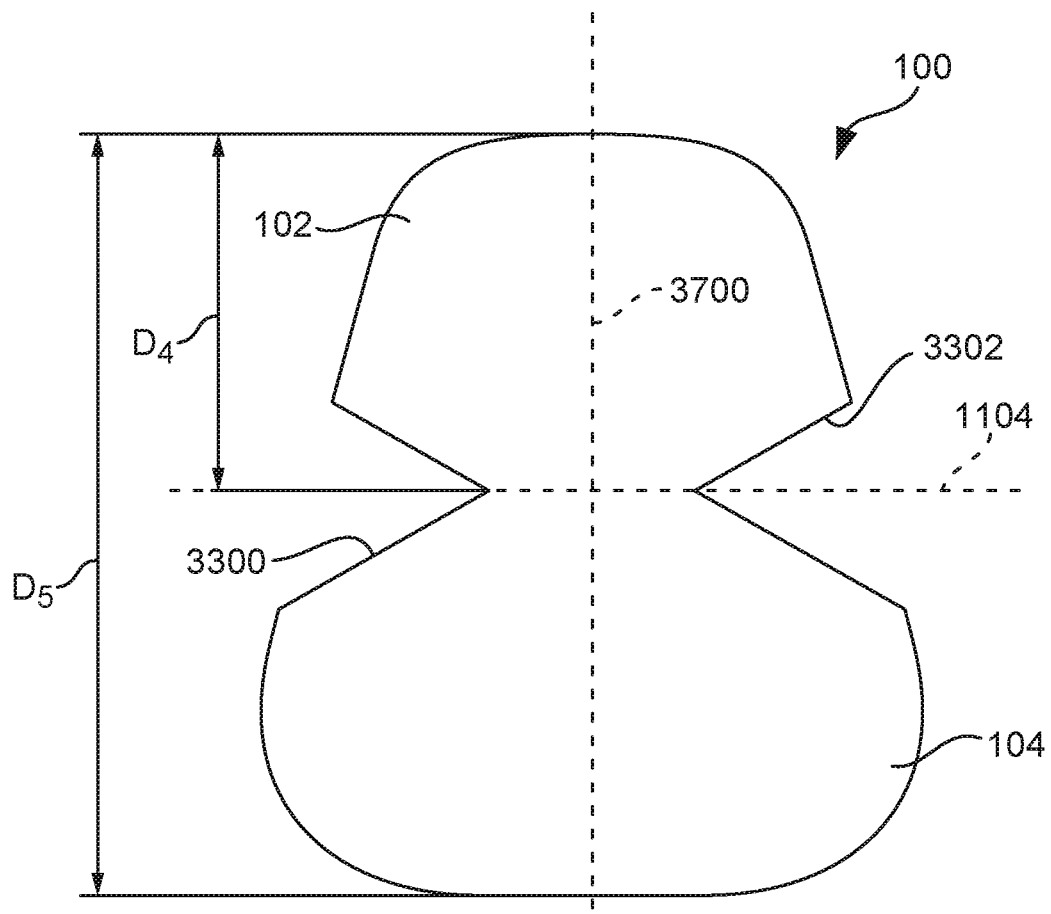
FIG. 45 is a top view of another example reconstruction support shown in a flat state and being constructed from a single piece of material.

In FIG. 45, both the upper half 102 and the lower half 104 are integrated as a single panel that is an ellipsoid. FIG. 45 illustrates an embodiment where the reconstruction support 100 includes the first horizontal appliqué 3300 and the second horizontal appliqué 3302. The first horizontal appliqué 3300 and the second horizontal appliqué 3302 are located a fourth distance $D_4$ between a center point of the first horizontal appliqué 3300 and the second horizontal appliqué 3302 and a vertex of the upper half 102. In various embodiments, the fourth distance $D_4$ is between 20-75% of a fifth distance $D_5$ between the vertex of the upper half 102 and a vertex of the lower half 104.

Figure 46:
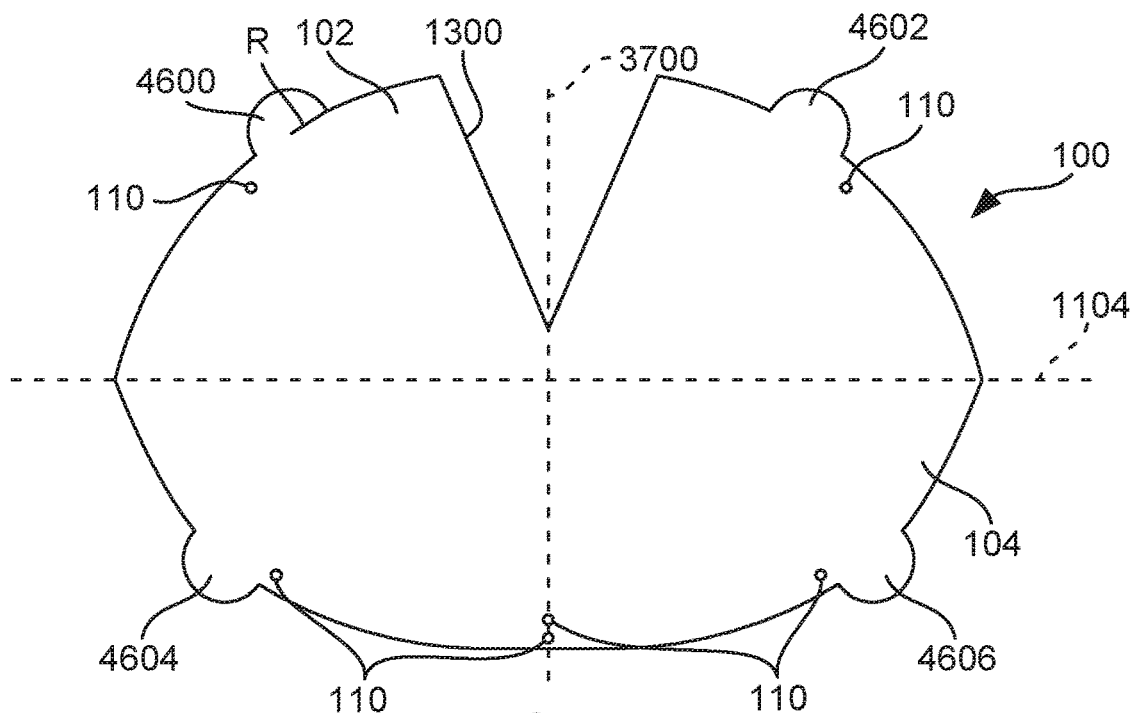
FIG. 46 is a top view of another example reconstruction support shown in a flat state and being constructed from a single piece of material.

In FIG. 46, both the upper half 102 and the lower half 104 are integrated as a single panel that is shaped like a rounded pentagon. FIG. 46 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the lower half 104. The reconstruction support 100 also includes the vertical appliqué 1300. The reconstruction support 100 includes a first tab 4600 and a second tab 4602 positioned along a perimeter of the upper half 102 and on opposite sides of the vertical appliqué 1300. The reconstruction support 100 also includes a third tab 4604 and a fourth tab 4606 positioned along a perimeter of the lower half 104 and on opposite sides of the vertical plane 3700. The reconstruction support 100 may be configured such that the first tab 4600 and the third tab 4604 are aligned along a first plane which is parallel to, and a first distance from, the vertical plane 3700, and such that the second tab 4602 and the fourth tab 4606 are aligned along a second plane which is parallel to, and the first distance from, the vertical plane 3700. The reconstruction support 100 may also be configured such that the first tab 4600 and the second tab 4602 are aligned along a third plane which is parallel to, and a second distance from, the horizontal plane 1104, and such that the third tab 4604 and the fourth tab 4606 are aligned along a fourth plane which is parallel to, and the first distance from, the horizontal plane 1104. The first tab 4600, the second tab 4602, the third tab 4604, and the fourth tab 4606 may facilitate manipulation and placement of the reconstruction support 100. For example, the first tab 4600 may provide a user with a readily graspable portion of the reconstruction support 100 which can be grasped by a user to manipulate the reconstruction support 100. In this way, the first tab 4600, the second tab 4602, the third tab 4604, and/or the fourth tab 4606 may provide a user with an ideal hand in glove fit. Once the reconstruction support 100 is located, the first tab 4600, the second tab 4602, the third tab 4604, and/or the fourth tab 4606 may serve as locations for stitching to underlying tissue. As shown in FIG. 46, each of the first tab 4600, the second tab 4602, the third tab 4604, and the fourth tab 406 is semi-circular and has a radius R. In various embodiments, the radius R is between 5 and 10 mm, inclusive.

Figure 47:
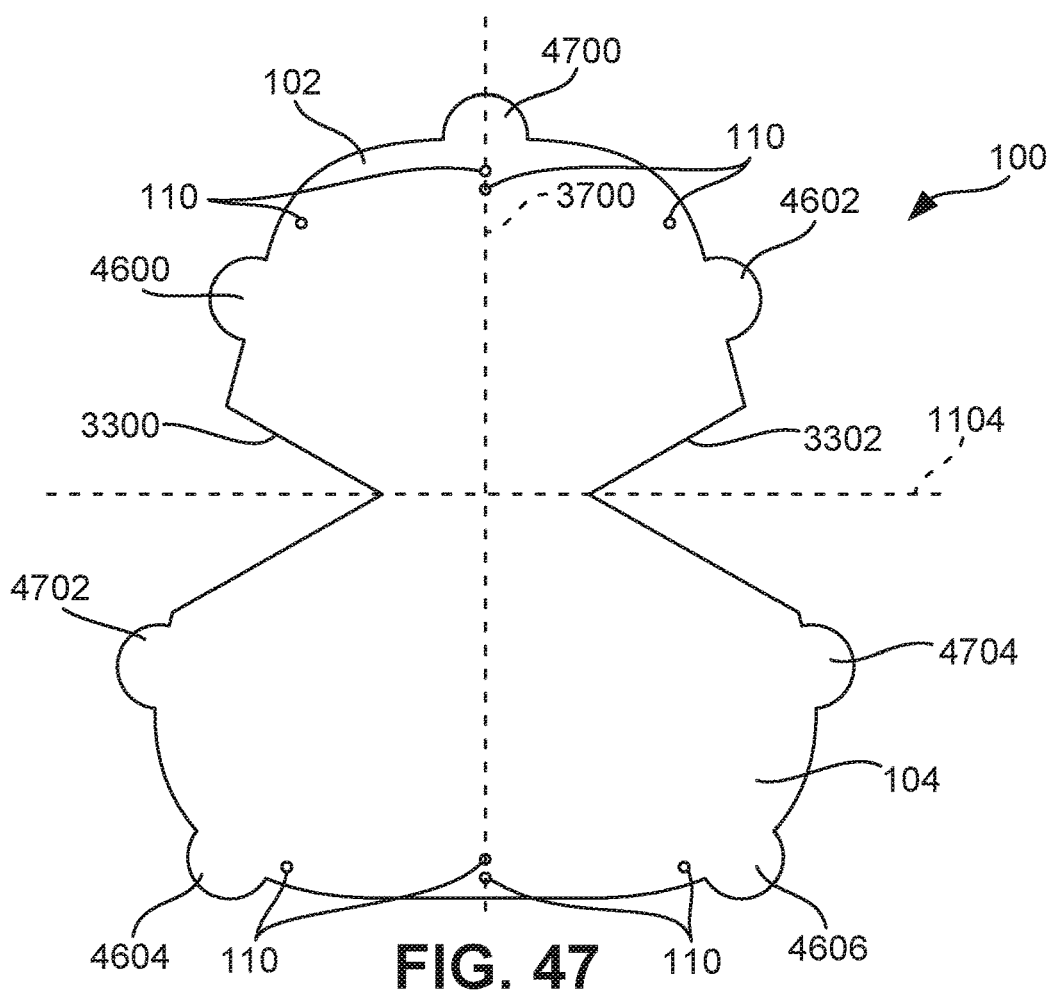
FIG. 47 is a top view of another example reconstruction support shown in a flat state and being constructed from a single piece of material.

In FIG. 47, both the upper half 102 and the lower half 104 are integrated as a single panel that is an ellipsoid. FIG. 47 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. FIG. 47 also illustrates an embodiment where the reconstruction support 100 includes the first horizontal appliqué 3300 and the second horizontal appliqué 3302. FIG. 47 also illustrates an embodiment where the reconstruction support 100 includes the first tab 4600, the second tab 4602, the third tab 4604, and the fourth tab 4606. Additionally, the reconstruction support 100 includes a fifth tab 4700 positioned along a perimeter of the upper half 102 and centered on the vertical plane 3700, a sixth tab 4702 positioned along a perimeter of the lower half 104, and a seventh tab 4704 positioned along a perimeter of the lower half 104. The fifth tab 4700, the sixth tab 4702, and the seventh tab 4704 have the general configuration, structure, and function as described with regard to the first tab 4600, the second tab 4602, the third tab 4604, and the fourth tab 4606. The sixth tab 4702 and the seventh tab 4704 are on opposite sides of the vertical plane 3700. The reconstruction support 100 may be configured such that the sixth tab 4702 and the seventh tab 4704 are aligned along a plane which is substantially parallel to the horizontal plane 1104. The fifth tab 4700, the sixth tab 4702, and the seventh tab 4704 may facilitate manipulation and placement of the reconstruction support 100. For example, the fifth tab 4700 may provide a user with a readily graspable portion of the reconstruction support 100 which can be grasped by a user to manipulate the reconstruction support 100.

Figure 48:
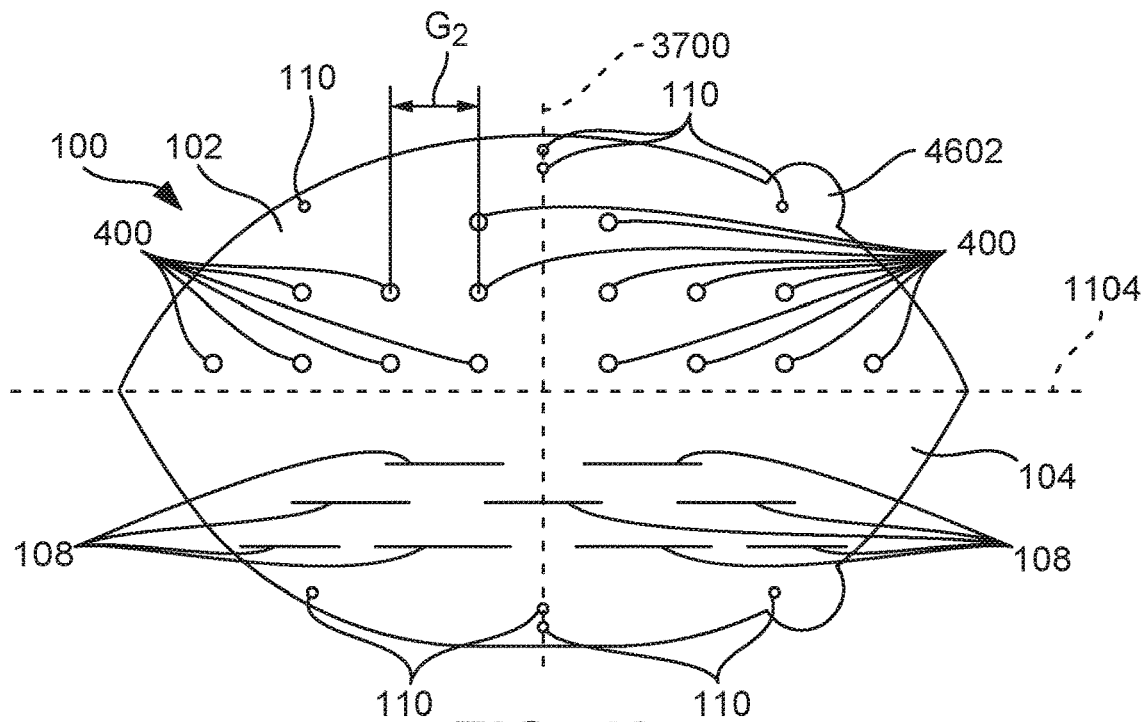
FIG. 48 is a top view of another example reconstruction support shown in a flat state and being constructed from a single piece of material.

In FIG. 48, both the upper half 102 and the lower half 104 are integrated as a single panel that is shaped like a rounded pentagon. FIG. 48 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the lower half 104. The reconstruction support 100 also includes the second tab 4602 and the fourth tab 4606. FIG. 48 also illustrates an embodiment where the reconstruction support 100 includes the plurality of egress perforations 400. FIG. 48 also illustrates an embodiment where the egress perforations 400 are arranged in a plurality of substantially parallel rows having a plurality of substantially aligned columns. The plurality of substantially parallel rows of the egress perforations 400 includes a fourth row, a fifth row, and a sixth row, such that the fifth row is positioned between the fourth row and the sixth row. The fourth row includes a sixth subset of the plurality of egress perforations 400, the fifth row includes a seventh subset of the plurality of egress perforations 400, and the sixth row includes an eighth subset of the plurality of egress perforations 400. In some embodiments, the fourth row and the fifth row are positioned such that the sixth subset of the plurality of egress perforations 400 is offset relative to the seventh subset of the plurality of egress perforations 400. In some embodiments, the fifth row and the sixth row are positioned such that the seventh subset of the plurality of egress perforations 400 is offset relative to the eighth subset of the plurality of egress perforations 400. In some embodiments, the reconstruction support 100 also includes the vertical appliqué 1300, as previously described. In some embodiments, the rows of egress perforations 400 are arranged such that the egress perforations 400 in one row may be staggered relative to the egress perforations 400 in an adjacent row.

The egress perforations 400 in a row are separated by a second gap $G_2$ between adjacent egress perforations 400 in that row. In various embodiments, the second gap $G_2$ is between 10-30 mm, inclusive. In various embodiments, the egress perforations 400 are each generally circular and defined by a diameter of between 1-5 mm, inclusive. In an example embodiment, each of the egress perforations 400 is at least 5 mm from any of the fenestrations 108.

Figure 49:
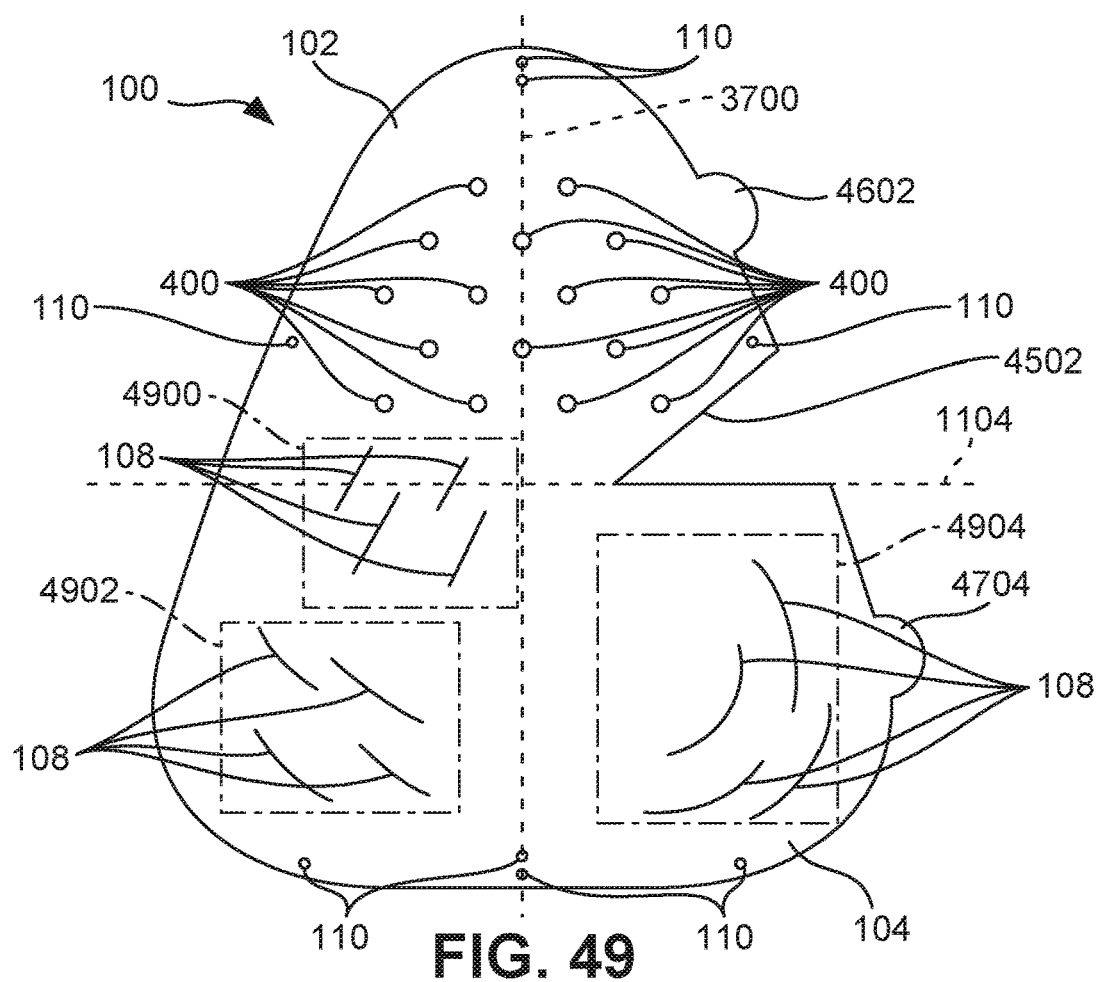
FIG. 49 is a top view of another example reconstruction support shown in a flat state and being constructed from a single piece of material.

In FIG. 49, both the upper half 102 and the lower half 104 are integrated as a single panel that is an ellipsoid. FIG. 49 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. FIG. 49 also illustrates an embodiment where the reconstruction support 100 includes the second horizontal appliqué 3302. An edge of the second horizontal appliqué 3302 may be coincident with the horizontal plane 1104. FIG. 49 also illustrates an embodiment where the reconstruction support 100 includes the second tab 4602 and the seventh tab 4704 such that the second horizontal appliqué 3302 is contained in the upper half 102. Additionally, FIG. 49 illustrates an embodiment where the reconstruction support 100 includes a radial group 4900 of the plurality of fenestrations 108, an oblique group 4902 of the plurality of fenestrations 108, and a curvilinear group 4904 of the plurality of fenestrations 108. The radial group 4900 contains a plurality of fenestrations 108, each of which is radially oriented. The oblique group 4902 contains a plurality of fenestrations 108, each of which has a degree of obliquity. The plurality of fenestrations 108 in the oblique group 4902 may have various degrees of obliquity. The curvilinear group 4904 contains a plurality of fenestrations 108, each of which has a curvilinear shape. FIG. 49 also illustrates an embodiment where the reconstruction support 100 includes the egress perforations 400 in a plurality of substantially parallel rows, such that the egress perforations 400 in one row are staggered relative to the egress perforations 400 in an adjacent row. In an example embodiment, each of the egress perforations 400 is at least 5 mm from any of the fenestrations 108.

Figure 50:
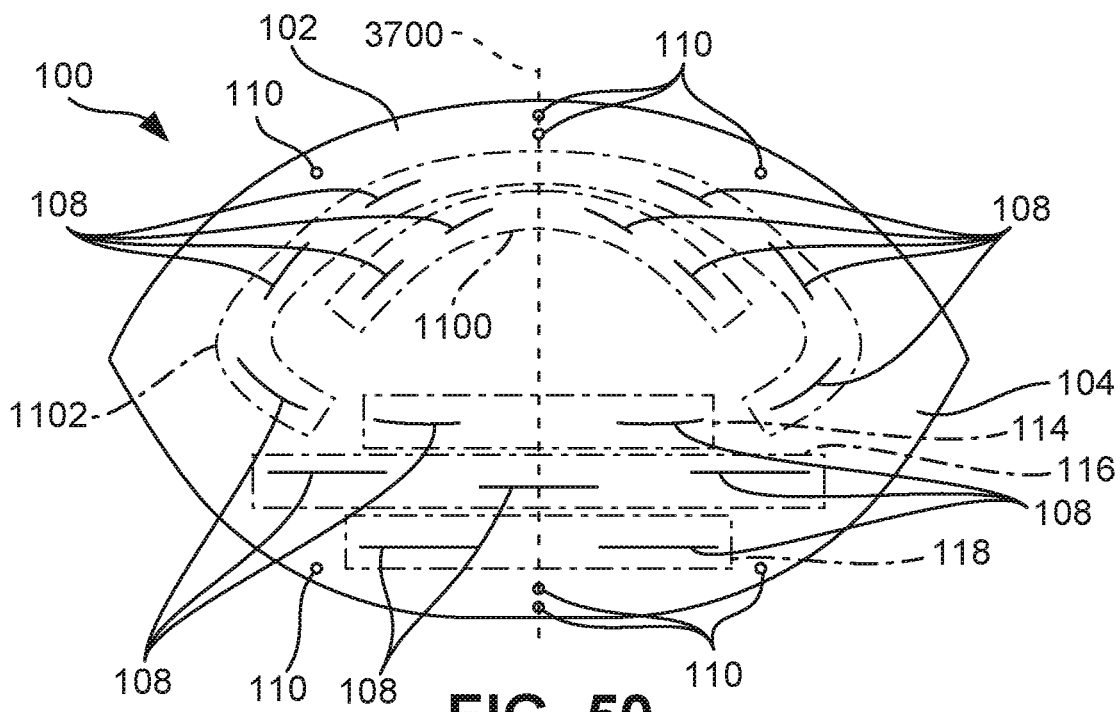
FIG. 50 is a top view of another example reconstruction support shown in a flat state and being constructed from a single piece of material.

In FIG. 50, both the upper half 102 and the lower half 104 are integrated as a single panel that is shaped like a rounded pentagon. FIG. 50 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. The reconstruction support 100 also includes the plurality of fenestrations 108. The plurality of fenestrations 108 is arranged in the first row 114, the second row 116, the third row 118, the first arc 1100, and the second arc 1102. In some embodiments, the fenestrations 108 may be arranged in a plurality of concentric arcs such that a majority of the fenestrations 108 are at least partially disposed in the lower half 104 and a minority of the fenestrations 108 are at least partially disposed in the upper half 102.

Figure 51:
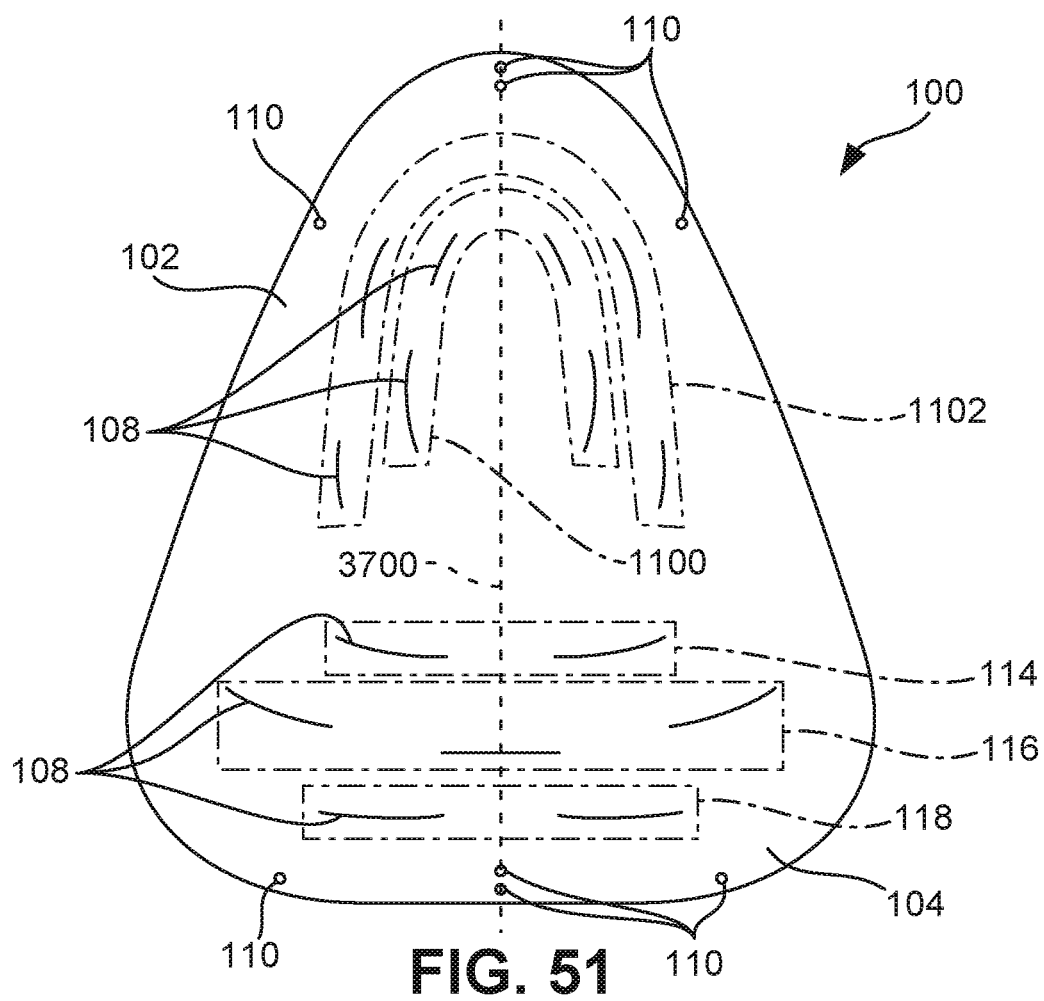
FIG. 51 is a top view of another example reconstruction support shown in a flat state and being constructed from a single piece of material.

In FIG. 51, both the upper half 102 and the lower half 104 are integrated as a single panel that is an ellipsoid. FIG. 51 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. The reconstruction support 100 also includes the plurality of fenestrations 108. The plurality of fenestrations 108 is arranged in the first row 114, the second row 116, the third row 118, the first arc 1100, and the second arc 1102. In some embodiments, the fenestrations 108 may be arranged in a plurality of concentric arcs such that a majority of the fenestrations 108 are at least partially disposed in the lower half 104 and a minority of the fenestrations 108 are at least partially disposed in the upper half 102.

Figure 52:
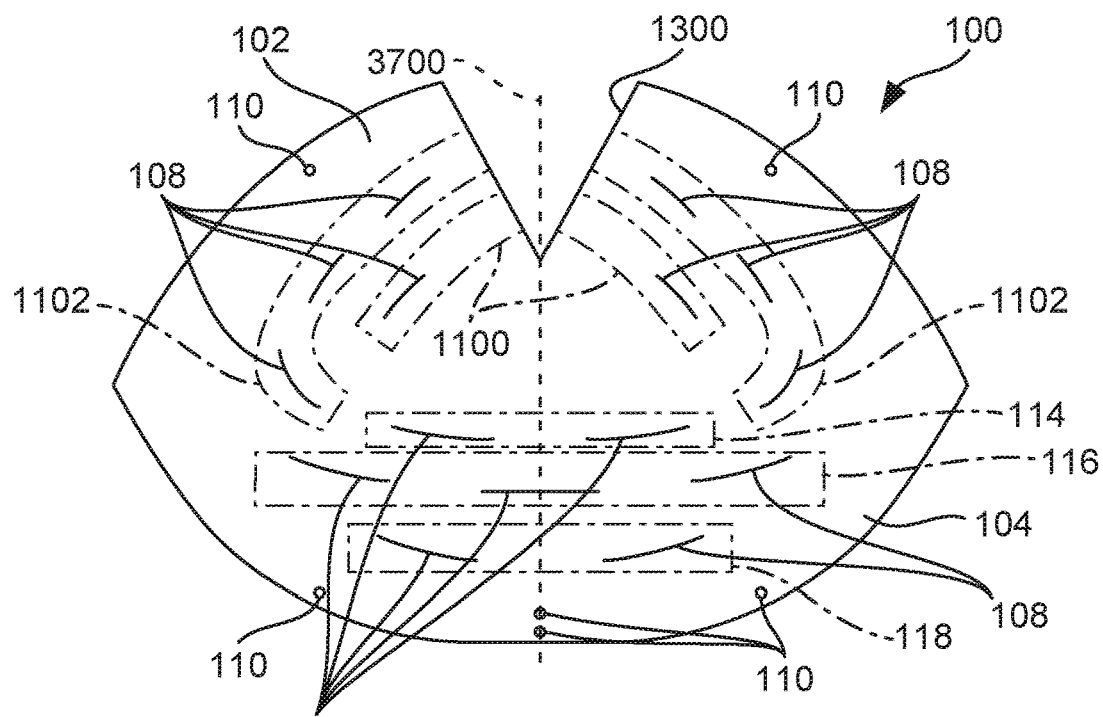
FIG. 52 is a top view of another example reconstruction support shown in a flat state and being constructed from a single piece of material.

In FIG. 52, both the upper half 102 and the lower half 104 are integrated as a single panel that is shaped like a rounded pentagon. FIG. 52 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the lower half 104. The reconstruction support 100 also includes the plurality of fenestrations 108. The plurality of fenestrations 108 is arranged in the first row 114, the second row 116, the third row 118, the first arc 1100, and the second arc 1102. FIG. 52 also illustrates the reconstruction support 100 as including the vertical appliqué 1300. In some embodiments, the fenestrations 108 may be arranged in a plurality of concentric arcs such that a majority of the fenestrations 108 are at least partially disposed in the lower half 104 and a minority of the fenestrations 108 are at least partially disposed in the upper half 102.

Figure 53:
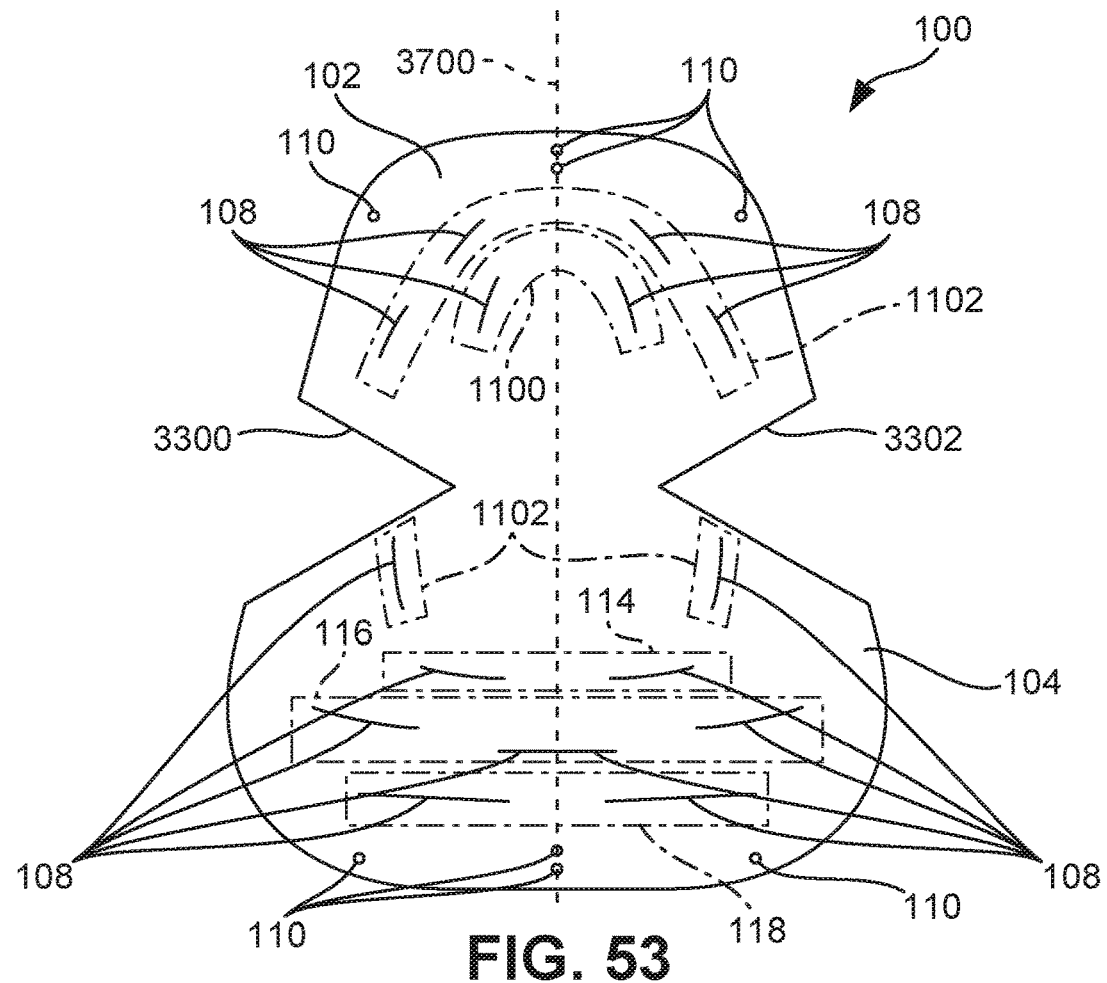
FIG. 53 is a top view of another example reconstruction support shown in a flat state and being constructed from a single piece of material.

In FIG. 53, both the upper half 102 and the lower half 104 are integrated as a single panel that is an ellipsoid. FIG. 53 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. The reconstruction support 100 also includes the plurality of fenestrations 108. The plurality of fenestrations 108 is arranged in the first row 114, the second row 116, the third row 118, the first arc 1100, and the second arc 1102. FIG. 53 also illustrates the reconstruction support 100 as including the first horizontal appliqué 3300 and the second horizontal appliqué 3302.

Figure 54:
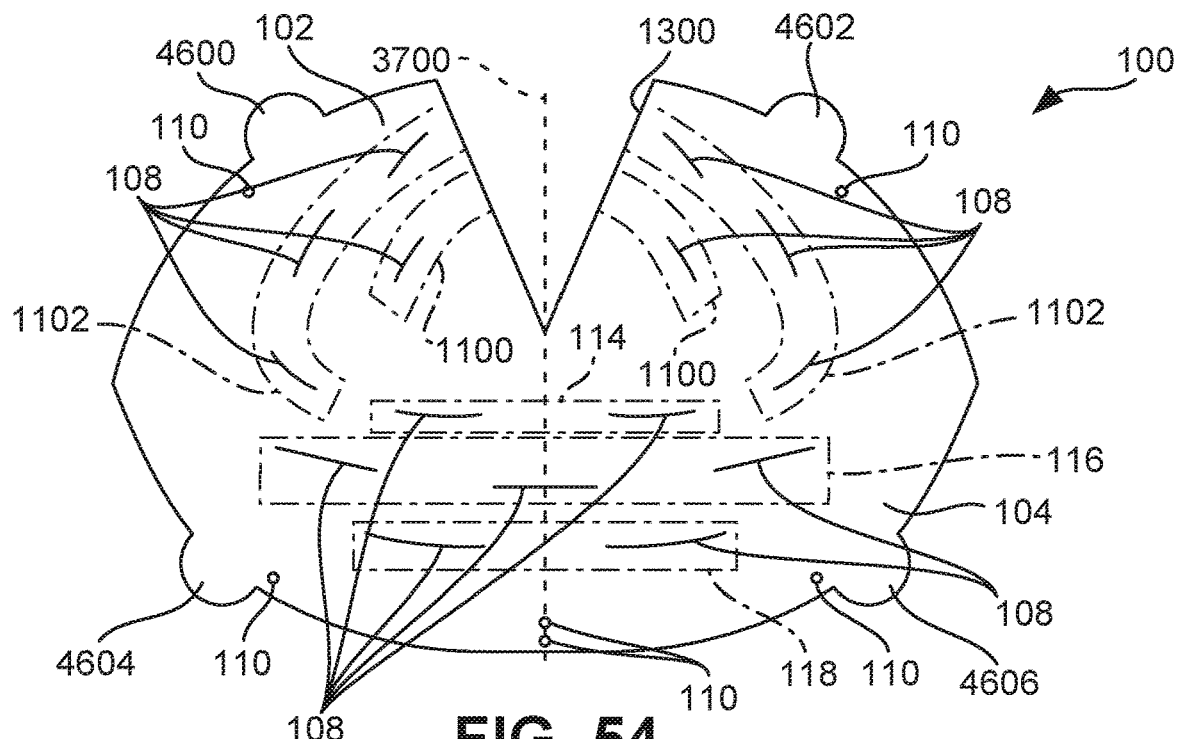
FIG. 54 is a top view of another example reconstruction support shown in a flat state and being constructed from a single piece of material.

In FIG. 54, both the upper half 102 and the lower half 104 are integrated as a single panel that is shaped like a rounded pentagon. FIG. 54 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the lower half 104. The reconstruction support 100 also includes the plurality of fenestrations 108. The plurality of fenestrations 108 is arranged in the first row 114, the second row 116, the third row 118, the first arc 1100, and the second arc 1102. FIG. 52 also illustrates the reconstruction support 100 as including the vertical appliqué 1300. FIG. 52 also illustrates the reconstruction support 100 as including the first tab 4600, the second tab 4602, the third tab 4604, and the fourth tab 4606.

Figure 55:
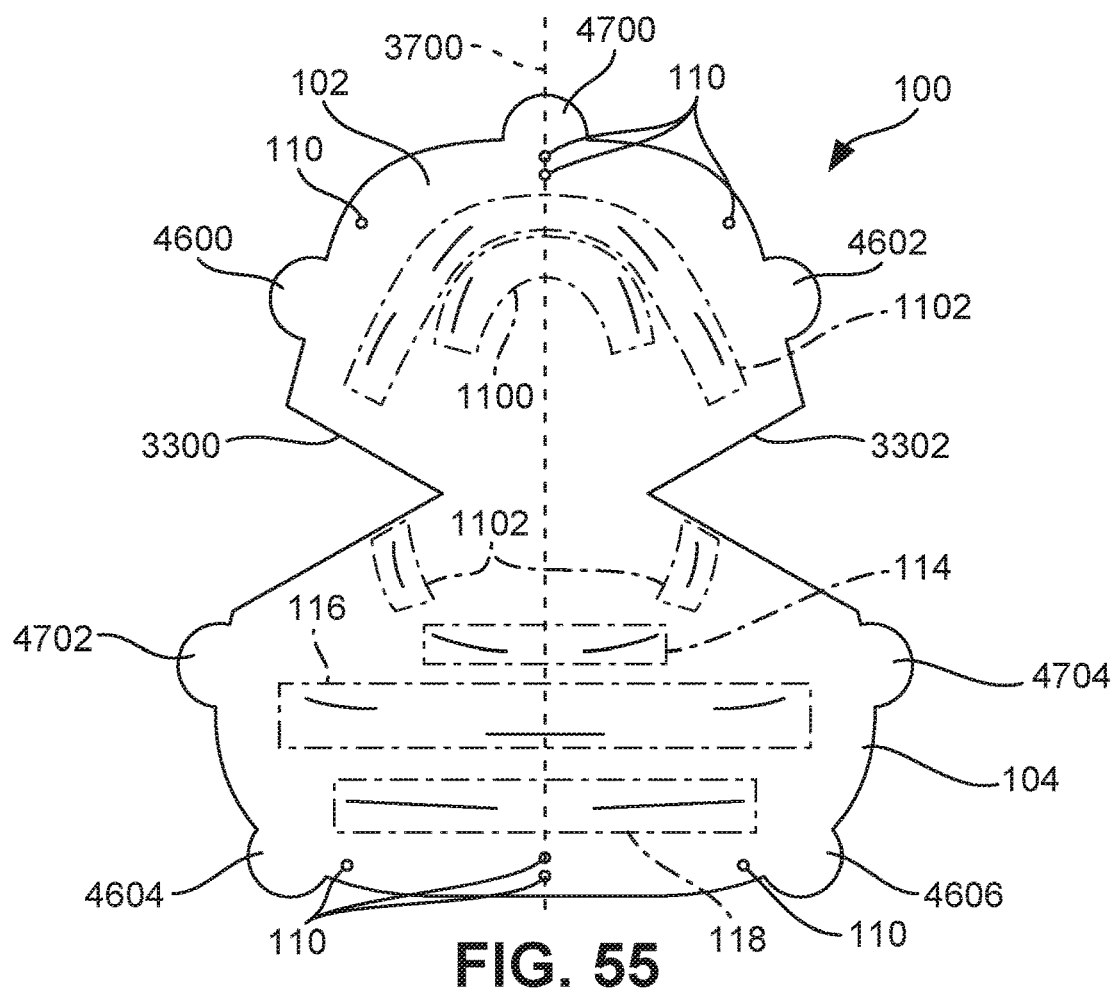
FIG. 55 is a top view of another example reconstruction support shown in a flat state and being constructed from a single piece of material.

In FIG. 55, both the upper half 102 and the lower half 104 are integrated as a single panel that is an ellipsoid. FIG. 55 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. The reconstruction support 100 also includes the plurality of fenestrations 108. The plurality of fenestrations 108 is arranged in the first row 114, the second row 116, the third row 118, the first arc 1100, and the second arc 1102. FIG. 55 also illustrates the reconstruction support 100 as including the first horizontal appliqué 3300 and the second horizontal appliqué 3302. FIG. 55 also illustrates the reconstruction support 100 as including the first tab 4600, the second tab 4602, the third tab 4604, the fourth tab 4606, the fifth tab 4700, the sixth tab 4702, and the seventh tab 4704. In some embodiments, the reconstruction support 100 does not include the alignment perforations 110.

Figure 56:
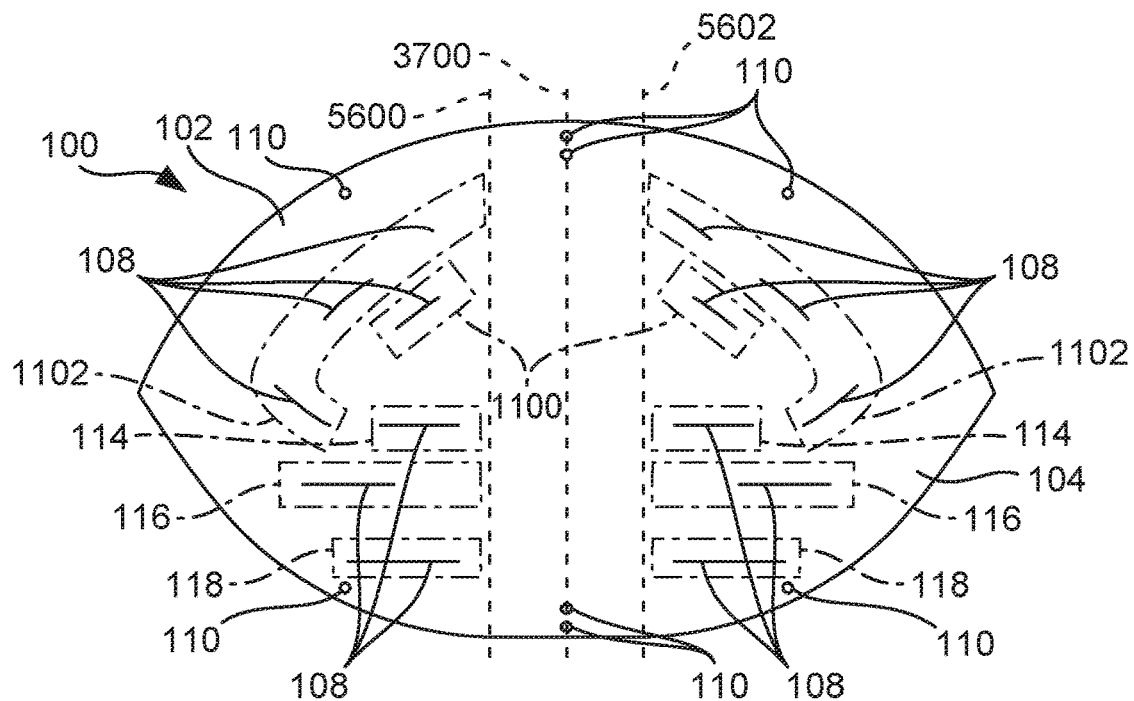
FIG. 56 is a top view of another example reconstruction support shown in a flat state and being constructed from a single piece of material.

In FIG. 56, both the upper half 102 and the lower half 104 are integrated as a single panel that is shaped like a rounded pentagon. FIG. 56 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. The reconstruction support 100 also includes the plurality of fenestrations 108. The plurality of fenestrations 108 is arranged in the first row 114, the second row 116, the third row 118, the first arc 1100, and the second arc 1102. In some embodiments, the fenestrations 108 may be arranged in a plurality of concentric arcs such that a majority of the fenestrations 108 are at least partially disposed in the lower half 104 and a minority of the fenestrations 108 are at least partially disposed in the upper half 102. FIG. 56 illustrates an embodiment where the plurality of fenestrations 108 is positioned such that a center gap across the reconstruction support 100, from the lower half 104 to the upper half 102, is formed. The center gap is bounded by a first boundary plane 5600 and a second boundary plane 5602. The first boundary plane 5600 is substantially parallel to the vertical plane 3700 and the second boundary plane 5602 is substantially parallel to the vertical plane 3700. In some embodiments, the first boundary plane 5600 is separated from the vertical plane 3700 by 1 cm and the second boundary plane 5602 is separated from the vertical plane 3700 by 1 cm.

Figure 57:
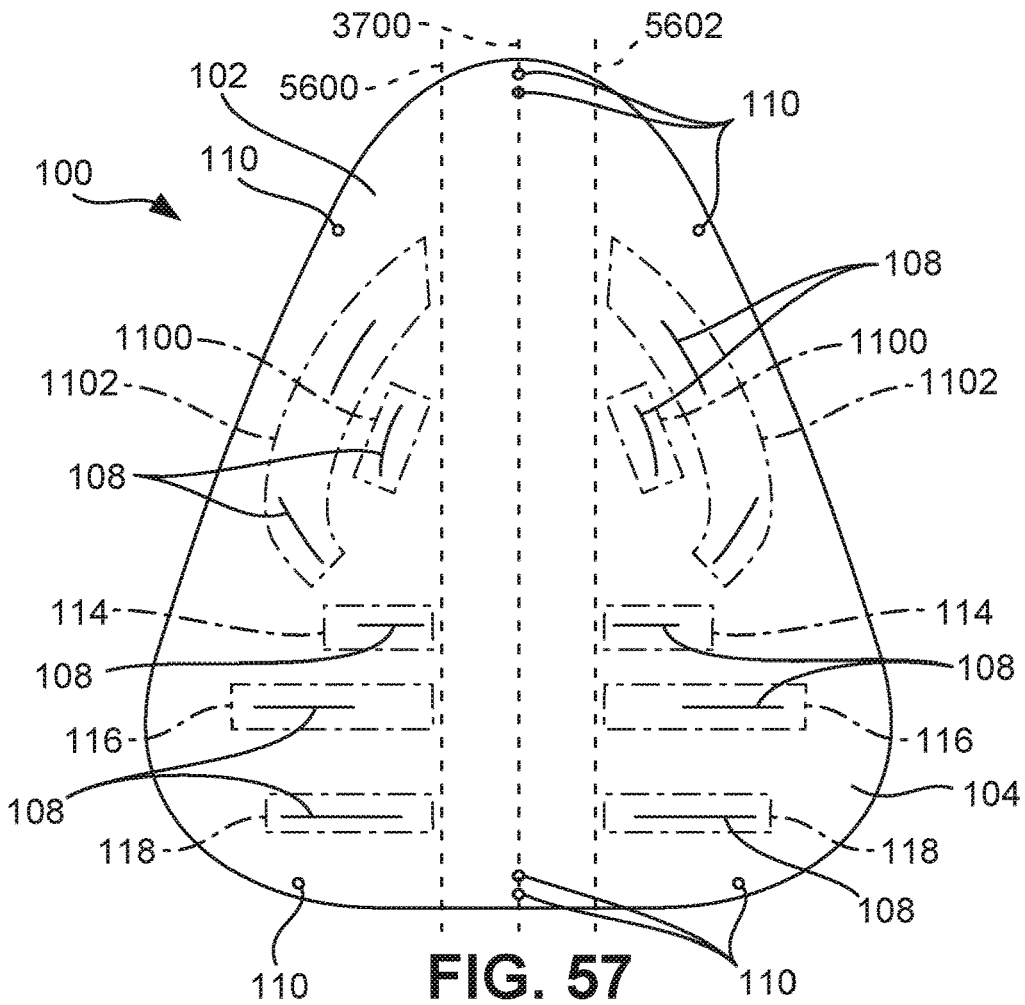
FIG. 57 is a top view of another example reconstruction support shown in a flat state and being constructed from a single piece of material.

In FIG. 57, both the upper half 102 and the lower half 104 are integrated as a single panel that is an ellipsoid. FIG. 57 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. The reconstruction support 100 also includes the plurality of fenestrations 108. The plurality of fenestrations 108 is arranged in the first row 114, the second row 116, the third row 118, the first arc 1100, and the second arc 1102. In some embodiments, the fenestrations 108 may be arranged in a plurality of concentric arcs such that a majority of the fenestrations 108 are at least partially disposed in the lower half 104 and a minority of the fenestrations 108 are at least partially disposed in the upper half 102. FIG. 57 also illustrates an embodiment where the plurality of fenestrations 108 is positioned such that a center gap across the reconstruction support 100, from the lower half 104 to the upper half 102, is formed. The center gap is bounded by the first boundary plane 5600 and the second boundary plane 5602. In some embodiments, the first boundary plane 5600 is separated from the vertical plane 3700 by 1 cm and the second boundary plane 5602 is separated from the vertical plane 3700 by 1 cm.

Figure 58:
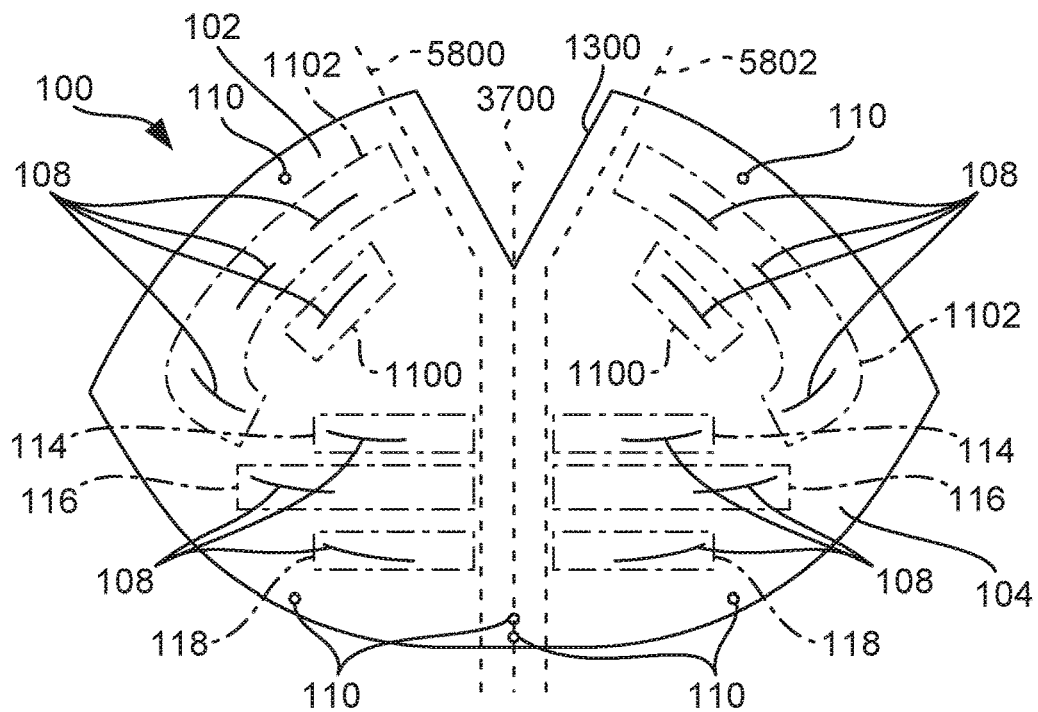
FIG. 58 is a top view of another example reconstruction support shown in a flat state and being constructed from a single piece of material.

In FIG. 58, both the upper half 102 and the lower half 104 are integrated as a single panel that is shaped like a rounded pentagon. FIG. 58 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the lower half 104. The reconstruction support 100 also includes the plurality of fenestrations 108. The plurality of fenestrations 108 is arranged in the first row 114, the second row 116, the third row 118, the first arc 1100, and the second arc 1102. FIG. 58 also illustrates the reconstruction support 100 as including the vertical appliqué 1300. In some embodiments, the fenestrations 108 may be arranged in a plurality of concentric arcs such that a majority of the fenestrations 108 are at least partially disposed in the lower half 104 and a minority of the fenestrations 108 are at least partially disposed in the upper half 102. FIG. 58 also illustrates an embodiment where the plurality of fenestrations 108 is positioned such that a center gap across the reconstruction support 100, from the lower half 104 to the upper half 102, is formed. The center gap is bounded by the first boundary plane 5600 and the second boundary plane 5602 and by a third boundary plane 5800 and a fourth boundary plane 5802. The third boundary plane 5800 extends from the first boundary plane 5600 towards a top edge of the upper half 102 and the fourth boundary plane 5802 extends from the second boundary plane 5602 towards the top edge of the upper half 102. The third boundary plane 5800 and the fourth boundary plane 5802 function to separate the fenestrations 108 from the vertical appliqué 1300. In some embodiments, the first boundary plane 5600 is separated from the vertical plane 3700 by 1 cm, the second boundary plane 5602 is separated from the vertical plane 3700 by 1 cm, the third boundary plane 5800 is separated from the vertical appliqué 1300 by 1 cm, and the fourth boundary plane 5802 is separated from the vertical appliqué 1300 by 1 cm. In some embodiments, the reconstruction support 100 also includes the first tab 4600, the second tab 4602, the third tab 4604, and/or the fourth tab 4606, as previously described.

Figure 59:
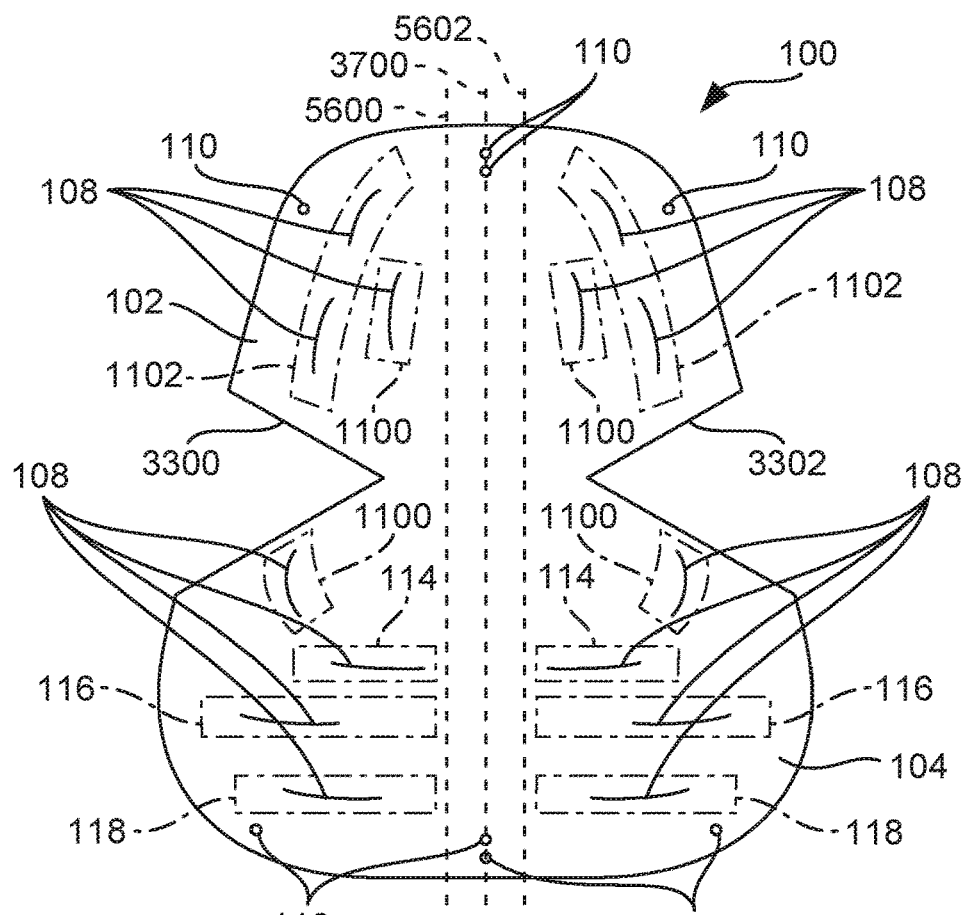
FIG. 59 is a top view of another example reconstruction support shown in a flat state and being constructed from a single piece of material.

In FIG. 59, both the upper half 102 and the lower half 104 are integrated as a single panel that is an ellipsoid. FIG. 59 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. The reconstruction support 100 also includes the plurality of fenestrations 108. The plurality of fenestrations 108 is arranged in the first row 114, the second row 116, the third row 118, the first arc 1100, and the second arc 1102. FIG. 59 also illustrates the reconstruction support 100 as including the first horizontal appliqué 3300 and the second horizontal appliqué 3302. FIG. 59 also illustrates an embodiment where the plurality of fenestrations 108 is positioned such that a center gap across the reconstruction support 100, from the lower half 104 to the upper half 102, is formed. The center gap is bounded by the first boundary plane 5600 and the second boundary plane 5602. In some embodiments, the first boundary plane 5600 is separated from the vertical plane 3700 by 1 cm and the second boundary plane 5602 is separated from the vertical plane 3700 by 1 cm. In some embodiments, the reconstruction support 100 also includes the first tab 4600, the second tab 4602, the third tab 4604, the fourth tab 4606, the fifth tab 4700, the sixth tab 4702, and/or the seventh tab 4704, as previously described.

Figure 60:
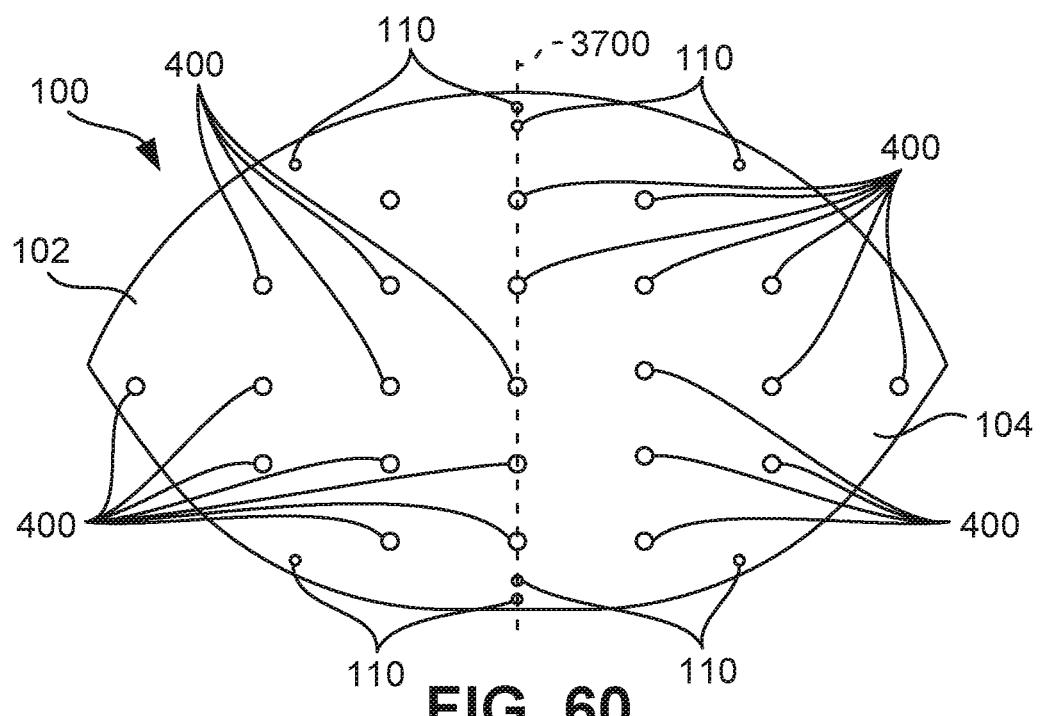
FIG. 60 is a top view of another example reconstruction support shown in a flat state and being constructed from a single piece of material.

In FIG. 60, both the upper half 102 and the lower half 104 are integrated as a single panel that is shaped like a rounded pentagon. FIG. 60 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. FIG. 60 also illustrates an embodiment where the reconstruction support 100 includes the plurality of egress perforations 400. FIG. 60 illustrates an embodiment where the egress perforations 400 are arranged in a plurality of substantially parallel rows having a plurality of substantially aligned columns. In some embodiments, the reconstruction support 100 also includes the vertical appliqué 1300, as previously described. In some embodiments, the reconstruction support 100 also includes the first tab 4600, the second tab 4602, the third tab 4604, and/or the fourth tab 4606, as previously described. In some embodiments, the reconstruction support 100 also includes the vertical appliqué 1300, the first tab 4600, the second tab 4602, the third tab 4604, and/or the fourth tab 4606, as previously described. In some embodiments, the rows of egress perforations 400 are arranged such that the egress perforations 400 in one row may be staggered relative to the egress perforations 400 in an adjacent row. In an example embodiment, each of the egress perforations 400 is at least 5 mm from any of the fenestrations 108.

Figure 61:
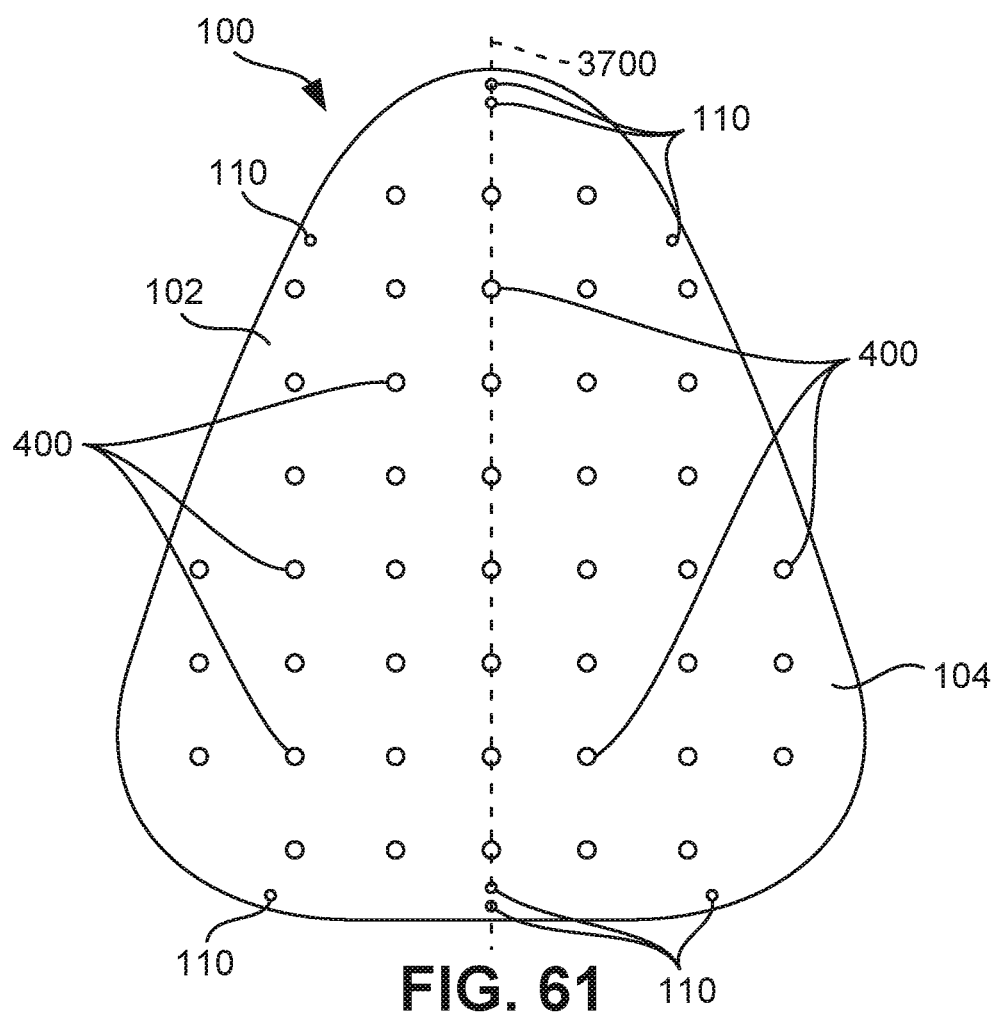
FIG. 61 is a top view of another example reconstruction support shown in a flat state and being constructed from a single piece of material.

In FIG. 61, both the upper half 102 and the lower half 104 are integrated as a single panel that is an ellipsoid. FIG. 61 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. The reconstruction support 100 also includes the plurality of egress perforations 400. FIG. 61 illustrates an embodiment where the egress perforations 400 are arranged in a plurality of substantially parallel rows having a plurality of substantially aligned columns. In some embodiments, the reconstruction support 100 also includes the first horizontal appliqué 3300 and the second horizontal appliqué 3302, as previously described. In some embodiments, the reconstruction support 100 also includes the first horizontal appliqué 3300, the second horizontal appliqué 3302, the first tab 4600, the second tab 4602, the third tab 4604, the fourth tab 4606, the fifth tab 4700, the sixth tab 4702, and/or the seventh tab 4704, as previously described. In some embodiments, the rows of egress perforations 400 are arranged such that the egress perforations 400 in one row may be staggered relative to the egress perforations 400 in an adjacent row. In an example embodiment, each of the egress perforations 400 is at least 5 mm from any of the fenestrations 108.

Figure 62:
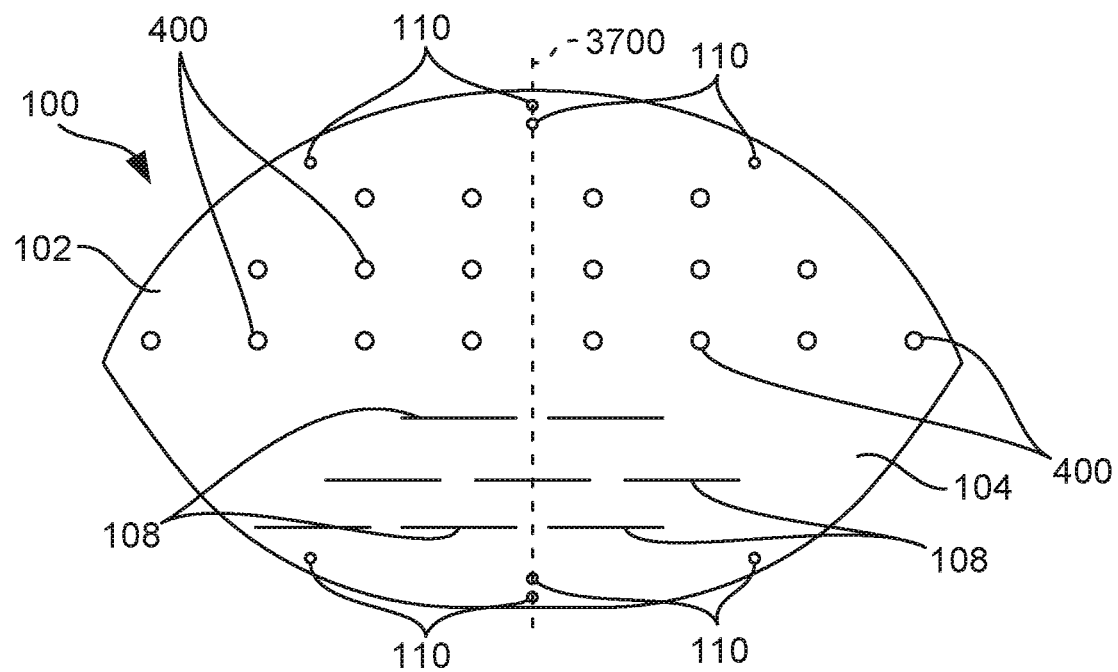
FIG. 62 is a top view of another example reconstruction support shown in a flat state and being constructed from a single piece of material.

In FIG. 62, both the upper half 102 and the lower half 104 are integrated as a single panel that is shaped like a rounded pentagon. FIG. 62 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. FIG. 62 also illustrates an embodiment where the reconstruction support 100 includes the plurality of fenestrations 108 and the plurality of egress perforations 400. As shown in FIG. 62, the fenestrations 108 are separated from the egress perforations 400. The fenestrations 108 are disposed within the lower half 104 while the egress perforations 400 may be disposed within the upper half 102. The fenestrations 108 and/or the egress perforations 400 may be arranged in a plurality of parallel rows. These parallel rows may be arranged such that adjacent rows of the fenestrations 108 are staggered or such that adjacent rows of the egress perforations 400 are staggered. In some embodiments, the reconstruction support 100 also includes the vertical appliqué 1300, as previously described. In some embodiments, the reconstruction support 100 also includes the first tab 4600, the second tab 4602, the third tab 4604, and/or the fourth tab 4606, as previously described. In some embodiments, the reconstruction support 100 also includes the vertical appliqué 1300, the first tab 4600, the second tab 4602, the third tab 4604, and/or the fourth tab 4606, as previously described. In an example embodiment, each of the egress perforations 400 is at least 5 mm from any of the fenestrations 108.

Figure 63:
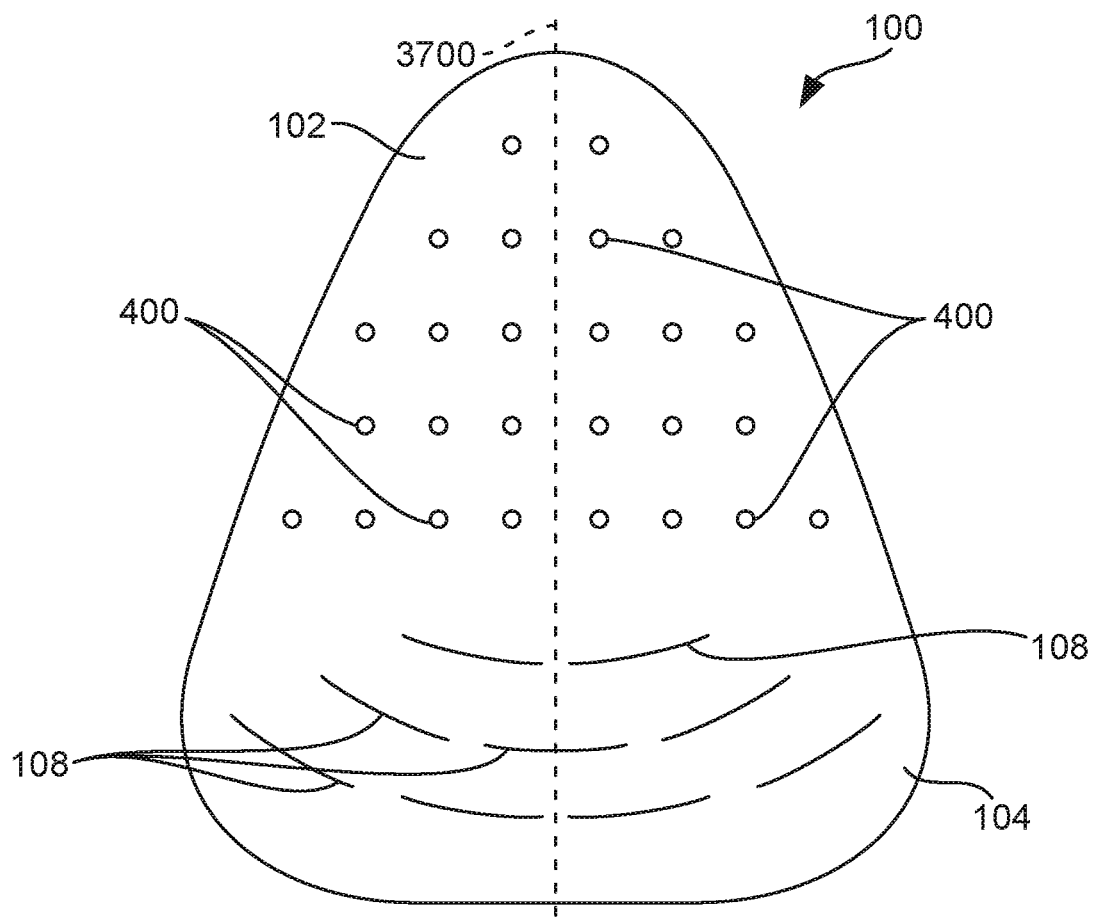
FIG. 63 is a top view of another example reconstruction support shown in a flat state and being constructed from a single piece of material.

In FIG. 63, both the upper half 102 and the lower half 104 are integrated as a single panel that is an ellipsoid. FIG. 63 also illustrates an embodiment where the reconstruction support 100 includes the plurality of fenestrations 108 and the plurality of egress perforations 400. As shown in FIG. 63, the fenestrations 108 are separated from the egress perforations 400. The fenestrations 108 are disposed within the lower half 104 while the egress perforations 400 may be disposed within the upper half 102. The fenestrations 108 and/or the egress perforations 400 may be arranged in a plurality of parallel rows. These parallel rows may be arranged such that adjacent rows of the fenestrations 108 are staggered or such that adjacent rows of the egress perforations 400 are staggered. In some embodiments, the reconstruction support 100 also includes the first horizontal appliqué 3300 and the second horizontal appliqué 3302, as previously described. In some embodiments, the reconstruction support 100 also includes the first horizontal appliqué 3300, the second horizontal appliqué 3302, the first tab 4600, the second tab 4602, the third tab 4604, the fourth tab 4606, the fifth tab 4700, the sixth tab 4702, and/or the seventh tab 4704, as previously described. In an example embodiment, each of the egress perforations 400 is at least 5 mm from any of the fenestrations 108.

Figure 64:
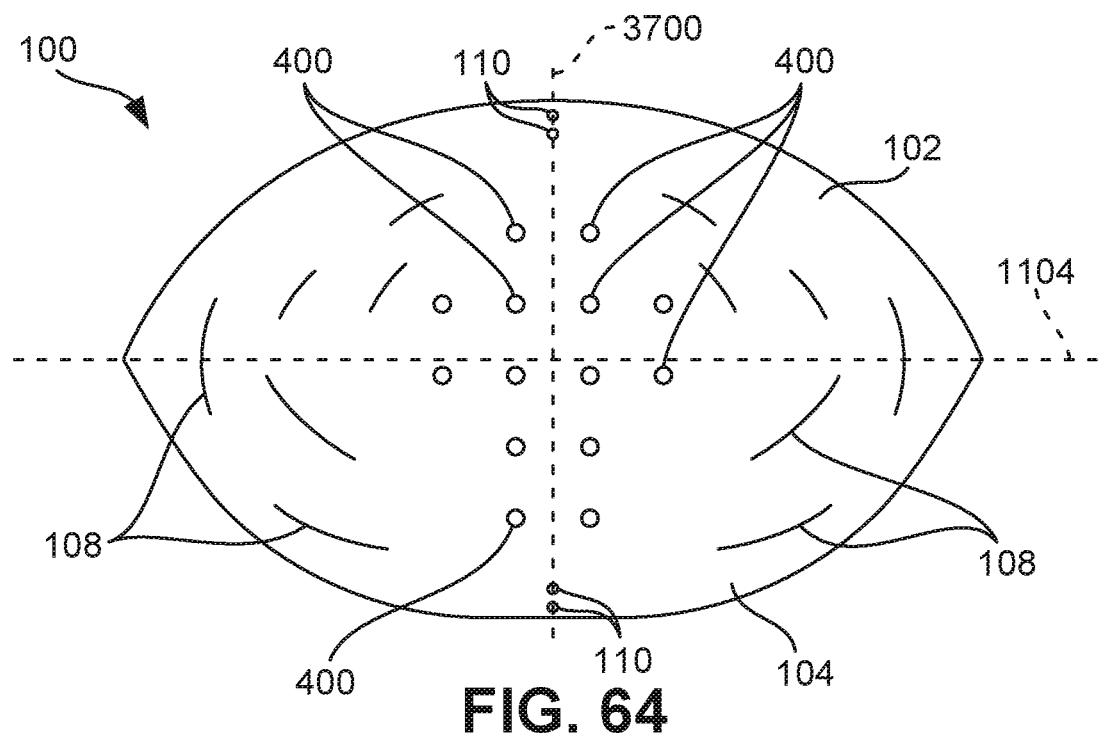
FIG. 64 is a top view of another example reconstruction support shown in a flat state and being constructed from a single piece of material.

In FIG. 64, both the upper half 102 and the lower half 104 are integrated as a single panel that is shaped like a rounded pentagon. FIG. 64 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. FIG. 64 also illustrates an embodiment where the reconstruction support 100 includes the plurality of fenestrations 108 and the plurality of egress perforations 400. As shown in FIG. 64, the fenestrations 108 are separated from the egress perforations 400. The fenestrations 108 are positioned on both the upper half 102 and the lower half 104. Similarly, the egress perforations 400 are positioned on both the upper half 102 and the lower half 104. The egress perforations 400 are arranged in two substantially parallel rows centered on the horizontal plane 1104 and two substantially parallel columns centered on the vertical plane 3700, thereby forming a cross shape centered on a center point of the reconstruction support 100. The fenestrations 108 are disposed on the reconstruction support 100 about the shape formed by the egress perforations 400. These parallel rows and/or columns may be arranged such that adjacent rows and/or columns of the egress perforations 400 are staggered. In some embodiments, the reconstruction support 100 also includes the vertical appliqué 1300, as previously described. In some embodiments, the reconstruction support 100 also includes the first tab 4600, the second tab 4602, the third tab 4604, and/or the fourth tab 4606, as previously described. In some embodiments, the reconstruction support 100 also includes the vertical appliqué 1300, the first tab 4600, the second tab 4602, the third tab 4604, and/or the fourth tab 4606, as previously described. In an example embodiment, each of the egress perforations 400 is at least 5 mm from any of the fenestrations 108.

Figure 65:
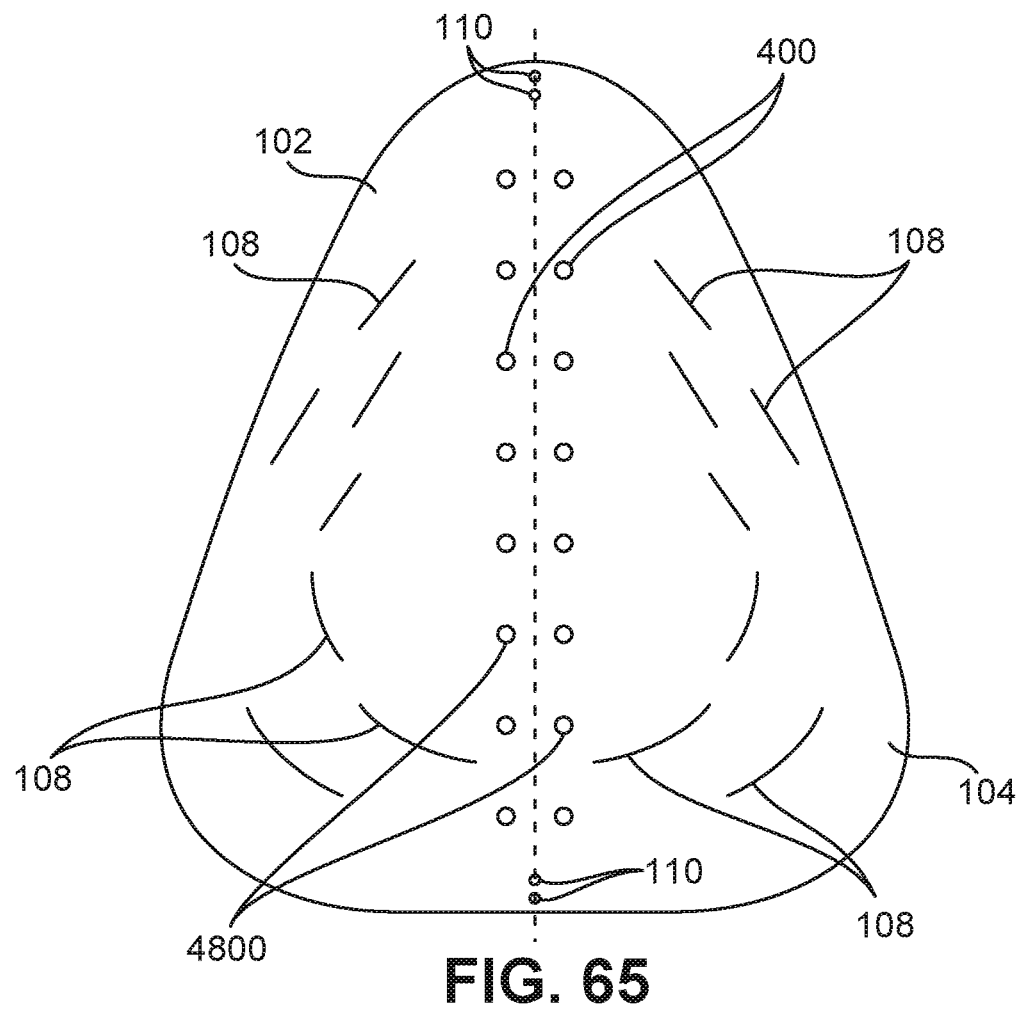
FIG. 65 is a top view of another example reconstruction support shown in a flat state and being constructed from a single piece of material.

In FIG. 65, both the upper half 102 and the lower half 104 are integrated as a single panel that is an ellipsoid. FIG. 65 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. FIG. 65 also illustrates an embodiment where the reconstruction support 100 includes the plurality of fenestrations 108 and the plurality of egress perforations 400. As shown in FIG. 65, the fenestrations 108 are separated from the egress perforations 400. The egress perforations 400 are arranged in two substantially parallel columns centered on the vertical plane 3700. The fenestrations 108 are disposed on the reconstruction support 100 about the shape formed by the egress perforations 400. These parallel columns may be arranged such that adjacent columns of the egress perforations 400 are staggered. In some embodiments, the reconstruction support 100 also includes the first horizontal appliqué 3300, the second horizontal appliqué 3302, the first tab 4600, the second tab 4602, the third tab 4604, the fourth tab 4606, the fifth tab 4700, the sixth tab 4702, and/or the seventh tab 4704, as previously described. In an example embodiment, each of the egress perforations 400 is at least 5 mm from any of the fenestrations 108.

Figure 66:
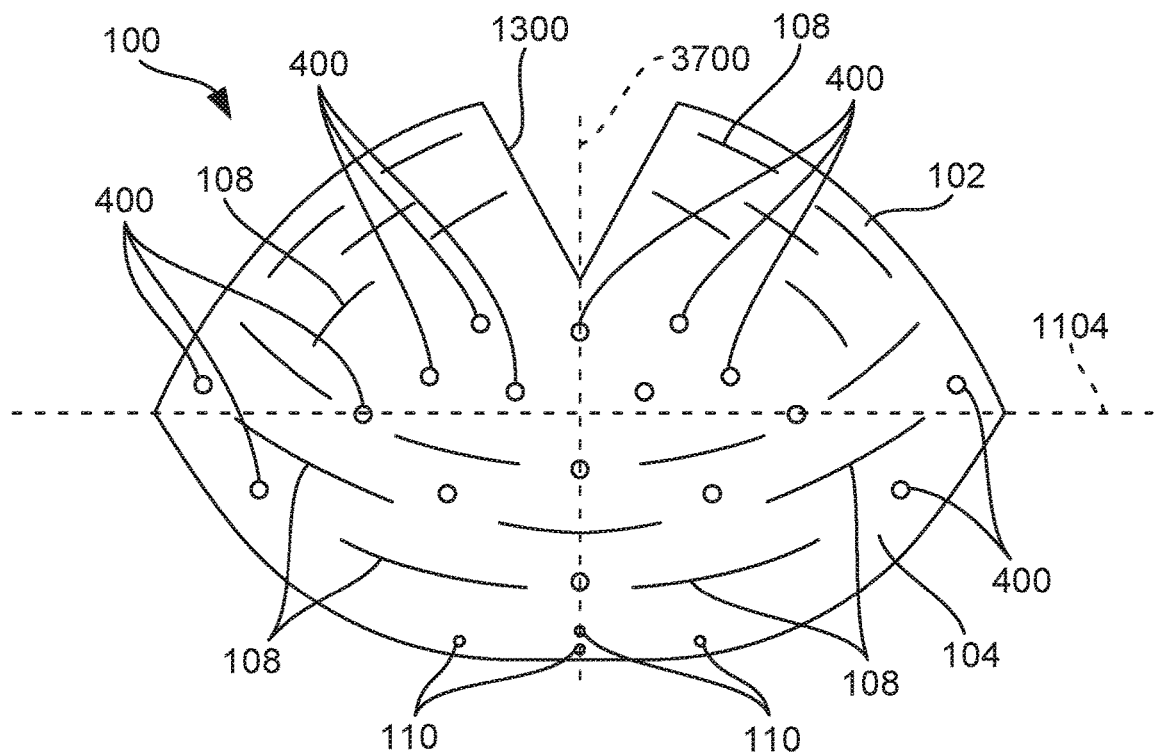
FIG. 66 is a top view of another example reconstruction support shown in a flat state and being constructed from a single piece of material.

In FIG. 66, both the upper half 102 and the lower half 104 are integrated as a single panel that is shaped like a rounded pentagon. FIG. 66 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the lower half 104. The reconstruction support 100 also includes the plurality of fenestrations 108 and the plurality of egress perforations 400. The plurality of fenestrations 108 is generally arranged in two groups of concentric arcs, a first group of concentric arcs disposed on the upper half 102 and a second group of concentric arcs disposed on the lower half 104. These concentric arcs are similar to the first arc 1100 and the second arc 1102. The egress perforations 400 are positioned proximate a center point of the reconstruction support 100 and dispersed between adjacent fenestrations 108. Specifically, some of the egress perforations 400 are located in a center region of the reconstruction support 100 between two arcs of the fenestrations 108, and therefore separated from the fenestrations 108, while others of the egress perforations 400 are alternated with the fenestrations 108 in some of the concentric arcs of the fenestrations 108. The arcs of the fenestrations 108 within which the egress perforations 400 are alternated are at least primarily disposed in the lower half 104. FIG. 66 also illustrates the reconstruction support 100 as including the vertical appliqué 1300. In some embodiments, the fenestrations 108 may be arranged in a plurality of concentric arcs such that a majority of the fenestrations 108 are at least partially disposed in the lower half 104 and a minority of the fenestrations 108 are at least partially disposed in the upper half 102. In some embodiments, the reconstruction support 100 does not include the vertical appliqué 1300. In some embodiments, the reconstruction support 100 also includes the first tab 4600, the second tab 4602, the third tab 4604, and/or the fourth tab 4606, as previously described. In an example embodiment, each of the egress perforations 400 is at least 5 mm from any of the fenestrations 108.

Figure 67:
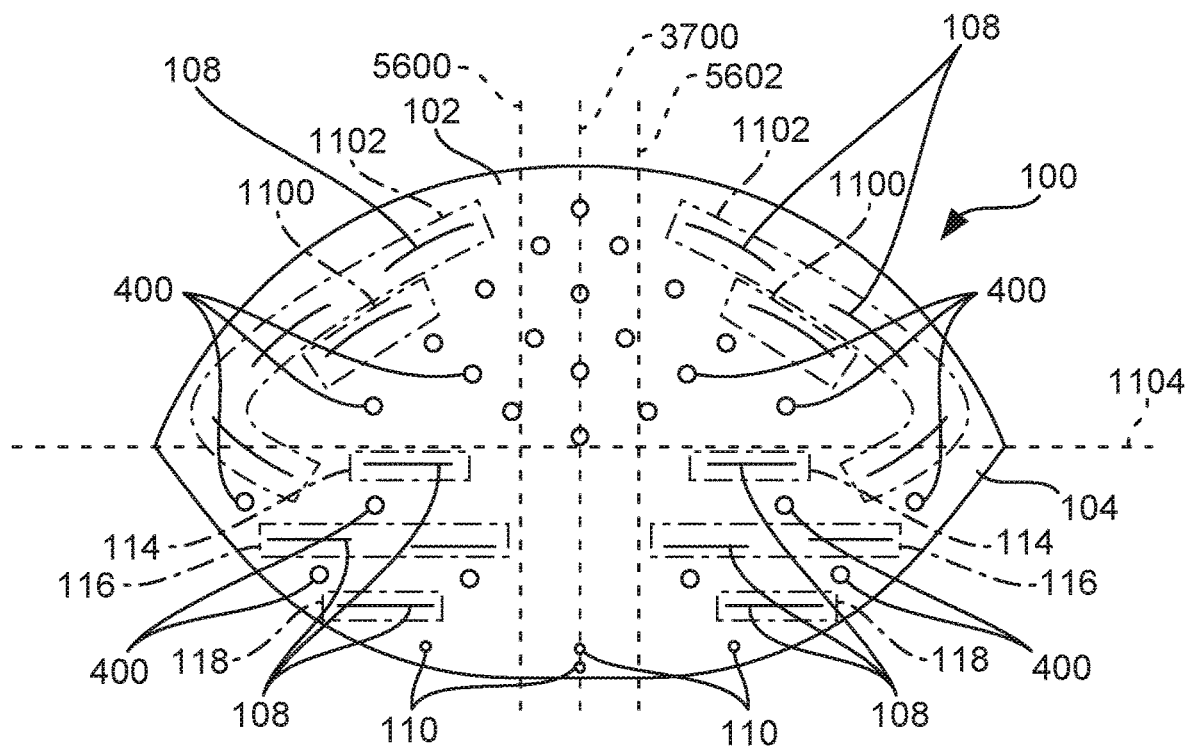
FIG. 67 is a top view of another example reconstruction support shown in a flat state and being constructed from a single piece of material.

In FIG. 67, both the upper half 102 and the lower half 104 are integrated as a single panel that is an ovoid. FIG. 67 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the lower half 104. The reconstruction support 100 also includes the plurality of fenestrations 108 and the plurality of egress perforations 400. The plurality of fenestrations 108 is arranged in the first row 114, the second row 116, the third row 118, the first arc 1100, and the second arc 1102. The egress perforations 400 are positioned proximate a center point of the upper half 102 and dispersed between the first row 114 and the second row 116 and between the second row 116 and the third row 118. Specifically, some of the egress perforations 400 are located in a center region of the reconstruction support 100 between first arc 1100 and first row 114, and therefore separated from the fenestrations 108, while others of the egress perforations 400 are disposed (i) in rows which are substantially parallel to the first row 114, the second row 116, and the third row 118 and (ii) between the first row 114 and the second row 116 and between the second row 116 and the third row 118. FIG. 67 also illustrates an embodiment where the plurality of fenestrations 108 and the egress perforations 400 are positioned such that a center gap across the reconstruction support 100, from the lower half 104 to the horizontal plane 1104, is formed. The center gap is bounded by the first boundary plane 5600, the second boundary plane 5602, and the horizontal plane 1104. In some embodiments, the first boundary plane 5600 is separated from the vertical plane 3700 by 1 cm and the second boundary plane 5602 is separated from the vertical plane 3700 by 1 cm. In some embodiments, the reconstruction support 100 also includes the vertical appliqué 1300, the first tab 4600, the second tab 4602, the third tab 4604, and/or the fourth tab 4606, as previously described. In an example embodiment, each of the egress perforations 400 is at least 5 mm from any of the fenestrations 108.

Figure 68:
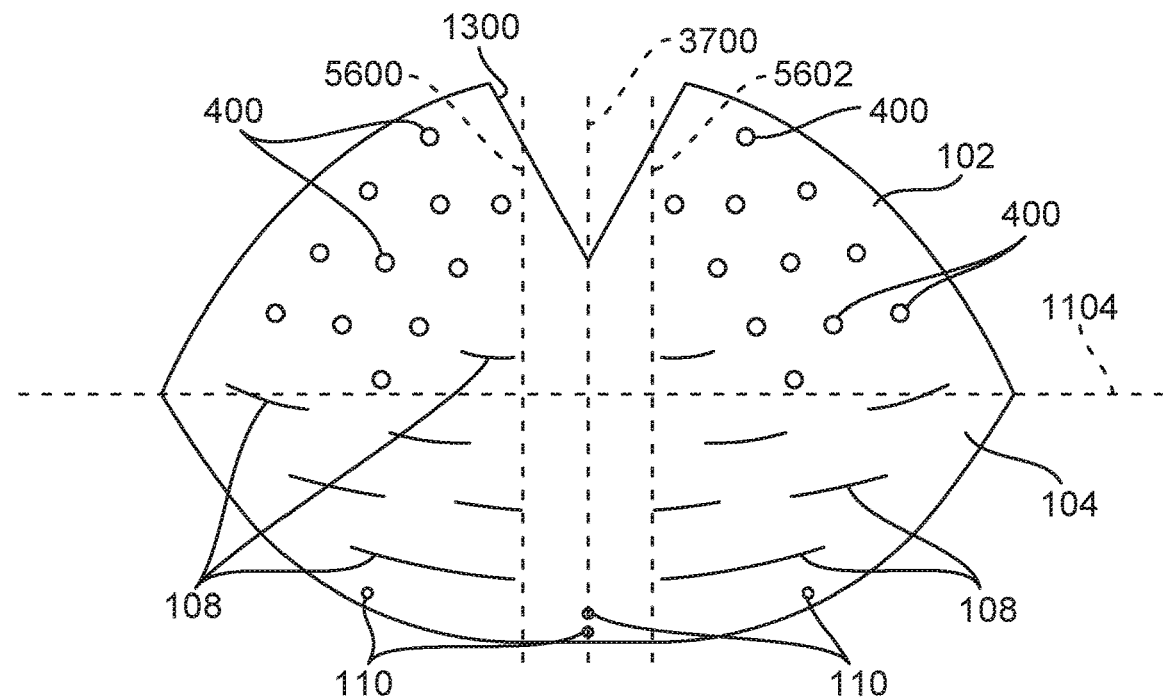
FIG. 68 is a top view of another example reconstruction support shown in a flat state and being constructed from a single piece of material.

In FIG. 68, both the upper half 102 and the lower half 104 are integrated as a single panel that is shaped like a rounded pentagon. FIG. 68 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the lower half 104. The reconstruction support 100 also includes the plurality of fenestrations 108 and the plurality of egress perforations 400. The plurality of fenestrations 108 is generally arranged in a plurality of concentric arcs, a majority of the fenestrations 108 being disposed on the lower half 104. These concentric arcs are similar to the first arc 1100 and the second arc 1102. The egress perforations 400 are positioned on the upper half 102. The reconstruction support 100 includes the vertical appliqué 1300. The egress perforations 400 are symmetrically disposed on opposite sides of the vertical plane 3700. In some embodiments, the reconstruction support 100 also includes the first tab 4600, the second tab 4602, the third tab 4604, and/or the fourth tab 4606, as previously described. In an example embodiment, each of the egress perforations 400 is at least 5 mm from any of the fenestrations 108.

Figure 69:
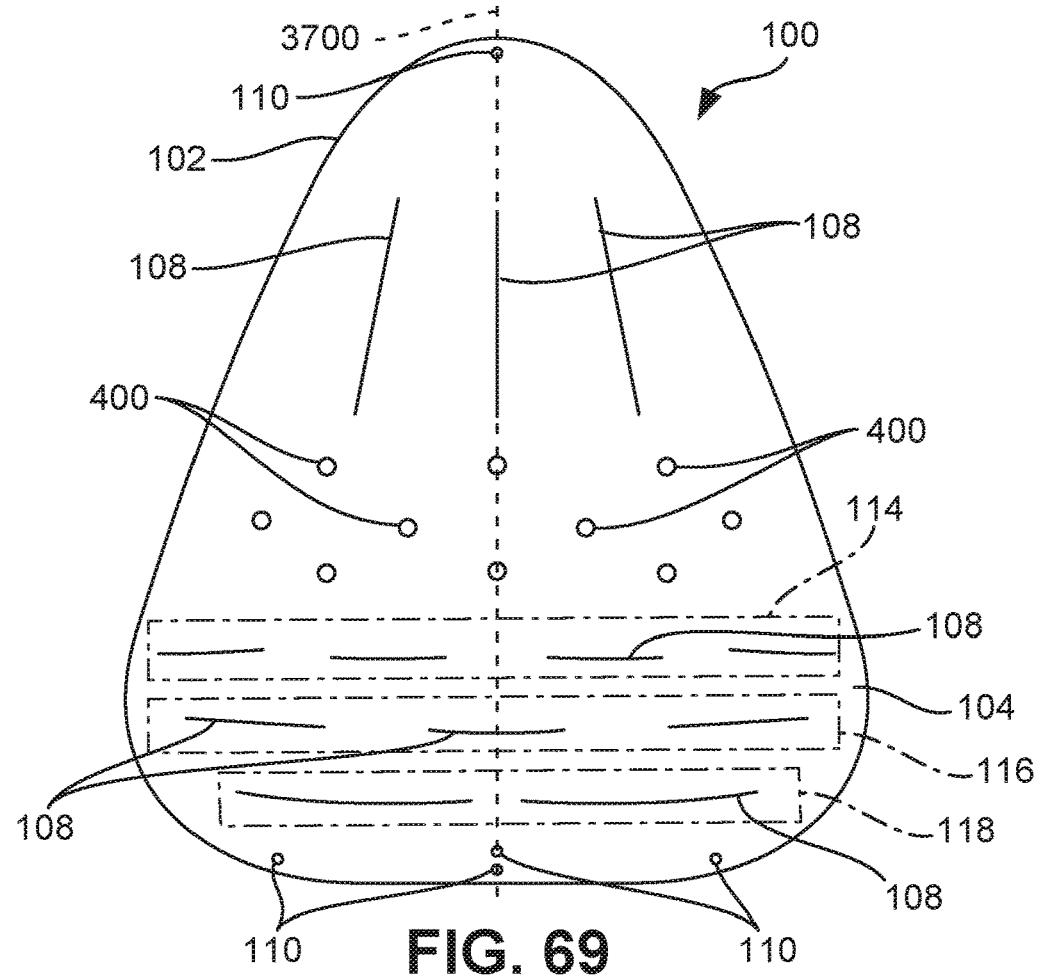
FIG. 69 is a top view of another example reconstruction support shown in a flat state and being constructed from a single piece of material.

In FIG. 69, both the upper half 102 and the lower half 104 are integrated as a single panel that is an ellipsoid. FIG. 69 illustrates an embodiment where the alignment perforations 110 are positioned along a perimeter of the reconstruction support 100. The alignment perforations 110 are configured such that one of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. FIG. 69 also illustrates an embodiment where the reconstruction support 100 includes the plurality of fenestrations 108 and the plurality of egress perforations 400. As shown in FIG. 69, the fenestrations 108 are separated from the egress perforations 400. The egress perforations 400 are arranged in three substantially parallel rows centered on the vertical plane 3700. These parallel rows may be arranged such that adjacent rows of the egress perforations 400 are staggered. The fenestrations 108 are disposed on the reconstruction support 100 between the egress perforations 400 and a top edge of the upper half 102 and between the egress perforations 400 and a bottom edge of the lower half 104. The fenestrations 108 disposed between the egress perforations 400 and the top edge of the upper half 102 are oriented towards an intersection of the top edge and the vertical plane 3700. The fenestrations 108 disposed between the egress perforations 400 and the bottom edge of the lower half 104 are arranged in the first row 114, the second row 116, and the third row 118. In some embodiments, the reconstruction support 100 also includes the first horizontal appliqué 3300, the second horizontal appliqué 3302, the first tab 4600, the second tab 4602, the third tab 4604, the fourth tab 4606, the fifth tab 4700, the sixth tab 4702, and/or the seventh tab 4704, as previously described. In an example embodiment, each of the egress perforations 400 is at least 5 mm from any of the fenestrations 108.

In FIG. 70, both the upper half 102 and the lower half 104 are integrated as a single panel that is shaped like a rounded pentagon. FIG. 70 illustrates an embodiment where the alignment perforations 110 are positioned along a perimeter of the reconstruction support 100. The alignment perforations 110 are configured such that two of the alignment perforations 110 are aligned on the vertical plane 3700 and disposed on a perimeter of the upper half 102 and two of the alignment perforations 110 are aligned on the vertical plane 3700 and disposed on a perimeter of the lower half 104. FIG. 70 illustrates an embodiment where the reconstruction support 100 includes the first horizontal appliqué 3300 and the second horizontal appliqué 3302. FIG. 70 also illustrates an embodiment where the reconstruction support 100 includes the plurality of fenestrations 108 and the plurality of egress perforations 400. FIG. 70 also illustrates an embodiment where the plurality of fenestrations 108 and the egress perforations 400 are positioned such that a center gap across the reconstruction support 100, from the lower half 104 to the horizontal plane 1104, is formed. The center gap is bounded by the first boundary plane 5600, the second boundary plane 5602, and the horizontal plane 1104. In some embodiments, the first boundary plane 5600 is separated from the vertical plane 3700 by 1 cm and the second boundary plane 5602 is separated from the vertical plane 3700 by 1 cm. As shown in FIG. 70, the fenestrations 108 are separated from the egress perforations 400. The egress perforations 400 are arranged in a first group, bounded by the fenestrations 108, the first boundary plane 5600, and the horizontal plane 1104, a second group, bounded by the fenestrations 108, the second boundary plane 5602, and the horizontal plane 1104, and a third group, bounded by the fenestrations 108 and the horizontal plane 1104. The fenestrations 108 are disposed on the upper half 102 and the lower half 104. Specifically, the fenestrations 108 are arranged between the egress perforations 400 and an outer edge of the reconstruction support 100 on the upper half 102 and in the first row 114, the second row 116, and the third row 118, on the lower half 104. In some embodiments, the reconstruction support 100 does not include the first horizontal appliqué 3300 and/or the second horizontal appliqué 3302. In some embodiments, the reconstruction support 100 also includes the first tab 4600, the second tab 4602, the third tab 4604, the fourth tab 4606, the fifth tab 4700, the sixth tab 4702, and/or the seventh tab 4704, as previously described. In an example embodiment, each of the egress perforations 400 is at least 5 mm from any of the fenestrations 108.

III. Construction of Exemplary Embodiments

While this specification contains many specific implementation details, these should not be construed as limitations on the scope of what may be claimed but rather as descriptions of features specific to particular implementations. Certain features described in this specification in the context of separate implementations can also be implemented in combination in a single implementation. Conversely, various features described in the context of a single implementation or embodiment can also be implemented in multiple implementations embodiments separately or in any suitable subcombination. Moreover, although features may be described as acting in certain combinations and even initially claimed as such, one or more features from a claimed combination can, in some cases, be excised from the combination, and the claimed combination may be directed to a subcombination or variation of a subcombination.

As utilized herein, the terms "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It is important to note that the construction and arrangement of the system shown in the various example implementations is illustrative only and not restrictive in character. All changes and modifications that come within the spirit and/or scope of the described implementations are desired to be protected. It should be understood that some features may not be necessary, and implementations lacking the various features may be contemplated as within the scope of the application, the scope being defined by the claims that follow. When the language "a portion" is used, the item can include a portion and/or the entire item unless specifically stated to the contrary.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

What is claimed is:

1. A reconstruction support configured for insertion above muscle for facilitation of breast reconstruction, comprising:
   an upper half;
   a lower half contiguous with the upper half; and
   a plurality of fenestrations disposed on at least one of the upper half or the lower half, the plurality of fenestrations configured to facilitate selective expansion of at least one of the upper half or the lower half, the plurality of fenestrations disposed in at least one arc;
   wherein the plurality of substantially parallel rows comprises:
      a first row;
      a second row positioned adjacent the first row; and
      a third row positioned adjacent the second row, such that the second row is positioned between the first row and the third row;
   wherein a first subset of the plurality of fenestrations is contained within the first row;
   wherein a second subset of the plurality of fenestrations is contained within the second row;
   wherein a third subset of the plurality of fenestrations is contained within the third row; and
   wherein a first length of each fenestration within the first subset of the plurality of fenestrations is less than a third length of each fenestration within the third subset of the plurality of fenestrations.

2. The reconstruction support of claim 1, wherein:
   the first length of each fenestration within the first subset of the plurality of fenestrations is less than a second length of each fenestration within the second subset of the plurality of fenestrations; and the third length of each fenestration within the third subset of the plurality of fenestrations is greater than the second length of each fenestration within the second subset of the plurality of fenestrations.

3. The reconstruction support of claim 2, wherein at least a portion of each fenestration within the second subset of the plurality of fenestrations overlaps (i) at least a portion of at least one fenestration within the first subset of the plurality of fenestrations and (ii) at least a portion of at least one fenestration within the third subset of the plurality of fenestrations.

4. The reconstruction support of claim 1, wherein the plurality of fenestrations is arranged in a plurality of substantially concentric arcs in addition to the plurality of substantially parallel rows.

5. The reconstruction support of claim 4, wherein:
the plurality of substantially concentric arcs comprises:
a first arc; and
a second arc positioned adjacent the first arc;
a fourth subset of the plurality of fenestrations is contained within the first arc;
a fifth subset of the plurality of fenestrations is contained within the second arc; and
at least a portion of each fenestration within the fifth subset of the plurality of fenestrations overlaps at least a portion of at least one fenestration within the fourth subset of the plurality of fenestrations.

6. The reconstruction support of claim 5, wherein:
a fourth length of each fenestration within the fourth of the plurality of fenestrations is less than the third length of each fenestration within the third subset of the plurality of fenestrations; and
a fifth length of each fenestration within the fifth of the plurality of fenestrations is less than the third length of each fenestration within the third subset of the plurality of fenestrations.

7. The reconstruction support of claim 6, wherein:
the first length, a second length of each fenestration within the second subset of the plurality of fenestrations, the fourth length, and the fifth length are approximately equal to 2 centimeters; and
the third length is equal to approximately 3 centimeters.

8. The reconstruction support of claim 4, wherein:
at least a portion of at least one of the plurality of substantially concentric arcs is disposed on both the upper half and the lower half; and
the plurality of substantially parallel rows is contained on the upper half or the lower half.

9. A reconstruction support configured for insertion above muscle for facilitation of breast reconstruction, comprising:
an upper half;
a lower half contiguous with the upper half;
a plurality of fenestrations disposed on at least one of the upper half or the lower half, the plurality of fenestrations configured to facilitate selective expansion of at least one of the upper half or the lower half, the plurality of fenestrations disposed in at least one arc; and
a plurality of egress perforations disposed on at least one of the upper half or the lower half.

10. The reconstruction support of claim 9, wherein:
the plurality of fenestrations is disposed on the upper half or the lower half; and
the plurality of egress perforations is disposed on the other of the upper half and the lower half.

11. The reconstruction support of claim 9, wherein the plurality of egress perforations is arranged in a second plurality of substantially parallel rows.

12. The reconstruction support of claim 11, wherein:
the second plurality of substantially parallel rows comprises:
a fourth row; and
a fifth row positioned adjacent the fourth row;
a sixth subset of the plurality of egress perforations is contained within the fourth row; and
a seventh subset of the plurality of egress perforations is contained within the fifth row.

13. The reconstruction support of claim 12, wherein the sixth subset of the plurality of egress perforations is offset relative to the seventh subset of the plurality of egress perforations.

14. A reconstruction support configured for insertion above muscle for facilitation of breast reconstruction, comprising:
an upper half;
a lower half contiguous with the upper half; and
a plurality of fenestrations circumferentially disposed on at least one of the upper half or the lower half, the plurality of fenestrations configured to facilitate selective expansion of at least one of the upper half or the lower half;
wherein the plurality of fenestrations is arranged in a plurality of substantially concentric arcs comprising:
a first arc containing a first subset of the plurality of fenestrations; and
a second arc positioned adjacent the first arc and containing a second subset of the plurality of fenestrations;
wherein the reconstruction support is bisected by a horizontal plane; and
wherein the first arc and the second arc are bisected by the horizontal plane.

15. The reconstruction support of claim 14, wherein:
the plurality of fenestrations is arranged in a plurality of substantially parallel rows comprising:
a first row containing a third subset of the plurality of fenestrations;
a second row positioned adjacent the first row containing a fourth subset of the plurality of fenestrations; and
a third row positioned adjacent the second row such that the second row is positioned between the first row and the third row and containing a fifth subset of the plurality of fenestrations;
the horizontal plane separates the upper half from the lower half; and
the first row, the second row, and the third row are contained within the upper half or the lower half.

16. The reconstruction support of claim 15, wherein:
at least a portion of each fenestration within the fourth subset of the plurality of fenestrations overlaps at least a portion of (i) at least one fenestration within the third subset of the plurality of fenestrations and (ii) at least one fenestration within the fifth subset of the plurality of fenestrations; and
at least a portion of each fenestration within the second subset of the plurality of fenestrations overlaps at least a portion of at least one fenestration within the first subset of the plurality of fenestrations.

17. A reconstruction support configured for insertion above muscle for facilitation of breast reconstruction, comprising:

an upper half;

a lower half contiguous with the upper half;

a plurality of fenestrations circumferentially disposed on at least one of the upper half or the lower half, the plurality of fenestrations configured to facilitate selective expansion of at least one of the upper half or the lower half; and at least one of a first horizontal applique, a second horizontal applique, or a vertical applique.

18. A reconstruction support configured for insertion above muscle for facilitation of breast reconstruction, comprising:

an upper half;

a lower half contiguous with the upper half; and a plurality of fenestrations circumferentially disposed on at least one of the upper half or the lower half, the plurality of fenestrations configured to facilitate selective expansion of at least one of the upper half or the lower half;

wherein at least one of the plurality of fenestrations is curvilinear, radial, or oblique.

19. A reconstruction support configured for insertion above muscle for facilitation of breast reconstruction, comprising:

a plurality of fenestrations arranged in a first arc;

wherein the reconstruction support is bisected by a horizontal plane and a vertical plane that is orthogonal to the horizontal plane;

wherein the first arc is bisected by the horizontal plane and the vertical plane; and wherein the reconstruction support is substantially symmetrical about the vertical plane.

20. The reconstruction support of claim 19, wherein each of the plurality of fenestrations is at least 1.5 cm from the vertical plane.

21. The reconstruction support of claim 20, wherein:

the plurality of fenestrations is arranged in a first row containing a first subset of the plurality of fenestrations; and each fenestration within the first subset of the plurality of fenestrations has a length of at least 2 cm.

22. The reconstruction support of claim 19, wherein at least one of the plurality of fenestrations is curvilinear, radial, or oblique.

23. The reconstruction support of claim 19, further comprising:

an upper half; and a lower half sewn to the upper half;

wherein at least one of the plurality of fenestrations is disposed on the lower half.

* * * * *